United States Patent
Xu et al.

(10) Patent No.: US 10,975,352 B2
(45) Date of Patent: *Apr. 13, 2021

(54) METHODS OF ENHANCING CELL SURVIVAL OF STEM CELLS

(71) Applicant: The Scripps Research Institute, La Jolla, CA (US)

(72) Inventors: Yue Xu, San Diego, CA (US); Sheng Ding, La Jolla, CA (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/431,643

(22) Filed: Jun. 4, 2019

(65) Prior Publication Data

US 2019/0352600 A1 Nov. 21, 2019

Related U.S. Application Data

(60) Continuation of application No. 15/863,501, filed on Jan. 5, 2018, now Pat. No. 10,351,822, which is a continuation of application No. 15/098,546, filed on Apr. 14, 2016, now Pat. No. 9,896,655, which is a division of application No. 14/188,616, filed on Feb. 24, 2014, now Pat. No. 9,340,525, which is a division of application No. 13/132,379, filed as application No. PCT/US2009/066554 on Dec. 3, 2009, now Pat. No. 8,691,573.

(60) Provisional application No. 61/200,808, filed on Dec. 3, 2008.

(51) Int. Cl.

| | |
|---|---|
| *C12N 5/0735* | (2010.01) |
| *C07D 403/04* | (2006.01) |
| *C07D 417/14* | (2006.01) |
| *C07D 417/12* | (2006.01) |
| *C07D 239/48* | (2006.01) |
| *C07D 401/14* | (2006.01) |
| *C07D 401/04* | (2006.01) |
| *C07D 277/56* | (2006.01) |

(52) U.S. Cl.
CPC ......... *C12N 5/0606* (2013.01); *C07D 239/48* (2013.01); *C07D 277/56* (2013.01); *C07D 401/04* (2013.01); *C07D 401/14* (2013.01); *C07D 403/04* (2013.01); *C07D 417/12* (2013.01); *C07D 417/14* (2013.01); *C12N 2501/999* (2013.01)

(58) Field of Classification Search
CPC .. C12N 5/0735; C07D 403/04; C07D 417/14; C07D 417/12; C07D 239/48; C07D 401/04; C07D 401/14; C07D 277/56
USPC .......................................... 435/366; 514/275
See application file for complete search history.

(56) References Cited

U.S. PATENT DOCUMENTS

| | | | |
|---|---|---|---|
| 6,608,072 B1 | 8/2003 | Revesz | |
| 7,265,138 B2 | 9/2007 | Doherty et al. | |
| 8,004,201 B2 | 8/2011 | Hsueh et al. | |
| 8,044,201 B2 * | 10/2011 | Xu | A61P 9/10 544/322 |
| 8,691,573 B2 * | 4/2014 | Xu | A61P 35/00 435/375 |
| 9,340,525 B2 * | 5/2016 | Xu | C07D 277/56 |
| 9,896,655 B2 * | 2/2018 | Xu | C07D 239/48 |
| 10,351,822 B2 * | 7/2019 | Xu | A61P 1/04 |
| 2003/0225147 A1 | 12/2003 | Chu et al. | |
| 2004/0157845 A1 | 8/2004 | Doherty et al. | |
| 2008/0182328 A1 | 7/2008 | Snyder et al. | |
| 2009/0069360 A1 | 3/2009 | Batt et al. | |
| 2011/0224233 A1 | 9/2011 | Xu et al. | |
| 2011/0294761 A1 | 12/2011 | Xu et al. | |
| 2016/0304833 A1 | 10/2016 | Xu et al. | |

FOREIGN PATENT DOCUMENTS

| | | |
|---|---|---|
| CN | 101563449 A | 10/2009 |
| CN | 102307882 B | 6/2015 |
| EP | 0257275 | 3/1988 |
| EP | 0928790 A1 | 7/1999 |
| EP | 2370445 B1 | 7/2014 |
| EP | 2789618 A1 | 10/2014 |
| HK | 1161590 A1 | 10/2014 |
| IL | 213205 B | 3/2015 |
| IL | 228818 B1 | 7/2015 |
| JP | 2009530288 A | 8/2009 |
| JP | 5793795 B2 | 8/2015 |
| WO | 2001/30778 | 5/2001 |
| WO | 2002/00649 | 1/2002 |
| WO | 2002/056888 | 7/2002 |
| WO | 2003/004467 | 1/2003 |
| WO | 2003/004487 | 1/2003 |
| WO | 2004/072068 | 8/2004 |
| WO | 2004072068 A1 | 8/2004 |
| WO | 2005/096784 | 10/2005 |
| WO | 2006/078621 | 7/2006 |
| WO | 2006/101977 | 9/2006 |

(Continued)

OTHER PUBLICATIONS

EP09831108.7 , "Extended European Search Report Received", dated Jul. 11, 2012, 9 pages.
EP14175853.2 , "Extended European Search Report", dated Sep. 9, 2014, 7 Pages.
Beattie et al., "Activin A Maintains Pluripotency of Human Embryonic Stem Cells 0 in the Absence of Feeder Layers", Stem Cells, vol. 23, Issue 4, Apr. 2005, pp. 489-495.
CAS Registry No. 1023654-51-4; STN Entry Date May 29, 2008; 2-Thiophenecarboxylic acid, 5-methyl-3-[[4-[[[2-(1-piperazinyhphenyl]amino]carbonyl]-2-thiazolyl]amino]-, methyl ester.
CAS Registry No. 1023795-50-7; STN Entry Date May 30, 2008; 4-Thiazolecarboxamide, 2-[[3-(3,4-dichlorophenyl)-1-methyl-1H-pyrazol-5-yl]amino]-N-[2-(1-piperazinyl)phenyl]-.

(Continued)

*Primary Examiner* — Tracy Vivlemore
*Assistant Examiner* — Ebenezer O Sackey
(74) *Attorney, Agent, or Firm* — Kilpatrick Townsend & Stockton LLP

(57) ABSTRACT

The present invention relates compounds for stabilizing cells and methods of their use.

29 Claims, 35 Drawing Sheets

(56) References Cited

FOREIGN PATENT DOCUMENTS

| WO | 2007/109045 | | 9/2007 |
|---|---|---|---|
| WO | 2007/123269 | | 9/2007 |
| WO | 2008/003958 | | 1/2008 |
| WO | 2008/054701 | | 5/2008 |
| WO | 2009/054468 | | 4/2009 |
| WO | 2010/009155 | | 1/2010 |
| WO | 2010/012793 | | 2/2010 |
| WO | 2010065721 | A1 | 6/2010 |
| ZA | 201104019 | B | 11/2012 |
| ZA | 201206083 | B | 4/2014 |

OTHER PUBLICATIONS

CAS Registry No. 955426-27-4; STN Entry Date Nov. 22, 2007; 4-Piperidinecarboxamide, 1-[2-[[[2-(2-pyridinylamino)-4-thiazolyl]carbonyl]amino]phenyl]-.

CAS Registry No. 911000-72-1; STN Entry Date Oct. 20, 2006; 4-Thiazolecarboxamide, 2-[[5-[(2-chloro-5-methoxybenzoyl)amino]-2-pyrimidinyl]amino]-N-[2-(1-pyrrolidinyl)ethyl]-.

Greber et al., "Fibroblast Growth Factor 2 Modulates Transforming Growth Factor ß,Signaling in Mouse Embryonic Fibroblasts and Human ESCs (hESCs) to Support hESC Self-Renewal", Stem Cells, 2007, 25:455-464.

James et al., "TGFß,activin/nodal signaling is necessary for the maintenance of pluripotency in human embryonic stem cells", Development, 2005, 132:1273-1282.

Lu et al., "Defined culture conditions of human embryonic stem cells", PNAS, 2006, 103(15):5688-5693.

Ludwig et al., "Derivation of Human Embryonic Stem Cells in Defined Conditions", Nature Biotechnology, vol. 24(2), Feb. 2006, pp. 185-187.

Sato et al., "Maintenance of pluripotency in human and mouse embryonic stem", Nature Medicine, 2004, 10(1):55-63.

Thomson et al., "Embryonic Stem Cell Lines Derived from Human Blastocysts", Science, 1998, 282:1145-1147.

Thomson et al., "Human embryonic stem cell and embryonic germ cell lines", Tibtech, 2000, 18:53-57.

Wang, et al., "The Pharmacophore Hypothesis of Novel Inhibitors for Aurora A. Kinase", *Chinese Journal of Chemistry*, vol. 25 (12), pp. 1911-1918 (2007).

Xi, et al., "Synthesis and Evaluation of thiazole carboxamides as vanilloid receptor 1 (TRPV1) antogonists", *Biorganic & Medicinal Chemistry Letters*, vol. 15 (23), pp. 5211-5217 (2005).

Xu et al., "Basic FGF and suppression of BMP signaling sustain undifferentiated 0 proliferation of human ES cells", Nature Methods, 2005, 2(3):185-190.

Yao et al., "Long-term Self-renewal and Directed Differentiation of Human Embryonic Stem Cells in Chemically Defined Conditions", Proceedings of the National Academy of Sciences, vol. 103(18), May 2006, pp. 6907-6912.

U.S. Appl. No. 13/132,379, "Non Final Office Action", dated Aug. 1, 2013, 9 pages.

U.S. Appl. No. 13/132,379, "Notice of Allowance", dated Nov. 19, 2013, 7 Pages.

EP16174428.9, "Extended European Search Report", dated Oct. 6, 2016, 7 pages.

PCT/US2009/066554, "International Preliminary Report on Patentability", dated Jun. 7, 2011, 9 pages.

PCT/US2009/066554, "International Search Report", dated Apr. 14, 2010, 10 pages.

\* cited by examiner

METHODS OF ENHANCING CELL SURVIVAL OF STEM CELLS

CROSS-REFERENCES TO RELATED APPLICATIONS

This application is a continuation of U.S. application Ser. No. 15/863,501, filed Jan. 5, 2018, which is a a continuation of U.S. application Ser. No. 15/098,546, filed Apr. 14, 2016, now U.S. Pat. No. 9,896,655, which is a divisional of U.S. application Ser. No. 14/188,616, filed Feb. 24, 2014, now U.S. Pat. No. 9,340,525, which is a divisional of U.S. application Ser. No. 13/132,379, filed Jun. 2, 2011, now U.S. Pat. No. 8,691,573, which was filed under 35 U.S.C. § 371 from PCT Application No. PCT/US2009/066554, filed Dec. 3, 2009, which claims priority to U.S. Provisional Application No. 61/200,808, filed Dec. 3, 2008, each of which is incorporated in its entirety herein for all purposes.

BACKGROUND OF THE INVENTION

Embryonic stem cells (ESCs) are pluripotent cells that have the capacity to self-renew indefinitely and to differentiate into all cell types of the body (Thomson, J. A. et al., *Science* 282 (5391):1145-1147 (1998); Thomson, J. A. & Odorico, J. S., *Trends Biotechnol* 18 (2):53-57 (2000)). This ability provides hope that ESCs will one day be used to replace lost and damaged cells, and provide therapies beyond the reach of conventional drugs. However, to fully realize the clinical potentials of hESCs, chemically-defined, feeder- and animal product-free, robust culture conditions have to be established. Although several chemically-defined media have been reported (Yao, S. et al., *Proc Natl Acad Sci USA* 103 (18):6907-6912 (2006); Lu, J. et al., *Proc Natl Acad Sci USA* 103 (15):5688-5693 (2006); Ludwig, T. E. et al., *Nat Biotechnol* 24 (2):185-187 (2006)), they are still largely unsatisfactory due to the suboptimal performance of cells in them. Especially under these conditions, when cells are passaged by trypsin to single cells, they undergo extensive cell death. A number of signaling pathways that mediate hESC self-renewal are known, including FGF, TGF-β, Wnt, etc. (James, D. et al., *Development* 132 (6):1273-1282 (2005); Xu, R. H. et al., *Nat Methods* 2 (3):185-190 (2005); Beattie, G. M. et al., *Stem Cells* 23 (4):489-495 (2005); Greber, B., Lehrach, H., & Adjaye, J., *Stem Cells* 25 (2):455-464 (2007); Sato, N. et al., *Nat Med* 10 (1):55-63 (2004)). However, none of them appears to act as a survival factor in this process, the molecular mechanism of which being elusive.

BRIEF SUMMARY OF THE INVENTION

The present invention provides compounds having the formula:

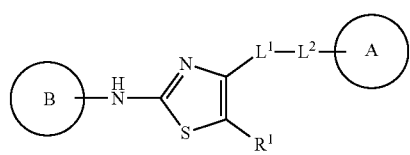

(I)

wherein
ring A is a substituted or unsubstituted cycloalkyl, substituted or unsubstituted heterocycloalkyl, substituted or unsubstituted aryl, or substituted or unsubstituted heteroaryl;
ring B is a substituted or unsubstituted heterocycloalkyl, or substituted or unsubstituted heteroaryl;
$L^1$ is —C(O)—$NR^2$— or —C(O)—$NR^2$—;
$L^2$ is a bond, substituted or unsubstituted alkylene or substituted or unsubstituted heteroalkylene; and
$R^1$ and $R^2$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In some embodiments, ring A is a substituted or unsubstituted aryl.

In some embodiments, ring A is a substituted or unsubstituted phenyl.

In some embodiments, ring B is a substituted or unsubstituted heterocycloalkyl, or substituted or unsubstituted heteroaryl.

In some embodiments, ring B is a substituted or unsubstituted heteroaryl.

In some embodiments, ring B is a substituted or unsubstituted pyrazolyl, substituted or unsubstituted furanyl, substituted or unsubstituted imidazolyl, substituted or unsubstituted isoxazolyl, substituted or unsubstituted oxadiazolyl, substituted or unsubstituted oxazolyl, substituted or unsubstituted pyrrolyl, substituted or unsubstituted pyridyl, substituted or unsubstituted pyrimidyl, substituted or unsubstituted pyridazinyl, substituted or unsubstituted thiazolyl, substituted or unsubstituted triazolyl, substituted or unsubstituted thienyl, substituted or unsubstituted dihydrothienopyrazolyl, substituted or unsubstituted thianaphthenyl, substituted or unsubstituted carbazolyl, substituted or unsubstituted benzothienyl, substituted or unsubstituted benzofuranyl, substituted or unsubstituted indolyl, substituted or unsubstituted quinolinyl, substituted or unsubstituted benzotriazolyl, substituted or unsubstituted benzothiazolyl, substituted or unsubstituted benzooxazolyl, substituted or unsubstituted benzimidazolyl, substituted or unsubstituted isoquinolinyl, substituted or unsubstituted isoindolyl, substituted or unsubstituted acridinyl, substituted or unsubstituted benzoisazolyl, or substituted or unsubstituted dimethylhydantoin.

In some embodiments, $L^2$ is substituted or unsubstituted $C_1$-$C_{10}$ alkyl.

In some embodiments, $L^2$ is unsubstituted $C_1$-$C_{10}$ alkyl.

In some embodiments, $L^2$ is methylene.

In some embodiments, ring A is substituted or unsubstituted aryl; ring B is substituted or unsubstituted heteroaryl; $R^1$ is hydrogen; and $L^2$ is unsubstituted $C_1$-$C_{10}$ alkyl.

In some embodiments, $R^2$ is hydrogen.

In some embodiments, $R^1$ is hydrogen or unsubstituted $C_1$-$C_{10}$ alkyl.

In some embodiments, $R^1$ is hydrogen.

In some embodiments, the compound has the formula:

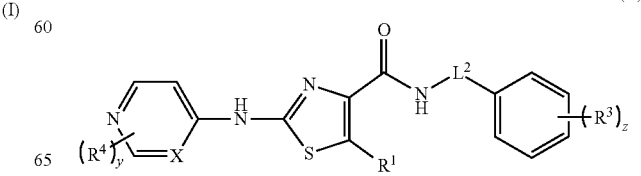

(II)

wherein, y is an integer from 0 to 3; z is an integer from 0 to 5; X is —N═, —CH═ or —CR$^5$═; R$^3$, R$^4$ and R$^5$ are independently CN, S(O)nR$^6$, NR$^7$R$^8$, C(O)R$^9$, NR$^{10}$—C(O)R$^{11}$, NR$^{12}$—C(O)—OR$^{13}$, —C(O)NR$^{14}$R$^{15}$, —NR$^{16}$S(O)$_2$R$^{17}$, —OR$^{18}$, —S(O)$_2$NR$^{19}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein n is an integer from 0 to 2, wherein if z is greater than 1, two R$^3$ moieties are optionally joined together to form a substituted or unsubstituted cycloalkyl, substituted or unsubstituted heterocycloalkyl, substituted or unsubstituted aryl, or substituted or unsubstituted heteroaryl; and R$^6$, R$^7$, R$^8$, R$^9$, R$^{10}$, R$^{11}$, R$^{12}$, R$^{13}$, R$^{14}$, R$^{15}$, R$^{16}$, R$^{17}$, R$^{18}$ and R$^{19}$ are independently hydrogen, substituted or unsubstituted alkyl, substituted or unsubstituted heteroalkyl, unsubstituted cycloalkyl, substituted or unsubstituted heterocycloalkyl, substituted or unsubstituted aryl, or substituted or unsubstituted heteroaryl.

In some embodiments, L$^2$ is substituted or unsubstituted C$_1$-C$_{10}$ alkyl.

In some embodiments, L$^2$ is unsubstituted C$_1$-C$_{10}$ alkyl.

In some embodiments, L$^2$ is methylene.

In some embodiments, X is —N═ or —CH═.

In some embodiments, z is 2 and two R$^3$ moieties at adjacent vertices are joined together to from a substituted or unsubstituted heterocycloalkyl.

In some embodiments, z is 1.

In some embodiments, y is 0 or 1.

In some embodiments, R$^3$ is —OR$^{18}$, and R$^{18}$ is hydrogen or unsubstituted C$_1$-C$_{10}$ alkyl.

In some embodiments, L$^2$ is methylene; X is —N═ or —CH═; R$^1$ is hydrogen; and y and z are 0.

In some embodiments, the compound has the formula:

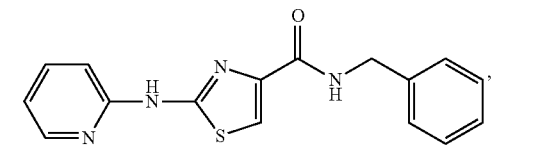

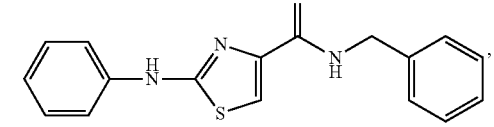

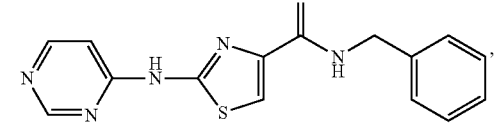

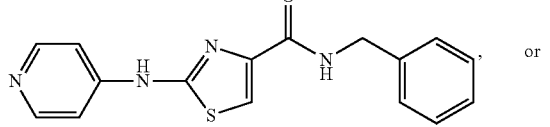

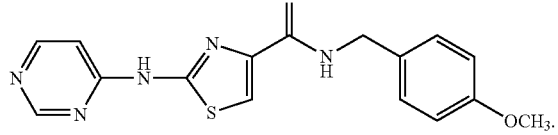

The present invention also provides for compounds having the formula:

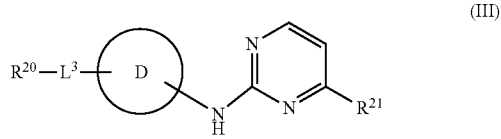

(III)

wherein

Ring D is substituted or unsubstituted aryl or substituted or unsubstituted heteroaryl;

L$^3$ is —C(O)NH— or —S(O)$_2$NH—;

R$^{20}$ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{21}$ is —NR$^{22}$R$^{23}$ or —OR$^{24}$;

R$^{22}$ and R$^{23}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or joined together to form a substituted or unsubstituted heterocycloalkyl or substituted or unsubstituted heteroaryl;

R$^{24}$ is substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or joined together to form a substituted or unsubstituted cycloalkyl of substituted or unsubstituted heterocycloalkyl.

In some embodiments, ring D is substituted or unsubstituted phenyl.

In some embodiments, R$^{20}$ is substituted or unsubstituted alkyl or substituted or unsubstituted cycloalkyl.

In some embodiments, R$^{20}$ is substituted or unsubstituted C$^1$-C$^{10}$ alkyl or substituted or unsubstituted 3 to 7 membered cycloalkyl.

In some embodiments, R$^{20}$ is substituted or unsubstituted C$^1$-C$^5$ alkyl or substituted or unsubstituted 3 to 6 membered cycloalkyl.

In some embodiments, R$^{20}$ is unsubstituted C$^1$-C$^5$ alkyl or unsubstituted 3 to 6 membered cycloalkyl.

In some embodiments, R$^{22}$ is hydrogen; and R$^{23}$ is substituted or unsubstituted cycloalkyl, substituted or unsubstituted heterocycloalkyl, substituted or unsubstituted aryl, or substituted or unsubstituted heteroaryl.

In some embodiments, R$^{22}$ is hydrogen; and R$^{23}$ is substituted or unsubstituted substituted or unsubstituted aryl.

In some embodiments, R$^{22}$ and R$^{23}$ are joined together to from a substituted or unsubstituted heterocycloalkyl, or substituted or unsubstituted heteroaryl.

In some embodiments, R$^{22}$ and R$^{23}$ are joined together to from a substituted or unsubstituted pyrrolyl, substituted or unsubstituted isoindolinyl, substituted or unsubstituted piperidinyl, or substituted or unsubstituted tetrahydroquinolinyl.

In some embodiments, compound has the formula

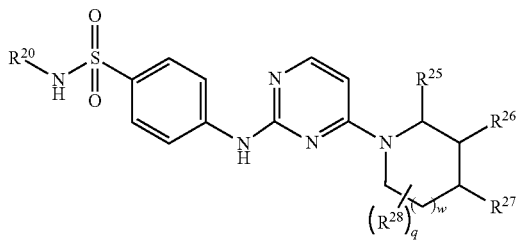

wherein, w is an integer from 0 to 1; q is an integer from 0 to 7; $R^{25}$, $R^{26}$, $R^{27}$ and $R^{28}$ are independently —CN, —$NR^{29}R^{30}$, —$C(O)R^{31}$, —$NR^{32}$—$C(O)R^{33}$, —$NR^{34}$—C(O)—$OR^{35}$, —$C(O)NR^{36}R^{37}$, —$NR^{38}S(O)_2R^{39}$, —$OR^{40}$, —$S(O)_2NR^{41}$, —$S(O)_vR^{42}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein v is an integer from 0 to 2; $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, and $R^{42}$ are independently hydrogen, substituted or unsubstituted alkyl, substituted or unsubstituted heteroalkyl, unsubstituted cycloalkyl, substituted or unsubstituted heterocycloalkyl, substituted or unsubstituted aryl, or substituted or unsubstituted heteroaryl, wherein $R^{25}$ and $R^{26}$, or $R^{26}$ and $R^{27}$, may be joined to form a substituted or unsubstituted cycloalkyl, substituted or unsubstituted heterocycloalkyl, substituted or unsubstituted aryl, or substituted or unsubstituted heteroaryl.

In some embodiments, $R^{28}$ is —$OR^{40}$, wherein $R^{40}$ is hydrogen or unsubstituted $C_1$-$C_{10}$ alkyl.

In some embodiments, $R^{40}$ is hydrogen or unsubstituted $C_1$ to $C_5$ alkyl.

In some embodiments, the compound has the formula:

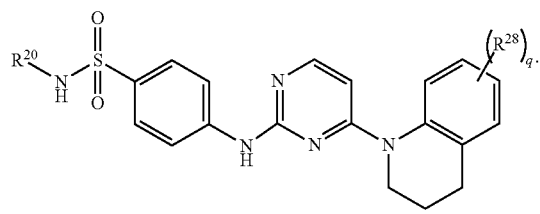

In some embodiments, $R^{20}$ is unsubstituted $C_1$ to $C_{10}$ alkyl.

In some embodiments, $R^{28}$ is —$OR^{40}$, wherein $R^{40}$ is hydrogen or unsubstituted $C_1$ to $C_{10}$ alkyl, or $C_1$ to $C_{10}$ alkyl substituted with substituted or unsubstituted $C_3$ to $C_6$ cycloalkyl.

In some embodiments, q is 1.

In some embodiments, the compound has the formula:

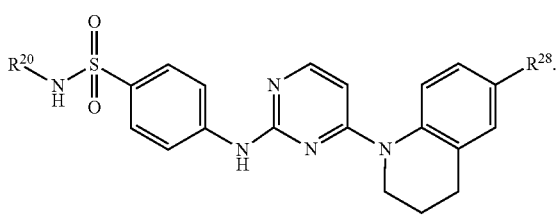

In some embodiments, the compounds have the formula:

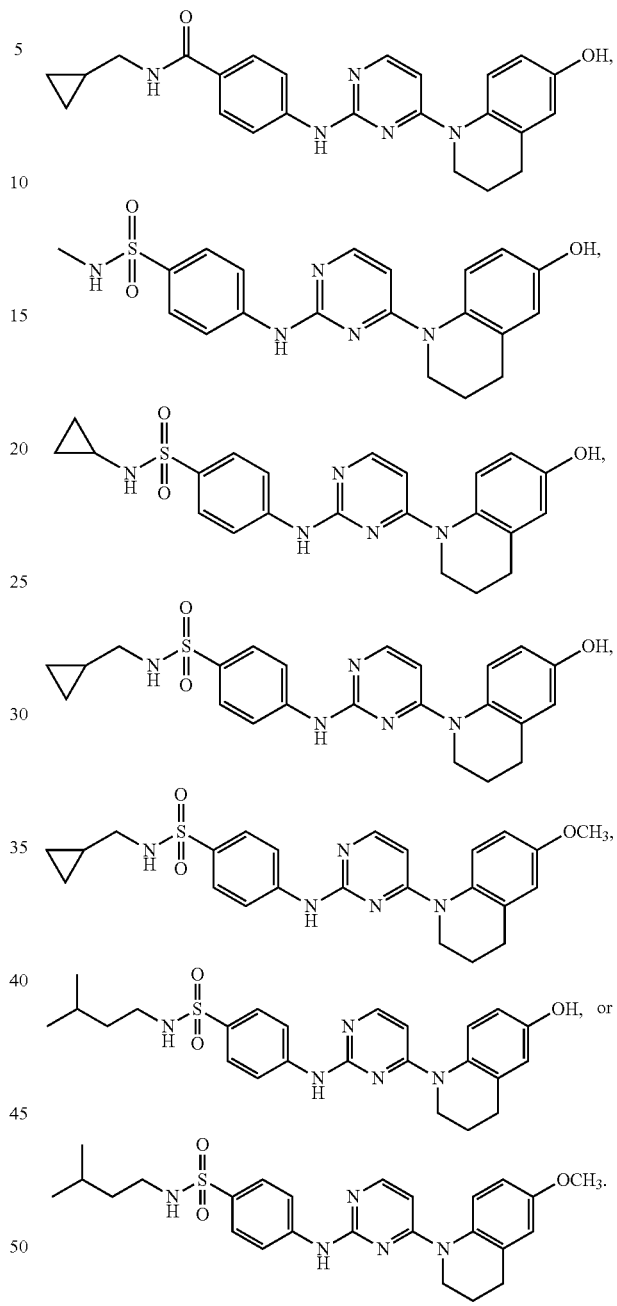

The present invention also provides methods of stabilizing an isolated cell in vitro. In some embodiments, the method comprises contacting an animal cell with a sufficient amount of a compound of formula I or III to stabilize the cell.

In some embodiments, the method further comprises changing the conditions or environment of the cell in the presence of the compound, wherein the changing step in the absence of the compound would result in a change in the cell's cellular programming. In some embodiments, the changing step comprises at least one of thawing the cells and dissociating the cells from other cell.

In some embodiments, the cell is adherent. In some embodiments, the cell is in suspension.

In some embodiments, the method further comprises determining a phenotype of the cell.

In some embodiments, the method comprises isolating the cells from an animal. In some embodiments, the animal is a human. In some embodiments, the animal is a non-human animal.

In some embodiments, the compound is a compound of formula I. In some embodiments, the compound is a compound of formula III.

The present invention also provides methods of ameliorating a condition in an animal. In some embodiments, the method comprises administering a sufficient amount of a compound of formula I or III to an animal in need thereof to ameliorate the condition.

In some embodiments, the condition is selected from the group consisting of tissue damage, stroke, and cancer. In some embodiments, the tissue is selected from the group consisting of pancreas, liver, intestine, lung, and kidney.

In some embodiments, the condition comprises at least partial rejection of a transplanted tissue or organ. In some embodiments, the transplantation comprises transplantation of bone marrow, cord blood, purified hematopoietic stem or progenitor cells, cardiac cells, neural cells, pancreatic beta cells, or liver cells.

In some embodiments, the compound is a compound of formula I. In some embodiments, the compound is a compound of formula III.

The present invention also provides methods for maintaining cell survival. In some embodiments, the method comprises generating isolated stem cells, progenitor cells, or differentiated cells; and inducing stabilization of E-cadherin in the isolated cells, thereby maintaining cell survival.

In some embodiments, the inducing step comprises contacting the isolated stem cell with an amount of a compound of formula I sufficient to improve survival of isolated stem cells by at least 2-fold compared to the absence of the compound.

In some embodiments, the inducing step comprises culturing the isolated stem cells on a surface, wherein a molecule comprising an E-Cadherin ectodomain is tethered to the surface.

The present invention also provides populations of isolated cells comprising an amount of a molecule that stabilizes E-cadherin in the cells sufficient to improve survival of isolated cells by at least 2-fold compared to the absence of the molecule.

In some embodiments, the molecule comprises a compound of formula I.

In some embodiments, the cells are selected from the group consisting of stem cells, induced stem cells, pluripotent stem cells, progenitor cells, differentiated cells, beta cells and fibroblasts.

The present invention also provides for populations of isolated cells comprising an amount of a compound of formula I or III sufficient to improve survival of isolated cells by at least 2-fold compared to the absence of the compound.

In some embodiments, the cells are selected from the group consisting of stem cells, induced stem cells, pluripotent stem cells, progenitor cells, differentiated cells, beta cells and fibroblasts.

The present invention also provides methods for maintaining stem cell survival. In some embodiments, the methods comprise generating isolated cells; and activating protein kinase C (PKC) in the isolated cells, thereby maintaining cell survival.

In some embodiments, the activating step comprises contacting a sufficient amount of phorbol 12-myristate 13-acetate (PMA) to the isolated cells to improve survival of the cells compared to the survival rate in the absence of PMA.

The present invention also provides populations of isolated stem cells comprising an amount of protein kinase C activator sufficient to improve survival of isolated stem cells by at least 2-fold compared to the absence of the PKC activator.

Definitions

The abbreviations used herein have their conventional meaning within the chemical and biological arts.

The term "stabilizing a cell" refers to substantially reducing or eliminating the response of a cell to a change in the conditions or environment to which the cell is exposed. "Substantially reducing" in this context means that the response is at least 50% less than what would have occurred in the absence of a stabilizing component (e.g., the compounds of the invention).

The term "changing the conditions or environment of a cell" refers to changing the temperature, culture media (e.g., carbon source, salt concentration, growth factor), dissociating the cells into isolated cells, thawing cells, or otherwise changing a factor of a cell's immediate environment. As discussed herein, changing the condition or environment of a cell will often change the cell's phenotype or cellular programming. For example, stem cells, as well as some other cells, when isolated will differentiate and/or die in response to certain changes such as isolation, thawing, etc. Thus, changing conditions can reduce or eliminate cell viability whereas stabilized cells as described herein do not have substantially reduced viability under the same changes of condition. Change in cell programming can also be monitored as a cell's response to a specific stimulus that is characteristic for a certain cell type and/or as by expression of one or a set of characteristic genes or gene products. As a non-limiting example, human pluripotent stem cells are known to express at least some, and optionally all, of the markers from the following list: SSEA-3, SSEA-4, TRA-1-60, TRA-1-81, TRA-2-49/6E, ALP, Sox2, E-cadherin, UTF-1, Oct4, Rexl, and Nanog. Such expression may change as a stem cell loses pluripotency or otherwise differentiates. A stabilized human pluripotent stem cell would maintain its characteristic expression pattern following a change in condition.

An "isolated" cell has been substantially separated or purified away from other cells of an organism.

The term "dissociating" cells refers to a process of isolating cells from other cells or from a surface (e.g., a culture plate surface). For example, cells can be dissociated from an animal or tissue by mechanical or enzymatic methods. Alternatively, cells that aggregate in vitro can be dissociated from each other. In yet another alternative, adherent cells are dissociated from a culture plate or other surface. Dissociation thus can involve breaking cell interactions with extracellular matrix (ECM) and substrates (e.g., culture surfaces) or breaking the ECM between cells.

"Determining a phenotype of a cell" refers to assessing a quality or characteristic of the cell. Phenotypes can include, for example, cell type-characteristic gene expression, or gene expression patterns, response of the cell to a stimulus or environment, ability to differentiate or de-differentiate, have a particular morphology, etc.

Where chemical substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e. unbranched) or branched chain, or combination thereof, which may be fully saturated, mono- or polyunsaturated and can include di- and multivalent radicals, having the number of carbon atoms designated (i.e. C$_1$-C$_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. Preferred alkyl groups are C$_{1-6}$ alkyl groups.

The term "alkylene" by itself or as part of another substituent means a divalent radical derived from an alkyl, as exemplified, but not limited, by —CH$_2$CH$_2$CH$_2$CH$_2$—. Typically, an alkyl (or alkylene) group will have from 1 to 24 carbon atoms, with those groups having 10 or fewer carbon atoms being exemplified in the present invention. A "lower alkyl" or "lower alkylene" is a shorter chain alkyl or alkylene group, generally having eight or fewer carbon atoms. Preferred alkylene groups are C$_{1-6}$ alkylene groups.

The term "heteroalkyl," by itself or in combination with another term, means, unless otherwise stated, a stable straight or branched chain, or cyclic hydrocarbon radical, or combinations thereof, consisting of at least one carbon atoms and at least one heteroatom selected from the group consisting of O, N, P, Si and S, and wherein the nitrogen and sulfur atoms may optionally be oxidized and the nitrogen heteroatom may optionally be quaternized. The heteroatom(s) O, N, P and S and Si may be placed at any interior position of the heteroalkyl group or at the position at which the alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, O—CH$_3$, —O—CH$_2$—CH$_3$, and —CN. Up to two heteroatoms may be consecutive, such as, for example, —CH$_2$—NH—OCH$_3$ and —CH$_2$—O—Si(CH$_3$)$_3$. Similarly, the term "heteroalkylene" by itself or as part of another substituent means a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like. Preferred heteroalkyl groups are C$_{1-6}$ heteroalkyl groups.

As used herein, the term "heteroalkylene" refers to a heteroalkyl group, as defined above, linking at least two other groups. The two moieties linked to the heteroalkylene can be linked to the same atom or different atoms of the heteroalkylene. Preferred heteroalkylene groups are C$_{1-6}$ heteroalkylene groups.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and "heterocycloalkylene" refer to a divalent radical derived from cycloalkyl and heterocycloalkyl, respectively. Cycloalkyl and heterocycloalkyl groups can be C$_{3-8}$ cycloalkyl and C$_{3-8}$ heterocycloalkyl groups, or C$_{5-8}$ cycloalkyl and C$_{5-8}$ heterocycloalkyl groups The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo(C$_1$-C$_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, hydrocarbon substituent which can be a single ring or multiple rings (preferably from 1 to 3 rings) which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. "Arylene" and "heteroarylene" refers to a divalent radical derived from a aryl and heteroaryl, respectively. Aryl groups of the present invention preferably have 5-12 ring members, more preferably 6-10 ring members. Heteroryl groups of the present invention preferably have 5-12 ring members, more preferably 5-10 ring members.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

The term "oxo" as used herein means an oxygen that is double bonded to a carbon atom.

The term "alkylsulfonyl" as used herein means a moiety having the formula —S(O2)-R', where R' is an alkyl group as defined above. R' may have a specified number of carbons (e.g. "$C_1$-$C_4$ alkylsulfonyl").

Each of the above terms (e.g., "alkyl," "heteroalkyl," "aryl" and "heteroaryl") are meant to include both substituted and unsubstituted forms of the indicated radical. Exemplary substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NR—C(NR'R"R''')=NR'''', —NR—C(NR'R")=NR''', —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R''' and R'''' each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy or thioalkoxy groups, or arylalkyl groups. When a compound of the invention includes more than one R group, for example, each of the R groups is independently selected as are each R', R", R''' and R'''' groups when more than one of these groups is present. When R' and R" are attached to the same nitrogen atom, they can be combined with the nitrogen atom to form a 4-, 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: halogen, —OR', —NR'R", —SR', -halogen, —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NR—C(NR'R"R''')=NR'''', —NR—C(NR'R")=NR''', —S(O)R', —S(O)$_2$R', —S(O)$_2$NR'R", —NRSO$_2$R', —CN and —NO$_2$, —R', —N$_3$, —CH(Ph)$_2$, fluoro($C_1$-$C_4$)alkoxy, and fluoro ($C_1$-$C_4$)alkyl, in a number ranging from zero to the total number of open valences on the aromatic ring system; and where R', R", R''' and R'''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound of the invention includes more than one R group, for example, each of the R groups is independently selected as are each R', R", R''' and R'''' groups when more than one of these groups is present.

Two of the substituents on adjacent atoms of the aryl or heteroaryl ring may optionally form a ring of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R''')$_d$—, where s and d are independently integers of from 0 to 3, and X' is —O—, —NR'—, —S—, —S(O)—, —S(O)$_2$—, or —S(O)$_2$NR'—. The substituents R, R', R" and R''' are preferably independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the term "heteroatom" or "ring heteroatom" is meant to include oxygen (O), nitrogen (N), sulfur (S), phosphorus (P), and silicon (Si).

A "substituent group," as used herein, means a group selected from the following moieties:

(A) —OH, —NH$_2$, —SH, —CN, —CF$_3$, —NO$_2$, Oxo, halogen, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from:

(i) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, and heteroaryl, substituted with at least one substituent selected from:

(a) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, or heteroaryl, substituted with at least one substituent selected from oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, and unsubstituted heteroaryl.

A "size-limited substituent" or "size-limited substituent group," as used herein means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_4$-$C_8$ cycloalkyl, and each substituted or unsubstituted heterocycloalkyl is a substituted or unsubstituted 4 to 8 membered heterocycloalkyl.

A "lower substituent" or "lower substituent group," as used herein means a group selected from all of the substituents described above for a "substituent group," wherein each substituted or unsubstituted alkyl is a substituted or unsubstituted $C_1$-$C_5$ alkyl, each substituted or unsubstituted heteroalkyl is a substituted or unsubstituted 2 to 8 membered heteroalkyl, each substituted or unsubstituted cycloalkyl is a substituted or unsubstituted $C_5$-$C_7$ cycloalkyl, and each substituted or unsubstituted heterocycloalkyl is a substituted or unsubstituted 5 to 7 membered heterocycloalkyl.

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science*, 1977, 66, 1-19). Certain specific compounds of the present invention contain both basic and acidic functionalities that allow the compounds to be converted into either base or acid addition salts.

Thus, the compounds of the present invention may exist as salts with pharmaceutically acceptable acids. The present invention includes such salts. Examples of such salts include hydrochlorides, hydrobromides, sulfates, methanesulfonates, nitrates, maleates, acetates, citrates, fumarates, tartrates (eg (+)-tartrates, (−)-tartrates or mixtures thereof including racemic mixtures, succinates, benzoates and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, tautomers, geometric isomers and individual isomers are encompassed within the scope of the present invention. The compounds of the present invention do not include those which are known in the art to be too unstable to synthesize and/or isolate.

The compounds of the present invention may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds of the present invention, whether radioactive or not, are encompassed within the scope of the present invention.

BRIEF DESCRIPTION OF THE DRAWINGS

FIGS. 6A, 6B, 6C, 6D, 6E, 6F, 6G, 6H, 6I, 6J, 6K, 6L, 6M, 6N, 6O, 6P, 6Q, 6R, 6S, 6T, 6U, 6V, 6W, 6X, 6Y, 6Z, 6AA, 6AB and 6AC show compounds of the present invention, including pyrintegrin and derivatives thereof.

DETAILED DESCRIPTION

I. Introduction

Figure 1:
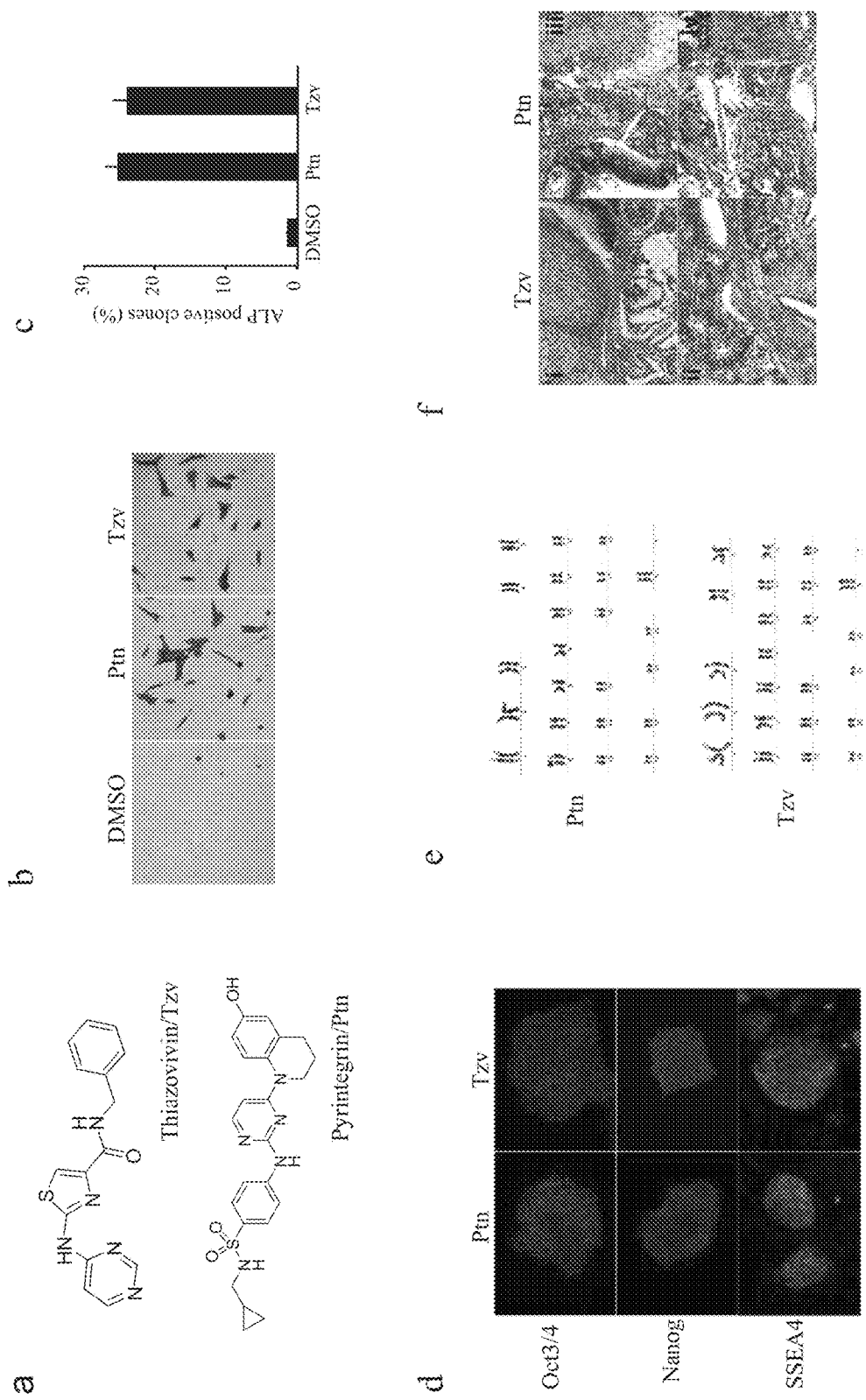
FIG. 1. Novel synthetic small molecules dramatically increase hESC survival after single cell dissociation without compromising their long-term self-renewal and full developmental potential. (a) Chemical structures of Thiazovivin/Tzv and Pyrintegrin/Ptn as indicated. (b) ALP staining of hESC colonies that had grown from dissociated single cells seeded in low density and treated as indicated. (c) Ratio of ALP positive colonies vs. total initially seeded cells. (d) Immunostaining of hESCs long-term maintained in media containing Ptn or Tzv as indicated. (e) Sections of 5 weeks teratomas formed from long-term expanded hESCs maintained in media containing Tzv (i, ii) or Ptn (iii, iv). Neuroepithelium (ectoderm), cartilage (mesoderm), and simple epithelium (endoderm) (i); neuroepithelium (ectoderm), simple epithelium and hepatic-type epithelium (endoderm) (ii); neuroepithelium (ectoderm), cartilage (mesoderm) and tubular epithelium (endoderm) (iii); neuroepithelium (ectoderm), skeletal muscle (mesoderm), and tubular epithelium (endoderm) (iv). (f) G-banding analysis of hESCs after more than 20 passages, propagated in the presence of compounds Ptn or Tzv. If not specified, all the above hESCs were grown in the chemically-defined medium and feeder-free on the Matrigel-coated plates.

The present invention provides novel compounds as well as methods for their use. Two classes of small molecule chemical compounds are provided that prevent differentiation of cells and promote cell survival, including but not limited to, when the cells are isolated or are otherwise outside their normal medium or tissue milieu. The compounds work by somewhat different mechanisms but both are useful as prophylactic and therapeutic compounds for a number of different disease indications, including but not limited to, cancer, tissue damage, and stroke.

II. Compounds that Promote Cell Survival and/or Anti-Differentiation

In one aspect, compounds that promote cell survival and/or anti-differentiation are provided. In some embodiments, the compound has the formula:

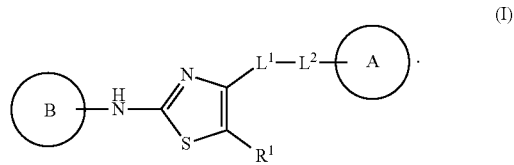

(I)

In Formula (I), ring A is a substituted or unsubstituted cycloalkyl, substituted or unsubstituted heterocycloalkyl, substituted or unsubstituted aryl, or substituted or unsubstituted heteroaryl. Ring B is a substituted or unsubstituted heterocycloalkyl, or substituted or unsubstituted heteroaryl.

$L^1$ is —C(O)—NR²— or —NR²—C(O)—. $L^2$ is a bond, substituted or unsubstituted alkylene or substituted or unsubstituted heteroalkylene.

$R^1$ and $R^2$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In some embodiments, ring A is a substituted or unsubstituted aryl. Ring A may also be a substituted or unsubstituted phenyl.

In other embodiments, ring B is a substituted or unsubstituted heterocycloalkyl, or substituted or unsubstituted heteroaryl. Ring B may also be a substituted or unsubstituted heteroaryl. In still other embodiments, ring B is a substituted or unsubstituted pyrazolyl, substituted or unsubstituted furanyl, substituted or unsubstituted imidazolyl, substituted or unsubstituted isoxazolyl, substituted or unsubstituted oxadiazolyl, substituted or unsubstituted oxazolyl, substituted or unsubstituted pyrrolyl, substituted or unsubstituted pyridyl, substituted or unsubstituted pyrimidyl, substituted or unsubstituted pyridazinyl, substituted or unsubstituted thiazolyl, substituted or unsubstituted triazolyl, substituted or unsubstituted thienyl, substituted or unsubstituted dihydrothieno-pyrazolyl, substituted or unsubstituted thianaphthenyl, substituted or unsubstituted carbazolyl, substituted or unsubstituted benzothienyl, substituted or unsubstituted benzofuranyl, substituted or unsubstituted indolyl, substituted or unsubstituted quinolinyl, substituted or unsubstituted benzotriazolyl, substituted or unsubstituted benzothiazolyl, substituted or unsubstituted benzooxazolyl, substituted or unsubstituted benzimidazolyl, substituted or unsubstituted isoquinolinyl, substituted or unsubstituted isoindolyl, substituted or unsubstituted acridinyl, substituted or unsubstituted benzoisazolyl, or substituted or unsubstituted dimethylhydantoin.

$L^2$ may be substituted or unsubstituted $C_1$-$C_{10}$ alkyl. In some embodiments, $L^2$ is unsubstituted $C_1$-$C_{10}$ alkyl. $L^2$ may also be substituted or unsubstituted methylene (e.g. unsubstituted methylene).

$R^2$ may be hydrogen. $R^1$ may be hydrogen or unsubstituted $C_1$-$C_{10}$ alkyl. In some embodiments, $R^1$ is simply hydrogen.

In some embodiments of Formula (I), ring A is substituted or unsubstituted aryl, ring B is substituted or unsubstituted heteroaryl, $R^1$ is hydrogen, and $L^2$ is unsubstituted $C_1$-$C_{10}$ alkyl.

In another embodiment, the compound that promote cell survival and/or anti-differentiation has the formula:

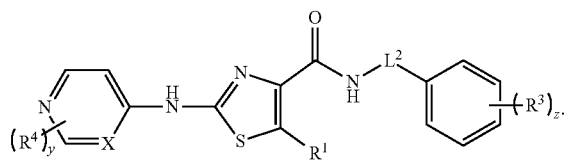

(II)

In Formula (II), y is an integer from 0 to 3 and z is an integer from 0 to 5. X is —N=, —CH= or —CR$^5$=. $R^1$ and $L^2$ are as defined above in the definitions of Formula (I).

$R^3$, $R^4$ and $R^5$ are independently —CN, —S(O)$_n$R$^6$, —NR$^7$R$^8$, —C(O)R$^9$, —NR$^{10}$—C(O)R$^{11}$, —NR$^{12}$—C(O)—OR$^{13}$, —C(O)NR$^{14}$R$^{15}$, —NR$^{16}$S(O)$_2$R$^{17}$, —OR$^{18}$, —S(O)$_2$NR$^{19}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein n is an integer from 0 to 2, wherein if z is greater than 1, two $R^3$ moieties are optionally joined together to form a substituted or unsubstituted cycloalkyl, substituted or unsubstituted heterocycloalkyl, substituted or unsubstituted aryl, or substituted or unsubstituted heteroaryl.

$R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$ and $R^{19}$ are independently hydrogen, substituted or unsubstituted alkyl, substituted or unsubstituted heteroalkyl, unsubstituted cycloalkyl, substituted or unsubstituted heterocycloalkyl, substituted or unsubstituted aryl, or substituted or unsubstituted heteroaryl.

In some embodiments, $L^2$ is substituted or unsubstituted $C_1$-$C_{10}$ alkyl. $L^2$ may also be substituted $C_1$-$C_{10}$ alkyl. Alternatively, $L^2$ is substituted or unsubstituted methylene (e.g. unsubstituted methylene).

In other embodiments, X is —N= or —CH=. The symbol z may be 2. In still other embodiments, two $R^3$ moieties at adjacent vertices are joined together to from a substituted or unsubstituted heterocycloalkyl. The symbol z may also be 1. The symbol y may be 0 or 1.

$R^3$ may be —OR$^{18}$. $R^{18}$ may be hydrogen or unsubstituted $C_1$-$C_{10}$ alkyl.

In some embodiments, $L^2$ is substituted or unsubsituted methylene (e.g. substituted methylene), X is —N= or —CH=, $R^1$ is hydrogen, and y and z are 0.

In other embodiments, the compounds has the formula:

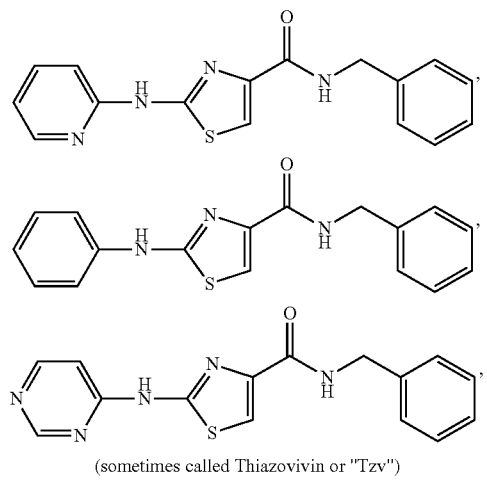

(sometimes called Thiazovivin or "Tzv")

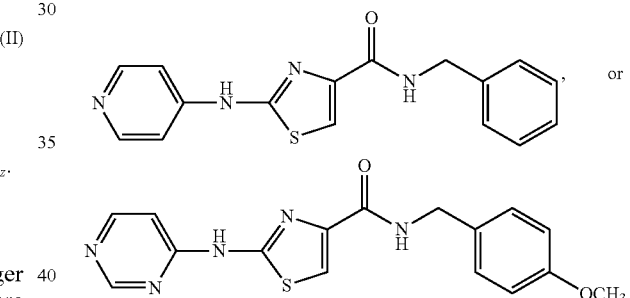

In still other embodiments, the compounds of formula I are those where ring A is cycloalkyl, heterocycloalkyl, aryl, or heteroaryl, each optionally substituted with 1-5 $R^3$ groups; ring B is heterocycloalkyl or heteroaryl, each optionally substituted with 1-5 $R^4$ groups; $L^1$ is —C(O)—NR$^2$— or —NR$^2$—C(O)—; $L^2$ is a bond, $C_{1-10}$ alkylene or $C_{1-10}$ heteroalkylene; $R^1$ and $R^2$ are independently hydrogen, $C_{1-10}$ alkyl, $C_{1-10}$ heteroalkyl, $C_{3-8}$ cycloalkyl, $C_{3-8}$ heterocycloalkyl, aryl, or heteroaryl; each $R^3$ and $R^4$ is independently —CN, —S(O)$_n$R$^6$, —NR$^7$R$^8$, —C(O)R$^9$, —NR$^{10}$—C(O)R", —NR$^{12}$—C(O)—OR$^{13}$, —C(O)NR$^{14}$R$^{15}$, —NR$^{16}$S(O)$_2$R$^{17}$, —OR$^{18}$, —S(O)$_2$NR$^{19}$, $C_{1-10}$ alkyl, $C_{1-10}$ heteroalkyl, cycloalkyl, heterocycloalkyl, aryl, or heteroaryl, wherein n is an integer from 0 to 2, wherein two $R^3$ moieties are optionally joined together to form a cycloalkyl, heterocycloalkyl, aryl, or heteroaryl; and $R^6$, $R^7$, $R^8$, $R^9$, $R^{10}$, $R^{11}$, $R^{12}$, $R^{13}$, $R^{14}$, $R^5$, $R^{16}$, $R^{17}$, $R^{18}$ and $R^{19}$ are each independently hydrogen, $C_{1-10}$ alkyl, $C_{1-10}$ heteroalkyl, cycloalkyl, heterocycloalkyl, aryl, or heteroaryl. In still yet other embodiments, the compounds of formula I are other than Thiazovivin.

In other embodiments, the compound that promote cell survival and/or anti-differentiation has the formula:

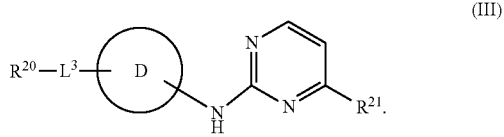

(III)

In Formula (III), ring D is substituted or unsubstituted aryl or substituted or unsubstituted heteroaryl. $L^3$ is —C(O)NH— or —S(O)$_2$NH—.

$R^{20}$ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{21}$ is —NR$^{22}$R$^{23}$ or —OR$^{24}$.

$R^{22}$ and $R^{23}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or joined together to form a substituted or unsubstituted heterocycloalkyl or substituted or unsubstituted heteroaryl.

$R^{24}$ is substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or joined together to form a substituted or unsubstituted cycloalkyl of substituted or unsubstituted heterocycloalkyl.

In other embodiments, $L^3$ is a bond, —O—, —C(O)NH— or —S(O)$_2$NH—, $R^{20}$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, and Ring D and $R^{21}$ are as defined above. In some other embodiments, $L^3$ is a bond, —O— or —S(O)$_2$NH—, and Ring D, $R^{20}$ and $R^{21}$ are as defined above, such that when $L^3$ is —S(O)$_2$NH—, $R^{20}$ is hydrogen. In still other embodiments, $L^3$ is a bond or —O—, and Ring D, $R^{20}$ and $R^{21}$ are as defined above.

In some embodiments, ring D is substituted or unsubstituted phenyl.

In other embodiments, $R^{20}$ is substituted or unsubstituted alkyl or substituted or unsubstituted cycloalkyl. $R^{20}$ may be substituted or unsubstituted $C_1$-$C_{10}$ alkyl or substituted or unsubstituted 3 to 7 membered cycloalkyl. $R^{20}$ may also be substituted or unsubstituted $C_1$-$C_5$ alkyl or substituted or unsubstituted 3 to 6 membered cycloalkyl. In some embodiments, $R^{20}$ is unsubstituted $C_1$-$C_5$ alkyl or unsubstituted 3 to 6 membered cycloalkyl.

In still other embodiments, $R^{22}$ is hydrogen, and $R^{23}$ is substituted or unsubstituted cycloalkyl, substituted or unsubstituted heterocycloalkyl, substituted or unsubstituted aryl, or substituted or unsubstituted heteroaryl. Alternatively, $R^{22}$ is hydrogen; and $R^{23}$ is substituted or unsubstituted substituted or unsubstituted aryl. Or $R^{22}$ and $R^{23}$ are joined together to from a substituted or unsubstituted heterocycloalkyl, or substituted or unsubstituted heteroaryl. $R^{22}$ and $R^{23}$ may also be joined together to from a substituted or unsubstituted pyrrolyl, substituted or unsubstituted isoindolinyl, substituted or unsubstituted piperidinyl, or substituted or unsubstituted tetrahydroquinolinyl.

In some embodiments, the compound has the formula:

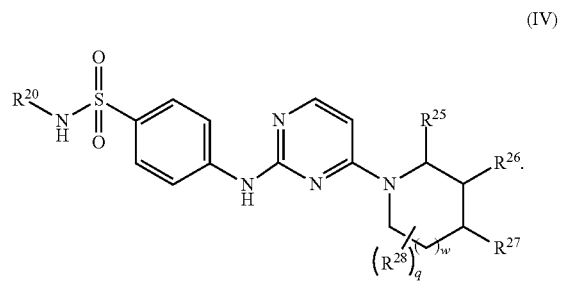

(IV)

In Formula (IV), w is an integer from 0 to 1 and q is an integer from 0 to 7. $R^{20}$ is as defined above in the definition of the compound of Formula (III). $R^{25}$, $R^{26}$, $R^{27}$ and $R^{28}$ are independently —CN, —NR$^{29}$R$^{30}$, —C(O)R$^{31}$, —NR$^{32}$—C(O)R$^{33}$, —NR$^{34}$—C(O)—OR$^{35}$, —C(O)NR$^{36}$R$^{37}$, —NR$^{38}$S(O)$_2$R$^{39}$, —OR$^{40}$, —S(O)$_2$NR$^{41}$, —S(O)$_v$R$^{42}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein v is an integer from 0 to 2.

$R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, and $R^{42}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^{25}$ and $R^{26}$, or $R^{26}$ and $R^{27}$, may be joined to form a substituted or unsubstituted cycloalkyl, substituted or unsubstituted heterocycloalkyl, substituted or unsubstituted aryl, or substituted or unsubstituted heteroaryl.

In some embodiments, $R^{28}$ is —OR$^{40}$. $R^{40}$ is hydrogen or unsubstituted $C_1$-$C_{10}$ alkyl $R^{40}$ may also be hydrogen or unsubstituted $C_1$ to $C_5$ alkyl.

The compound may also have the formula:

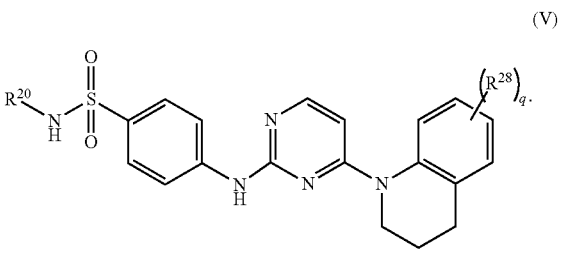

(V)

In Formula (V), $R^{20}$, $R^{28}$, and q are as defined above in the definitions of Formula (IV). In some embodiments, $R^{20}$ is unsubstituted $C_1$ to $C_{10}$ alkyl. $R^{28}$ may be —OR$^{40}$. $R^{40}$ is hydrogen or unsubstituted $C_1$ to $C_{10}$ alkyl, or $C_1$ to $C_{10}$ alkyl substituted with substituted or unsubstituted $C_3$ to $C_6$ cycloalkyl. The symbol q may be 1.

In another embodiment, the compound has the formula:

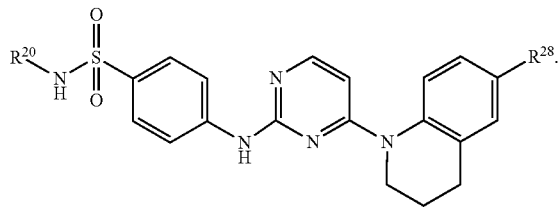

(VI)

In Formula (VI), $R^{20}$, $R^{28}$, and q are as defined above in the definitions of Formula (IV) or Formula (VI).

In another embodiment, the compound has the formula:

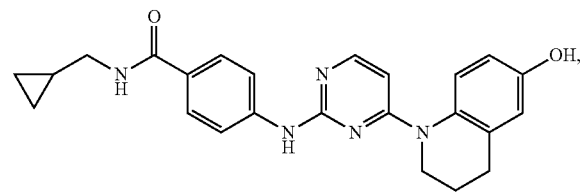

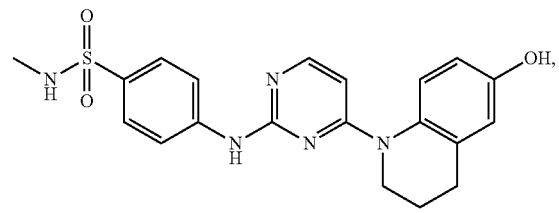

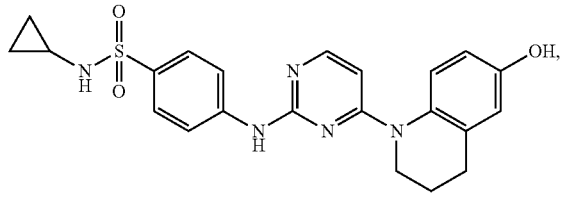

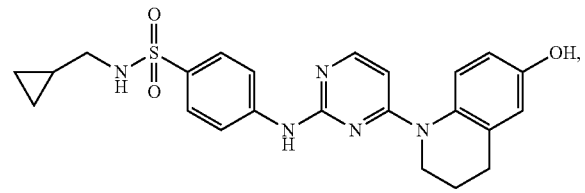

(sometimes called Pyrintegrin or "Ptn")

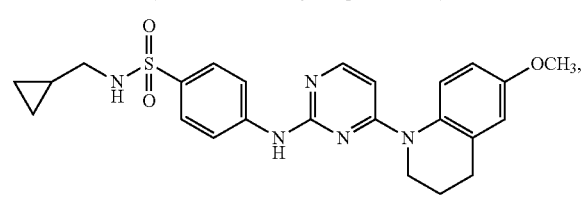

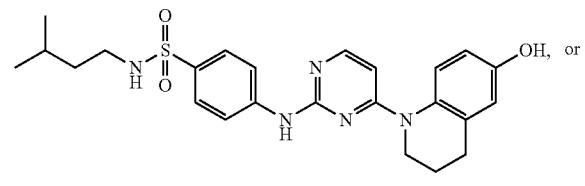

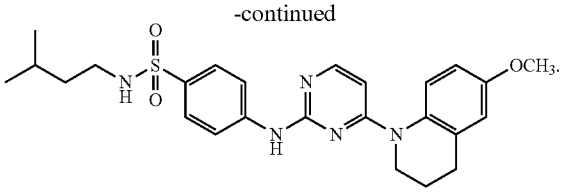

In other embodiments, the compounds of formula III are those where Ring D is aryl or heteroaryl, each optionally substituted with 1-5 R groups; $L^3$ is —C(O)NH— or —S(O)$_2$NH—; $R^{20}$ is $C_{1-10}$ alkyl, $C_{1-10}$ heteroalkyl, cycloalkyl, heterocycloalkyl, aryl, or heteroaryl, each optionally substituted with 1-5 R groups; $R^{21}$ is —NR$^{22}$R$^{23}$ or —OR$^{24}$; $R^{22}$ and $R^{23}$ are independently hydrogen, $C_{1-10}$ alkyl, $C_{1-10}$ heteroalkyl, cycloalkyl, heterocycloalkyl, aryl, heteroaryl, or are joined together to form a heterocycloalkyl or heteroaryl, each optionally substituted with 1-5 R groups; $R^{24}$ is $C_{1-10}$ alkyl, $C_{1-10}$ heteroalkyl, cycloalkyl, heterocycloalkyl, aryl, heteroaryl, each optionally substituted with 1-5 R groups; and each R group is independently selected from the group consisting of $C_{1-10}$ alkyl, $C_{1-10}$ heteroalkyl, —OR', =O, =NR', =N—OR', —NR'R", —SR', -halogen, —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NR—C(NR'R"R''')=NR'''', —NR—C(NR'R")=NR''', —S(O)R', —S(O)$_2$R', —S(O)$_2$NR'R", —NRSO$_2$R', —CN, —NO$_2$, cycloalkyl, heterocycloalkyl, aryl, and heteroaryl, wherein each R', R", R''' and R'''' is independently selected from the group consisting of hydrogen, $C_{1-10}$ alkyl, $C_{1-10}$ heteroalkyl, cycloalkyl, heterocycloalkyl, aryl, and arylalkyl groups.

In some embodiments, each substituted group described above in the compounds of Formulae (I)-(VI) is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, and/or substituted heteroalkylene described above in the compounds of Formulae (I)-(VI) are substituted with at least one substituent group. In other embodiments, at least one or all of these groups are substituted with at least one size-limited substituent group. Alternatively, at least one or all of these groups are substituted with at least one lower substituent group.

In other embodiments of the compounds of Formulae (I)-(VI), each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted alkylene is a substituted or unsubstituted $C_1$-$C_{20}$ alkylene, and/or each substituted or unsubstituted heteroalkylene is a substituted or unsubstituted 2 to 20 membered heteroalkylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_5$-$C_7$ cycloalkyl, each substituted or unsubstituted heterocycloalkyl is a substituted or unsubstituted 5 to 7 membered heterocycloalkyl, and/or each substituted or unsubstituted alkylene is a substituted or unsubstituted $C_1$-$C_8$ alkylene, and/or each substituted or unsubstituted heteroalkylene is a substituted or unsubstituted 2 to 8 membered heteroalkylene.

In some other embodiments, the compounds of formula (I)-(VI) can be substituted with $C_{1-10}$ alkyl, $C_{1-10}$ heteroalkyl, —OR', =O, =NR', =N—OR', —NR'R", —SR', -halogen, —SiR'R"R"', —OC(O)R', —C(O)R', —CO$_2$R', —CONR'R", —OC(O)NR'R", —NR"C(O)R', —NR'—C(O)NR"R"', —NR"C(O)$_2$R', —NR—C(NR'R"R"')=NR"", —NR—C(NR'R")=NR"', —S(O)R', —S(O)$_2$R', —S(O)$_2$NR'R", —NRSO$_2$R', —CN, —NO$_2$, cycloalkyl, heterocycloalkyl, aryl, or heteroaryl, wherein each R', R", R"' and R"" hydrogen, $C_{1-10}$ alkyl, $C_{1-10}$ heteroalkyl, cycloalkyl, heterocycloalkyl, aryl, or arylalkyl groups.

III. Methods of Use

The compounds of the present invention are useful for a wide variety of purposes. For example, the compounds promote survival in situations (e.g., for isolated cells) where the cells would otherwise go through apoptosis or otherwise die. In some embodiments, the cells are stabilized for at least a particular period of time, e.g., 10 minutes, 30 minutes, or 1, 2, 4, 6, 8, 10, 24, 48, or 96 hours. Further, the compounds are useful in maintaining the current state of differentiation of cells in conditions where the cells would otherwise differentiate or otherwise change their programming. These effects lead to a large number of uses for the compounds either in vitro or in vivo.

A. In Vivo Uses

The compounds of the invention are useful for reducing tissue damage and thus can be administered to treat, ameliorate, or prevent tissue damage. In some embodiments, a compound of the invention is administered to an individual having, or at risk of having tissue damage to an internal organ. Internal organs include, but are not limited to, brain, pancreas, liver, intestine, lung, kidney, or heart, wounding, e.g., by burn or cut. For example, in some embodiments, the compounds of the invention are effective in reducing infarction size in reperfusion following ischemia. Thus, a compound of the invention can be administered to individuals at risk of having, having, or who have had, a stroke. Similarly, a compound of the invention can be administered to individuals at risk of having, having, or who have had, a heart attack or cardiac damage.

The inventors have found that the compounds of the invention can prevent cell death, for example in epithelial cells. For example, the inventors dispersed primary human pancreatic islets/beta cells plated as single cells onto a tissue culture plate that was coated with matrigel or laminin. In regular cell culture media for beta cells without Tzv resulted in substantial cell death. However, when Tzv was added to the media (1-2 mM), cell death was inhibited. The same effect was observed for other epithelial primary cells, such as neural cells. Accordingly, in some embodiments, a compound of the present invention is administered to an individual in need of pancreatic beta and/or islet cells, wherein administration of the compound results in an increase in the number of beta or islet cells in the individual.

Further, the compounds of the invention (e.g., those of Formulae I or III) are effective in increasing blood flow and inhibiting inflammatory responses. For example, compounds of Formula I enhance adhesion and migration of monocytes across monolayers of endothelial cells and can thus relieve inflammatory responses (data not shown). Thus, in some embodiments, a compound of the invention is administered to an individual (e.g., having cerebral ischemia) in need of increased blood flow and/or decreased inflammation. Those in need of reduced inflammation include individuals with inflammatory disease or with a disease mediated by an inflammatory condition. Exemplary inflammatory diseases include, but are not limited to, chronic obstructive pulmonary disease, osteoarthritis, tendinitis or bursitis, gouty arthritis, polymyalgia rheumatica, fibromyalgia, pelvic inflammatory disease and arthritis, including rheumatoid arthritis In some embodiments, the compounds of the present invention are used to treat or ameliorate cancer. In some cases, a compound of the present invention is administered to treat cancer, e.g., carcinomas, gliomas, mesotheliomas, melanomas, lymphomas, leukemias, adenocarcinomas, breast cancer, ovarian cancer, cervical cancer, glioblastoma, leukemia, lymphoma, prostate cancer, and Burkitt's lymphoma, head and neck cancer, colon cancer, colorectal cancer, non-small cell lung cancer, small cell lung cancer, cancer of the esophagus, stomach cancer, pancreatic cancer, hepatobiliary cancer, cancer of the gallbladder, cancer of the small intestine, rectal cancer, kidney cancer, bladder cancer, prostate cancer, penile cancer, urethral cancer, testicular cancer, cervical cancer, vaginal cancer, uterine cancer, ovarian cancer, thyroid cancer, parathyroid cancer, adrenal cancer, pancreatic endocrine cancer, carcinoid cancer, bone cancer, skin cancer, retinoblastomas, Hodgkin's lymphoma, non-Hodgkin's lymphoma (see, CANCER:PRINCIPLES AND PRACTICE (DeVita, V. T. et al. eds 1997) for additional cancers).

Cancer cell metastasis is typically a process involving epithelial to mesenchymal transition/EMT (e.g. from epithelial-type cells to fibroblast-type cells). The inventors have found that the compounds of the invention (i.e., Tvz and Ptn) can induce MET (the reverse of EMT) and inhibit EMT, indicating that compounds are effective at reducing or preventing cancer metastasis. Accordingly, in some embodiments, a compound of the present invention is administered to an individual having or at risk of having cancer metastasis. For example, the inventors have found that compounds of formula I and III inhibit metastasis of epithelial cancers including but not limited to breast cancer and hepatocellular carcinoma.

In some embodiments, a compound of the present invention is administered to an individual having, or at risk of having, hypertension and/or atherosclerosis.

Compounds of formula I and III (i.e., Tvz and Ptn) are effective at promoting axonal regeneration and functional recovery in injured central nervous system. For example, the inventors have found that Tvz can promote neurite outgrowth from primary neuronal cells from mice. Tzv (3 μM) was tested on mouse P1 cortical explants, with axon outgrowth as an outcome read-out. Tzv was added to the medium 20 minutes after plating, with DMSO as a control. The explants were observed for 4 days in culture. Tzv showed a dramatic effect in promoting axon outgrowth, which was notable from 1 div. Accordingly, in some embodiments, a compound of the present invention is administered to an individual having a central nervous system injury or who is in need or would otherwise benefit from axonal regeneration.

In some embodiments, a compound of the present invention is administered to an individual having diabetes, insulin resistance, or otherwise in need to promotion of beta cell survival, or at risk of having loss of beta cell function.

The compounds of the invention also find use in ameliorating negative symptoms of, or otherwise improving, organ, cell, or tissue transplantation. As explained herein, the compounds of the invention are effective in stabilizing and maintaining contextual programming of cells. Thus, in some embodiments, a compound of the invention is administered during and after transplantation of cells, tissue or an organ to an individual. Examples of transplantation include, but are not limited to, transplantation of bone marrow, umbilical cord blood, purified hematopoietic stem/progenitor cells, cardiac cells, neural cells, pancreatic beta cells, and liver cells.

B. In Vitro Uses

The compounds of the present invention are effective at stabilizing cells exposed to a wide variety of conditions. Many animal cells, when isolated (in suspension or alternatively, when adherent) lose viability, go through apoptosis, and/or change programming (for example, stem cells when isolated, will often die or differentiate). The compounds of the present invention, when mixed with such cells, are effective in preventing such cellular responses to environmental changes. In some embodiments, cells are isolated from an animal and contacted with a compound of the invention in a sufficient amount to prevent loss of cell viability and/or changes in cellular programming. In some embodiments, such isolated cells are useful for diagnostics as the cells isolated retain phenotypes that would otherwise be lost due to the cell's response to the isolation process and isolation itself. Exemplary retained phenotypes can include, for example, gene expression patterns, cell responsiveness to a stimulus, ligand, or drug, cell viability.

Stability of a cell population can be monitored, for example, by monitoring expression of gene products. For example, certain gene products are tissue or cell type-specific and can be monitored before and after a change in condition or environment (for example, changing of cell media, thawing of cell, isolation of cell from other cells, etc.) to determine whether the change affects cellular programming. In some embodiments, cells about to be submitted to a change of condition or environment, or relatively soon after (e.g., within 1 minute, 5 minutes, one hour, etc., depending on circumstances) the change, are contacted with a compound of the invention in a sufficient amount such that one or more cellular expression markers remain substantially the same. "Substantially the same" will depend upon context and will be understood in the art. In some embodiments, "substantially the same" means that expression of a gene product associated with a specific cell type does not change more than about 10%, 20% or 30% following a particular treatment to the cell (e.g., compared to expression prior to the treatment).

In some embodiments, the invention provides methods of promoting survival and anti-differentiation in stem cells ex-vivo. For example, the inventors have found that compounds of Formulae I or III (i.e., Tzv and Ptn) are effective in promoting survival and anti-differentiation in human embryonic stem cell, mouse embryonic stem cell, multiple neural stem cells, skin stem cells, mesenchymal stem cells, hematopoietic stem cells, stromal stem cells and epithelial stem cells by contacting the cells with a compound of Formula I or III immediately after the isolation of the cells Accordingly, the present invention provides populations of cells and/or tissue in contact with a sufficient amount of a compound of the invention (e.g., a compound of Formula I or III) to stabilize the cells, e.g., to prevent or reduce cellular responses to changes in conditions (e.g., isolation from a tissue, thawing of the cells, etc.). In some embodiments, for example, the cells or tissues in contact with a compound of the invention are in a frozen or a liquid states. In some embodiments, the cells/tissues are thawed from a frozen state while in contact with a sufficient amount of a compound of the invention to prevent or reduce cellular damage or differentiation.

In some embodiments, a compound of the invention is contacted to a population of stem cells, progenitor cells or differentiated cells. Exemplary stem cells include pluripotent stem cells, embryonic stem cells, induced stem cells (iPS cells). Exemplary stem cells also include human embryonic stem cells, mouse embryonic stem cells, multiple neural stem cells, skin stem cells, mesenchymal stem cells, hematopoietic stem cells, stromal stem cells, and epithelial stem cells. Any type of progenitor cells can be used, including but not limited to, endoderm progenitor cells, mesoderm progenitor cells (e.g., muscle progenitor cells, bone progenitor cells, blood progenitor cells), and ectoderm progenitor cells (e.g., epidermal tissue progenitor cells and neural progenitor cells). There are a wide variety of differentiated cells known. Differentiated cells include, but are not limited to, fibroblasts, cardiac cells, neural cells, pancreatic beta cells, liver cells, epithelial cells, and intestinal cells. The cells described herein can be human cells or non-human cells. In some embodiments, the cells are human cells. In some embodiments, the cells are mouse, dog, cow, pig, rat or non-human primate cells.

The ability to maintain cell viability and cellular programming allow for improved methods of drug screening and diagnostics. For example, in some embodiments, a cell is screened for a response in the presence of at least one compound of the invention (e.g., a compound of formula I or III), thereby maintaining viability of the cell, and further contacted with at least one of a plurality of agents (e.g., a chemical library) and then monitored for a response. A wide range of screening methods are known. This method finds particular benefit for use with cells that would otherwise have a poor viability in the conditions of the screening method (for example, where it is convenient to use isolated cells, cells in suspension, adhesive cells, etc.). The cells can be, for example, stem cells, progenitor cells or differentiated cells, as described herein. The cellular response can be any response desired. Some responses in cell-based screening assays include, but are not limited to, expression of a gene (e.g., based on expression of a reporter gene or quantified by PCR or other detection technology), cell viability or loss thereof, induction of apoptosis, etc.

Agents used in the screening methods can be, for example, small organic compounds (e.g., molecular weight less than 10,000 daltons, for example, less than 8000, 6000, 4000, 2000 daltons), lipids, sugars, polypeptides, antibodies, nucleic acids (e.g., oligonucleotides, DNA, RNA, ribozymes, short inhibitory RNA (siRNA), micro RNA (miRNA), etc.).

In some embodiments, the assays are designed to screen large combinatorial libraries by automating the assay steps and providing compounds from any convenient source to assays, which are typically run in parallel (e.g., in microtiter formats or in microwell plates in robotic assays). The combinatorial libraries can be completely random, or comprise members that contain a core structure based on one or more promising lead compounds. The combinatorial libraries can be completely synthetic or can include some or all members that are derived from naturally occurring sources, including, for example, bacteria, fungi, plants, insects and vertebrate (e.g., *Xenopus* (frog) or *Anguilla* (eel)) and non-vertebrate animals (e.g., *Strongylocentrotus* (sea urchin) or mollusks). See also, Boldi, *Combinatorial Synthesis of Natural Product Based Libraries*, 2006, CRC Press.

In one embodiment, high throughput screening methods involve providing a combinatorial chemical or peptide library containing a large number of potential therapeutic compounds (potential modulator or ligand compounds). Such "combinatorial chemical libraries" or "ligand libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. See, for example, U.S. Pat. Nos. 5,663,046; 5,958,792; 6,185,506; 6,541,211; 6,721,665, the disclosures of which are hereby incorporated herein by reference. Such combinatorial chemical libraries include, but are not limited to, peptide libraries (see, e.g., U.S. Pat. No. 5,010,175; Furka, *Int. J. Pept. Prot. Res.* 37:487-493 (1991); Houghton, et al., *Nature* 354:84-88 (1991); and *Combinatorial Peptide Library Protocols*, Cabilly, ed., 1997, Humana Press. Other chemistries for generating chemical diversity libraries can also be used. Such chemistries include, but are not limited to: peptoids (e.g., PCT Publication No. WO 91/19735), encoded peptides (e.g., PCT Publication WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci. USA* 90:6909-6913 (1993)), vinylogous polypeptides (Hagihara et al, *J. Amer. Chem. Soc.* 114:6568 (1992)), nonpeptidal peptidomimetics with glucose scaffolding (Hirschmann et al., *J. Amer. Chem. Soc.* 114:9217-9218 (1992)), analogous organic syntheses of small compound libraries (Chen et al., *J. Amer. Chem. Soc.* 116:2661 (1994); *Combinatorial Libraries: Synthesis, Screening and Application Potential*, Cortese, ed., 1995, Walter De Gruyter Inc; and Obrecht and Villalgordo, *Solid-Supported Combinatorial and Parallel Synthesis of Small-Molecular-Weight Compound Libraries*, 1998, Elsevier Science Ltd), oligocarbamates (Cho et al., Science 261:1303 (1993)), and/or peptidyl phosphonates (Campbell et al., J. Org. Chem. 59:658 (1994)), nucleic acid libraries (see Ausubel, infra, Sambrook and Russell, infra and U.S. Pat. Nos. 6,955,879; 6,841,347; 6,830,890; 6,828,098; 6,573, 098; and 6,399,334), peptide nucleic acid libraries (see, e.g., U.S. Pat. Nos. 5,539,083; 5,864,010 and 6,756,199), antibody libraries (see, e.g., Vaughn et al., *Nature Biotechnology*, 14(3):309-314 (1996) and PCT/US96/10287), carbohydrate libraries (see, e.g., Liang et al., Science, 274:1520-1522 (1996); U.S. Pat. No. 5,593,853; and *Solid Support Oligosaccharide Synthesis and Combinatorial Carbohydrate Libraries*, Seeberger, ed., 2004, John Wiley & Sons (E-book)), small organic molecule libraries (see, e.g., benzodiazepines, Baum C&EN, January 18, page 33 (1993) and U.S. Pat. No. 5,288,514; isoprenoids, U.S. Pat. No. 5,569, 588; thiazolidinones and metathiazanones, U.S. Pat. No. 5,549,974; pyrrolidines, U.S. Pat. Nos. 5,525,735 and 5,519, 134; morpholino compounds, U.S. Pat. No. 5,506,337, and the like). See also, *Combinatorial Library Design and Evaluation: Principles, Software Tools, and Applications in Drug Discovery*, Ghose, et al., eds., 2001, Marcel Dekker; *Molecular Diversity and Combinatorial Chemistry: Libraries and Drug Discovery*, Chaiken and Janda, eds., 1996, Oxford Univ Pr.; and *Combinatorial Library Methods and Protocols*, English, ed., 2002, Humana Press.

Devices for the preparation of combinatorial libraries are commercially available (see, e.g., Advanced Chem Tech, Louisville Ky., Symphony, Rainin, Woburn, Mass., Applied Biosystems, Foster City, Calif., Millipore, Bedford, Mass. and Caliper Life Sciences, Hopkinton, Mass.).

In some embodiments, the screening assays can be conveniently carried out in multiwell plates (e.g., 96-well, 384-well, etc.) wherein each agent to be screened is individually tested in a single well. In some embodiments, two or more candidate agents are tested in a single reaction mixture.

C. Alternative Targets for Obtaining Similar Effects

As described in detail in the examples below, the inventors have learned about the role of several gene products in the cellular response to the compounds of the invention and this has lead to the discovery that cells can also be stabilized by manipulating the gene products as explained below.

1. E-Cadherin

The inventors have found that increasing expression of E-cadherin enhances stem cell survival. Thus, the present invention provides for methods of stabilizing and/or increasing expression of E-cadherin in a cell, thereby stabilizing the cell from a change of conditions that would otherwise be detrimental to viability of the cell. Stabilizing E-cadherin can include, for example, contacting the cells with a compound that increases expression of E-cadherin or in some way protects E-cadherin from proteolytic cleavage.

In some embodiments, the invention provides for methods of culturing stem cells (including but not limited to, human or mouse embryonic stem cells) in a container having a surface coated with a protein comprising at least an ectodomain of E-cadherin, optionally linked to another component such as a fusion protein, thereby stabilizing the cells (e.g., maintaining or increasing viability of the cells and/or maintaining cellular programming). An ectodomain is the part of a membrane protein that extends into the extracellular space (the space outside a cell). In some embodiments, ectodomains are the part of a protein that initiate contact with surface which leads to signal transduction. The ectodomain of E-cadherin is described in, e.g., Ito et al., *Oncogene* 18(50):7080-90 (1999) In some embodiments, at least the ectodomain of E-cadherin is fused to a dimerizing polypeptide sequence, thereby allowing for stabilized dimers of the ectodomain. A "dimerizing polypeptide" refers to an amino acid sequence that forms homo-dimers, thereby allowing two polypeptides to dimerize. Exemplary dimerizing polypeptides include, but are not limited to, an IgG Fc fragment. In some embodiments, in some embodiments, stem cells (including but not limited to human or mouse embryonic stem cells, pluripotent stem cells, iPS cells) are dissociated from each other and cultured in a container having a surface coated with a protein comprising at least an ectodomain of E-cadherin, optionally linked to another component such as a fusion protein, thereby stabilizing the cells in improving the survival rate of the cells compared to the survival rate of similarly treated cells cultured in a container lacking the polypeptide coating.

2. Protein Kinase C

The present invention also provides for stabilizing cells by contacting the cells with a protein kinase C activator. As explained herein, treatment of dissociated hESCs with a protein kinase C activator grown in the presence of a matrigel matrix resulted in significantly improved cell adhesion and colony formation, thereby improving cell viability. Accordingly, the invention provides for improving cell viability by culturing cells in the presence of a protein kinase C activator, thereby improving cell viability, growth, and/or adhesion. In some embodiments, a protein kinase C activator is contacted to a populations of stem cells, progenitor cells or differentiated cells in an amount sufficient to improve cell viability and/or survival and/or adhesion. Exemplary stem cells include pluripotent stem cells, embryonic stem cells, induced stem cells (iPS cells) or as otherwise described herein. Exemplary protein kinase C activators include, but are not limited to, phorbol esters (e.g., phorbol 12-myristate 13-acetate (PMA) or phorbol esters as described in US Patent Publication No. 20080226589) or peptide agonists (e.g., as described in U.S. Pat. No. 6,165,977).

3. Integrin β1

The present invention also provides for stabilizing cells by contacting the cells with an integrin β1 activator. As explained herein, treatment of dissociated hESCs with an integrin β1 activator, where the cells are grown on lamin resulted in significantly improved cell adhesion and colony formation, thereby improving cell viability. Accordingly, the invention provides for improving cell viability by culturing cells in the presence of an integrin β1 activator, thereby improving cell viability, growth, and/or adhesion. In some embodiments, an integrin β1 activator is contacted to a populations of stem cells, progenitor cells or differentiated cells in an amount sufficient to improve cell viability and/or survival and/or adhesion. Exemplary stem cells include pluripotent stem cells, embryonic stem cells, induced stem cells (iPS cells) or as otherwise described herein. Exemplary an integrin β1 activators include, but are not limited to, an integrin β1 activating antibody such as, e.g., TS2/16 (commercially available from, e.g., Thermo Scientific, Rockfield, Ill.).

IV. Cell Populations

As discussed herein, the present invention provides for cells in a mixture (e.g., a cell culture) with one or more compound as described herein (e.g., a compound of formula I or III—including but not limited to Tzv and Pt- or a protein kinase C activator or an integrin β1 activator). In some embodiments, the compound is in the mixture at a concentration sufficient to maintain viability or cellular programming in response to a change of cellular environment or condition (e.g., thawing). For example, in some embodiments, the compounds are in a concentration of at least 0.1 nM, e.g., at least 1, 10, 100, 1000, 10000, or 100000 nM, e.g., between 0.1 nM and 100000 nM, e.g., between 1 nM and 10000 nM, e.g., between 10 nM and 10000 nM, e.g., between 1-10 µM. In some embodiments, the mixtures are in a synthetic vessel (e.g., a test tube, Petri dish, etc.). Thus, in some embodiments, the cells are isolated cells (not part of an animal). In some embodiments, the cells are adherent cells or cells in suspension. In some embodiments, the cells are isolated or dissociated from a tissue sample (e.g., a biopsy) from an animal (human or non-human), placed into a vessel, and contacted with one or more compound as described herein (e.g., a compound of Formula I or III). The cells can be subsequently cultured and optionally, inserted back into the same or a different animal, optionally after the cells have been stimulated to differentiate into a particular cell type or lineage, or following introduction of a recombinant expression cassette into the cells.

V. Culturing of Cells

Cells can be cultured according to any method known in the art. Cells can be cultured in suspension or as adherent cells as appropriate.

In some embodiments, the cells (e.g., stem cells) are cultured in contact with feeder cells. Exemplary feeder cells include, but are not limited to fibroblast cells, e.g., mouse embryonic fibroblast (MEF) cells. Methods of culturing cells on feeder cells are known in the art.

In some embodiments, the cells are cultured in the absence of feeder cells. Cells, for example, can be attached directly to a solid culture surface (e.g., a culture plate), e.g., via a molecular tether. Exemplary molecular tethers include, but are not limited to, matrigel, an extracellular matrix (ECM), ECM analogs, laminin, fibronectin, or collagen. Those of skill in the art however will recognize that this is a non-limiting list and that other molecules can be used to attach cells to a solid surface. Methods for initial attachment of the tethers to the solid surface are known in the art.

VI. Formulations and Methods of Administration

Formulations (e.g., comprising a compound of the present invention, including but not limited to suitable for administration include aqueous and non-aqueous solutions, isotonic sterile solutions, which can contain antioxidants, buffers, bacteriostats, and solutes that render the formulation isotonic, and aqueous and non-aqueous sterile suspensions that can include suspending agents, solubilizers, thickening agents, stabilizers, and preservatives. In the practice of this invention, compositions can be administered, for example, orally, nasally, topically, intravenously, intraperitoneally, or intrathecally. The formulations of compounds can be presented in unit-dose or multi-dose sealed containers, such as ampoules and vials. Solutions and suspensions can be prepared from sterile powders, granules, and tablets of the kind previously described. The modulators can also be administered as part of a prepared food or drug.

The dose administered to a patient, in the context of the present invention, should be sufficient to induce a beneficial response in the subject over time. The optimal dose level for any patient will depend on a variety of factors including the efficacy of the specific modulator employed, the age, body weight, physical activity, and diet of the patient, on a possible combination with other drugs, and on the severity of the disease or condition in question. The size of the dose also will be determined by the existence, nature, and extent of any adverse side-effects that accompany the administration of a particular compound or vector in a particular subject.

In determining the effective amount of an active ingredient to be administered a physician may evaluate circulating plasma levels of the compound or agent, compound or agent toxicity, and the production of anti-compound or agent antibodies. In general, the dose equivalent of a compound or agent is from about 1 ng/kg to 10 mg/kg for a typical subject.

VII. Examples

The following examples are offered to illustrate, but not to limit the claimed invention.

Example 1

To improve chemically-defined medium conditions and uncover the molecular mechanism of hESC death after single cell dissociation, we performed a high throughput phenotypic screen of 50,000 synthetic compounds to identify small molecules that promote hESC survival after trypsin dissociation. From the screen, two chemical classes were identified that significantly increased the cell survival after dissociation and also maintained hESC colony morphology and alkaline phosphatase (ALP) expression. Further chemical optimizations and activity analysis resulted in the discovery of two lead molecules, a 2,4-disubstituted thiazole (named as Thiazovivin/Tzv) and a 2,4-disubstituted pyrimidine (named as Pyrintegin/Ptn) (FIG. 1a), for further functional and mechanistic characterizations.

TABLE 1

Activity Data

| Compound | Activity (% ALP positive colony formation by hESCs)[1] |
|---|---|
| (2-(pyrimidin-4-ylamino)thiazole-4-carboxamide, N-benzyl) | 24.1 |
| (2-(phenylamino)thiazole-4-carboxamide, N-benzyl) | 4.5 |
| (2-(pyridin-2-ylamino)thiazole-4-carboxamide, N-benzyl) | 5.2 |
| (2-(pyridin-4-ylamino)thiazole-4-carboxamide, N-benzyl) | 20.3 |
| (2-(pyrimidin-4-ylamino)thiazole-4-carboxamide, N-(4-methoxybenzyl)) | 5 |

TABLE 1-continued
Activity Data
| Compound | Activity (% ALP positive colony formation by hESCs)[1] |
|---|---|
| 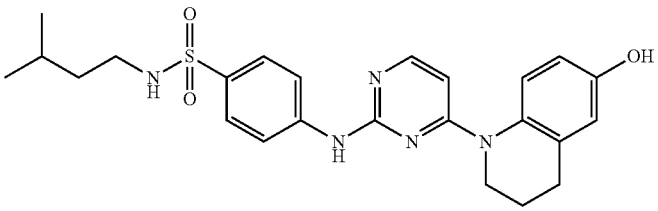 [SMILES: CC(C)CCNS(=O)(=O)c1ccc(Nc2nccc(N3CCCc4cc(O)ccc43)n2)cc1] | 23.5 |
| 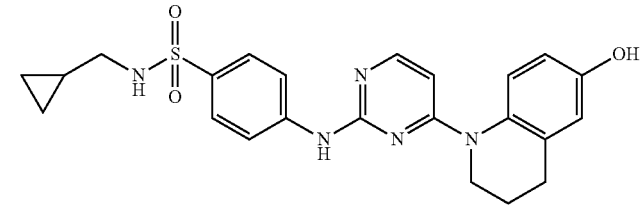 [SMILES: O=S(=O)(NCC1CC1)c1ccc(Nc2nccc(N3CCCc4cc(O)ccc43)n2)cc1] | 23.2 |
| 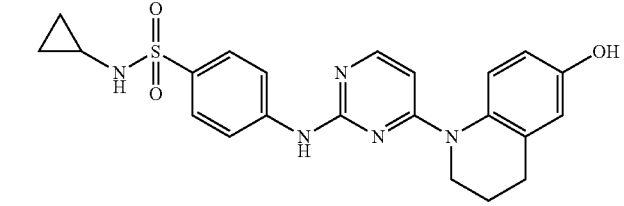 [SMILES: O=S(=O)(NC1CC1)c1ccc(Nc2nccc(N3CCCc4cc(O)ccc43)n2)cc1] | 8 |
| 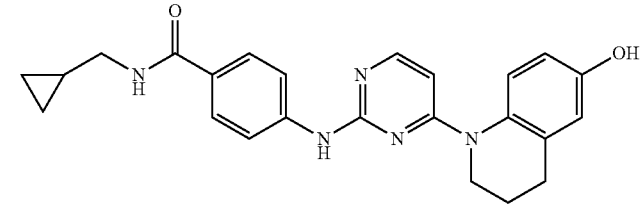 [SMILES: O=C(NCC1CC1)c1ccc(Nc2nccc(N3CCCc4cc(O)ccc43)n2)cc1] | 2.9 |
| 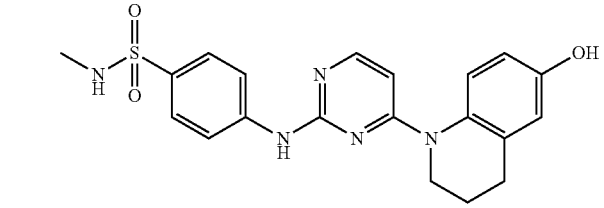 [SMILES: CNS(=O)(=O)c1ccc(Nc2nccc(N3CCCc4cc(O)ccc43)n2)cc1] | 5.7 |
| 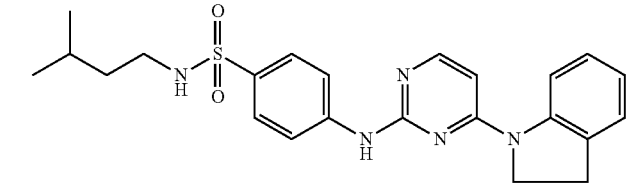 [SMILES: CC(C)CCNS(=O)(=O)c1ccc(Nc2nccc(N3CCc4ccccc43)n2)cc1] | 3.1 |
| 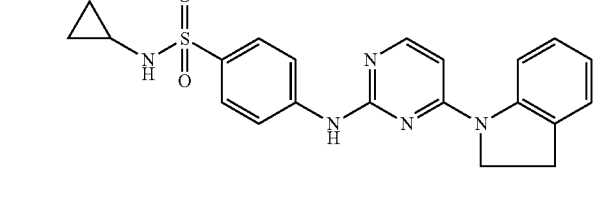 | 6.2 |

TABLE 1-continued

Activity Data

| Compound | Activity (% ALP positive colony formation by hESCs)[1] |
|---|---|
| [structure: cyclopropylmethyl-NH-SO2-phenyl-NH-pyrimidine-indoline] | 6.1 |
| [structure: cyclopropylmethyl-NH-SO2-phenyl-NH-pyrimidine-isoindoline] | 3.5 |
| [structure: methyl-NH-SO2-phenyl-NH-pyrimidine-tetrahydroisoquinoline] | 3.6 |
| [structure: isopentyl-NH-SO2-phenyl-NH-pyrimidine-tetrahydroisoquinoline] | 3.2 |
| [structure: methyl-NH-SO2-phenyl-NH-pyrimidine-tetrahydroquinoline] | 3 |
| [structure: isopentyl-NH-SO2-phenyl-NH-pyrimidine-tetrahydroquinoline] | 3.4 |

TABLE 1-continued

Activity Data

| Compound | Activity (% ALP positive colony formation by hESCs)[1] |
|---|---|
| (cyclopropyl-NH-SO2-C6H4-NH-pyrimidine-tetrahydroquinoline) | 3.1 |
| (cyclopropylmethyl-NH-SO2-C6H4-NH-pyrimidine-tetrahydroquinoline) | 5.2 |
| (methyl-NH-SO2-C6H4-NH-pyrimidine-6-OMe-tetrahydroquinoline) | 3.1 |
| (isopentyl-NH-SO2-C6H4-NH-pyrimidine-6-OMe-tetrahydroquinoline) | 3.3 |
| (cyclopropylmethyl-NH-SO2-C6H4-NH-pyrimidine-NH-phenyl) | 3.3 |
| (isopentyl-NH-SO2-C6H4-NH-pyrimidine-6-OH-tetrahydroquinoline) | 3.1 |

[1]Ratio of ALP positive colonies vs. total initially seeded cells.

Figure 2:
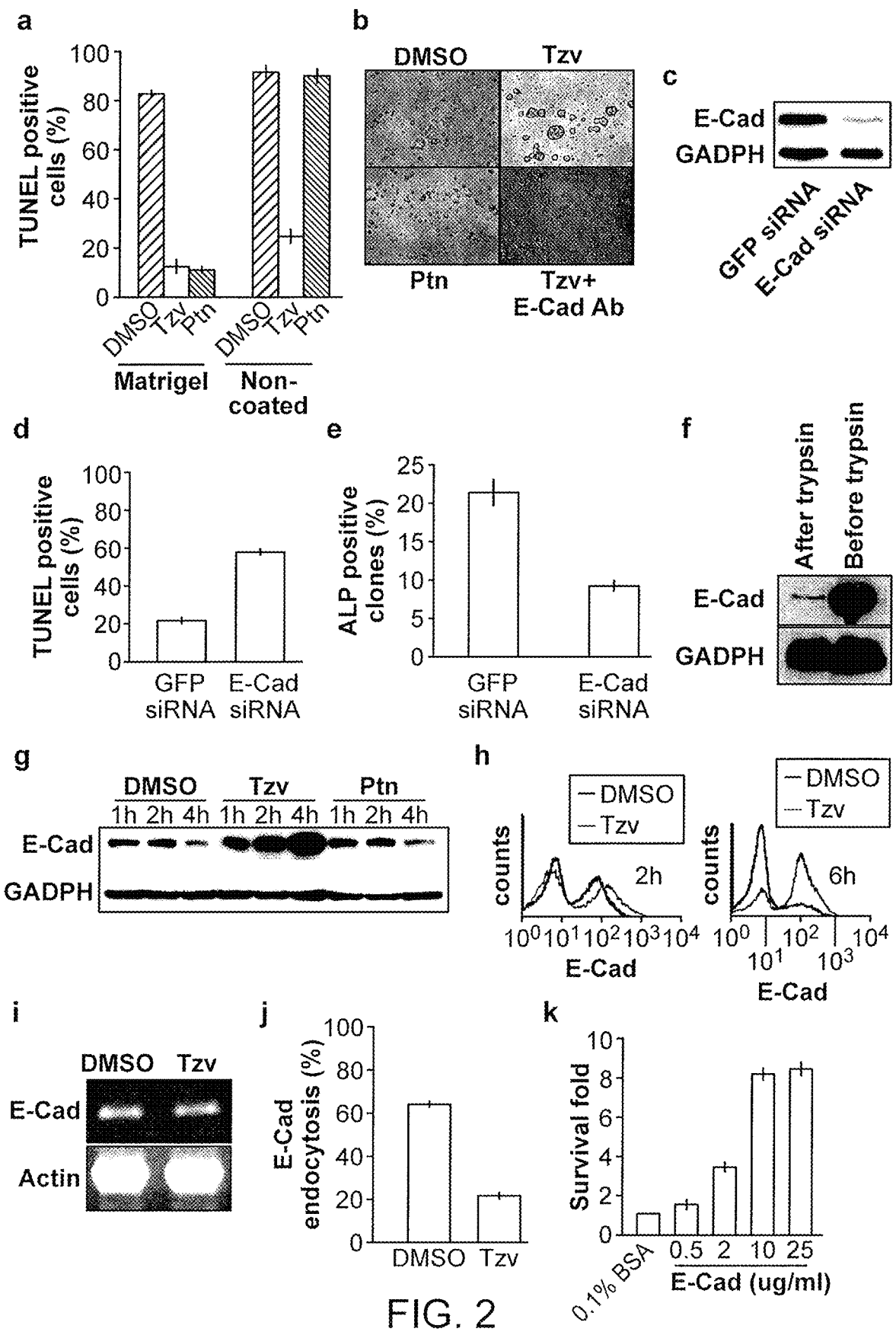
FIG. 2. Tzv stabilizes E-cadherins after cell dissociation to protect hESCs from death in suspension culture. (a) Cell death analysis of dissociated hESCs grown on Matrigel or in suspension treated with or without Ptn or Tzv. (b) Phase contrast images of hESCs grown on non-coated plates treated with the indicated molecules. (c) Western blot analysis of E-cadherins in hESCs that were transfected with the specific siRNAs against E-cadherin or GFP. (d) Cell death analysis by TUNEL staining of and (e) ALP staining of dissociated hESCs that were transfected with the specific siRNAs against E-cadherin or GFP in the presence Tzv. (f) Western blot analysis of full-length E-cadherins in hESCs before and after trypsin. (g) A time-course Western blot analysis of full-length E-cadherin expression in hESCs after trypsin dissociation and treatment with DMSO, Tzv, or Ptn for indicated time. (h) Flow cytometry analysis of E-cadherin surface level in hESCs after trypsin treatment in the presence of Tzv. DMSO was used as a control. (i) Semi-quantitative RT-PCR of E-cadherin in hESCs treated with or without Tzv. (j) E-cadherin endocytosis analysis in the absence or presence of Tzv. (k) Cell survival analysis of hESCs grown on BSA- or different concentrations of E-cad-Fc chimera-coated plates.

Compound Tzv or Ptn enhances the survival of single hESCs more than 20-fold on Matrigel-coated plate after enzymatic dissociation (FIG. 1b, c). hESCs had been serially passaged in Tzv or Ptn-containing chemically-defined medium for more than 20 generations. Under such conditions, the cells homogenously maintained the characteristic morphology of hESCs, the expression of typical pluripotency markers, and normal karyotype (FIG. 1d, e). When these cells were injected into nude mice, they generated complex teratomas consisting of all three primary germ layer tissues (FIG. 1f). These results, confirmed with several independent hESC lines, collectively and convincingly demonstrated that both compounds could substantially promote hESC survival without compromise to self-renewal and full developmental potency.

hESCs are known to be difficult in forming embryoid bodies (EBs) in suspension culture after single cell dissociation due to extensive cell death. Thus, we also tested whether Tzv or Ptn could promote survival of dissociated hESCs in suspension. Interestingly, Tzv greatly improved survival of hESCs in both adherent and suspension cultures. In contrast, Ptn only promoted survival of hESCs in adherent culture (e.g. on Matrigel-coated plate), but had no effect on suspension culture (FIG. 2a). These observations suggest that at least two distinct mechanisms are involved in these two types of cell death under ECM/Matrigel or suspension conditions, and that Tzv and Ptn function differently. hESCs formed nice cell aggregates when grown in suspension and in the presence of Tzv (FIG. 2b), and could differentiate into various lineages (data not shown). Because cell aggregation is most often mediated through cell-cell adhesions and E-cadherin is the primary cell-cell adhesion molecule, as well as highly expressed in hESCs (Eastham, A. M. et al., Cancer Res 67 (23): 11254-11262 (2007)), we tested the effect of a specific E-cadherin blocking antibody on multicellular aggregate formation. When the cells were cultured in the presence of the antibody, the cell survival and formation of large, compact aggregates induced by Tzv treatment was severely inhibited, indicating that the cell survival and assembly of multicellular aggregates induced by Tzv involve functional E-cadherin (FIG. 2b). In addition, knockdown of E-cadherin by specific siRNAs in hESCs dramatically reduced cell survival induced by Tzv treatment, and significantly decreased the number of ALP positive colonies (FIG. 2c,d,e). These results suggest that Tzv enhances hESC survival in suspension, presumably acting through E-cadherin-mediated cell-cell adhesion.

We then examined E-cadherin expression in hESCs after trypsin dissociation. We found that most of the full length E-cadherin had been cleaved after trypsin dissociation (FIG. 2f). This observation was consistent with the report that the extracellular region of E-cadherin has an endoproteolytic cleavage site near the transmembrane domain (Damsky, C. H. et al., Cell 34 (2):455-466 (1983)). In Tzv-untreated cells, newly synthesized full-length E-cadherin appeared 1 h after enzyme treatment and disappeared after 4 h, suggesting that newly synthesized E-cadherins in dissociated hESCs were not stable. However, in Tzv-treated cells, E-cadherin expression was significantly increased (FIG. 2g). Furthermore, flow cytometry analysis revealed that cell surface E-cadherins in hESCs were significantly increased by Tzv (FIG. 2h). Therefore, Tzv is likely to affect cell adhesion by modulating cell surface level of E-cadherins. Semiquantitative RT-PCR revealed comparable amounts of E-cadherin transcripts in mock controls and Tzv-treated cells (FIG. 2i), suggesting the difference in E-cadherin protein levels was not due to altered transcription levels. It is likely that Tzv exerts its effect through stabilization of E-cadherin on the cell surface. Finally, endocytosis assay revealed that internalization of E-cadherins was significantly blocked by Tzv. These results indicate that Tzv regulates E-cadherin activities through inhibition of endocytosis of E-cadherins (FIG. 2j).

Cell-cell dissociation by trypsin leads to rapid cleavage and subsequent destabilization of E-cadherins. We hypothesized that E-cadherin stability might also be mediated by its homophilic-interaction between the cells. Thus homophilic ligation of E-cadherins with recombinant ligands may stabilize E-cadherins and affect hESC survival. To test this hypothesis, we coated plates with a dimeric E-cadherin-Fc chimera protein containing the E-cadherin ectodomain fused to the IgG Fc fragment (Ecad-Fc). Remarkably, dissociated hESCs attached to the coated surface and their survival rate was significantly increased in a dose dependent manner (FIG. 2k), confirming that cell-cell adhesion mediated by E-cadherin is an important regulator for hESC survival.

Both Tzv and Ptn have dramatic effect on survival of hESCs grown on Matrigel-coated plates. Such survival promoting effect seems unlikely due to influence on cell growth and may be largely attributed to the increase in cell adhesion ability following cell dissociation and seeding processes (FIG. 3a,b). Indeed, dissociated hESCs that were treated with Tzv or Ptn displayed a dramatically increased adhesion to Matrigel or laminin. In contrast, hESCs' adhesion to gelatin or poly-lysine (FIG. 3b and data not shown), which does not involve integrins, was not affected by Ptn or Tzv treatment. The main component of Matrigel is laminin, and it was reported that laminin receptor β1 integrin is highly expressed in hESCs (Xu, C. et al., Nat Biotechnol 19 (10):971-974 (2001)). To test whether Ptn or Tzv acts through β1 integrin, we pretreated cells with a blocking antibody against β1 integrin, and observed that the increased cell attachment induced by compound treatment was completely abolished. This suggests that Tzv and Ptn mediate cell adhesion to ECM substrates through β1 integrin (FIG. 3c).

Figure 3:
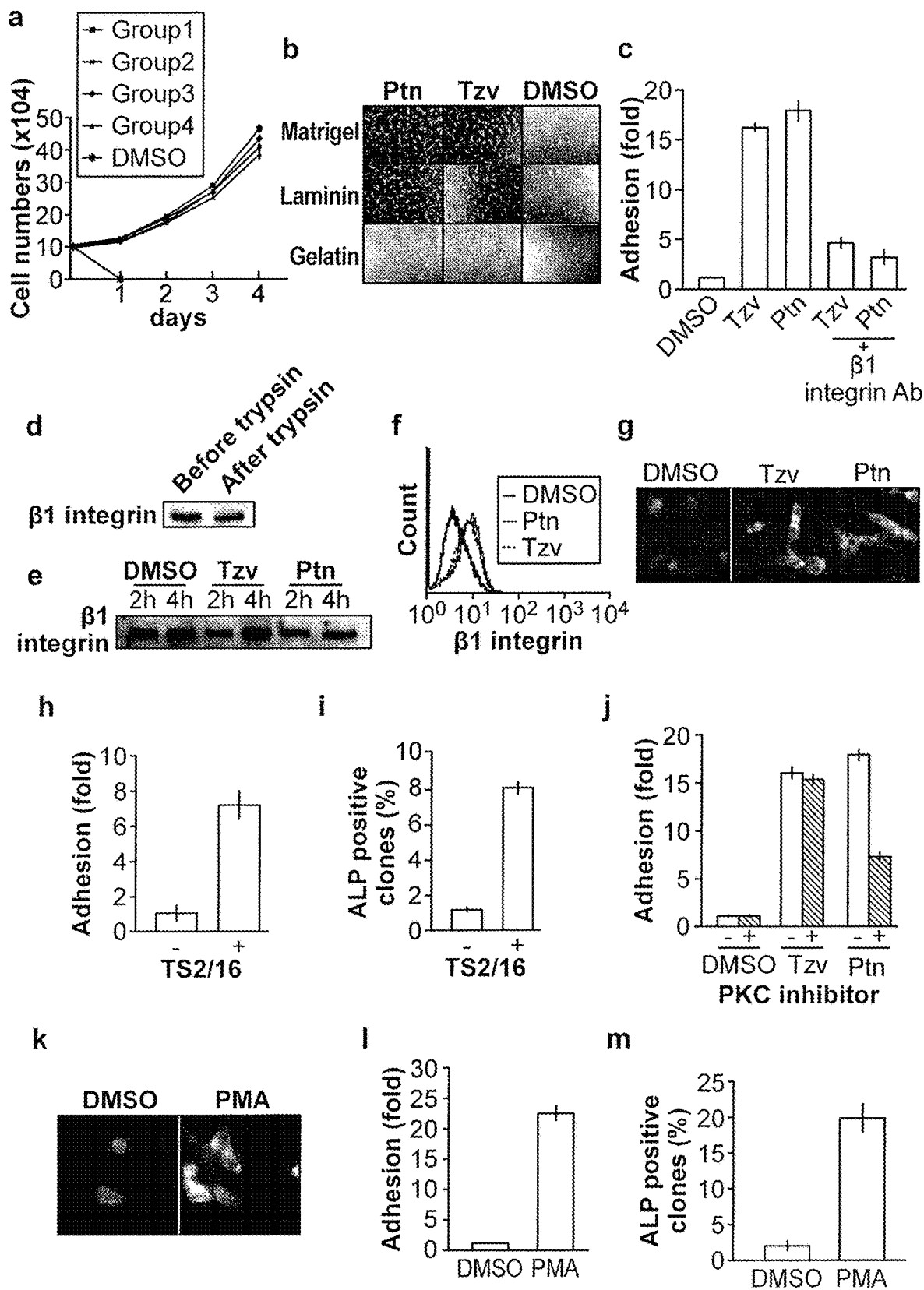
FIG. 3. Ptn and Tzv protect hESCs from cell death in adherent culture after dissociation by maintaining and re-activating integrin activity. (a) Growth curve of hESCs grown on Matrigel with different time courses of Ptn and Tzv treatment. Group 1, Ptn treatment during the first 24 h only; Group 2, continuous Ptn treatment during the entire culture period; Group 3, Tzv treatment during the first 24 h only; Group 4, continuous Tzv treatment during the culture; For each condition, $10 \times 10^4$ dissociated cells were plated per well of a 6-well plate. (b) Phase contrast images of hESCs 12 hours after seeding on the different matrices and treated with the indicated compounds. (c) Dissociated hESCs were plated on Matrigel-coated plates and allowed to adhere for 3 h in the presence of compounds or together with integrin β1 blocking antibody as indicated. The percentage of adhesion was calculated as described in the Materials and Methods. (d) Western blot analysis of integrin β1 expressed by hESCs before and after trypsin treatment. (e) A time course western blot analysis of integrin expression in hESCs after trypsin dissociation and treatment with DMSO, Tzv, or Ptn for indicated time. (f, g) Flow cytometry (f), and immunostaining (g) analysis of the 31 integrins in the active conformation in trypsin-dissociated hESCs after treatment with Tzv or Ptn. (h, i) Cell adhesion (h) and ALP staining (i) of hESCs treated with or without β1-activating antibody, TS2/16. (j) Cell adhesion of hESCs treated with Tzv or Ptn in combination with or without a PKC inhibitor. (k) Immunostaining of β1 integrins in the active conformation in hESCs treated with or without PMA (10 nM). (l, m) Cell adhesion (l) and ALP staining (m) of hESCs treated with the indicated compounds.

To gain insights into the mechanism of β1 integrin regulation by Tzv and Ptn, we investigated whether the compounds' effect is due to changes of integrin expression. In contrast to E-cadherin, β1 integrin was not cleaved by trypsin. Western blot analysis revealed that the compounds' effect was unlikely due to increased expressions of β1 integrin. Thus, Tzv and Ptn are likely to affect cell adhesion by modulating integrin activity (FIG. 3 d,e). To examine the effects of compound treatment on the activity of β1 integrin, we used the monoclonal antibody HUTS-21, which specifically binds to the activated form of the 131 integrin (Luque, A. et al., J Biol Chem 271 (19):11067-11075 (1996)). Notably, compounds treatment increased the level of HUTS-21 binding (FIG. 3f,g). These results collectively suggest that Tzv and Ptn increase cell adhesion by the inside-out modulation of integrin activity.

If both chemicals did enhance cell adhesion by converting integrins into an active conformation, treatment of cells with the integrin-activating antibody, which locks integrins in an active conformation, should have a similar effect as compounds. Indeed, when dissociated hESCs were plated on laminin in the presence of TS2/16, an activating antibody to 31 integrin (van de Wiel-van Kemenade, E. et al., J Cell Biol 117 (2):461-470 (1992)), cell adhesion was significantly increased and cells formed an increased number of colony as compared to control (FIG. 3h,i). These results suggest that the increased adhesion, which occurs when cells are treated with these compounds, involves a mechanism that induces integrin activation.

To further dissect the molecular mechanism by which Tzv and Ptn regulate integrin activity, we examined the effects of several pathway inhibitors. We found that bisindolylmaleimide I, a specific inhibitor of PKC, could antagonize the increased cell adhesion induced by Ptn, but had no effect on cell adhesion induced by Tzv. This suggests that PKC may mediate the action of Ptn but not Tzv (FIG. 3j). To further confirm the role of PKC on hESC survival, dissociated hESCs were treated with PKC agonist phorbol 12-myristate 13-acetate (PMA). Treatment of PMA caused integrin activation, as well as a substantial increase in cell adhesion and colony formation (FIG. 3k,l,m).

Stem cell fate is influenced by its cellular niche, which consists of growth factors, cell-ECM interaction, and cell-cell interaction. The fact that hESC survival is highly dependent on cell-cell interaction and/or cell-ECM interaction, revealed the importance of such previously unrecognized in vitro niche for hESCs. More importantly, cell intrinsic protein expressions (e.g. E-cadherins and integrins) and regulatory mechanisms (e.g. protein stabilization and activation), not only respond to, but also are essential niche components, suggesting stem cells possess intrinsic ability to construct their own niche in the absence of other extrinsic factors or cell types, which however can participate and enhance cells' auto-regulatory niche mechanism.

Figure 4:
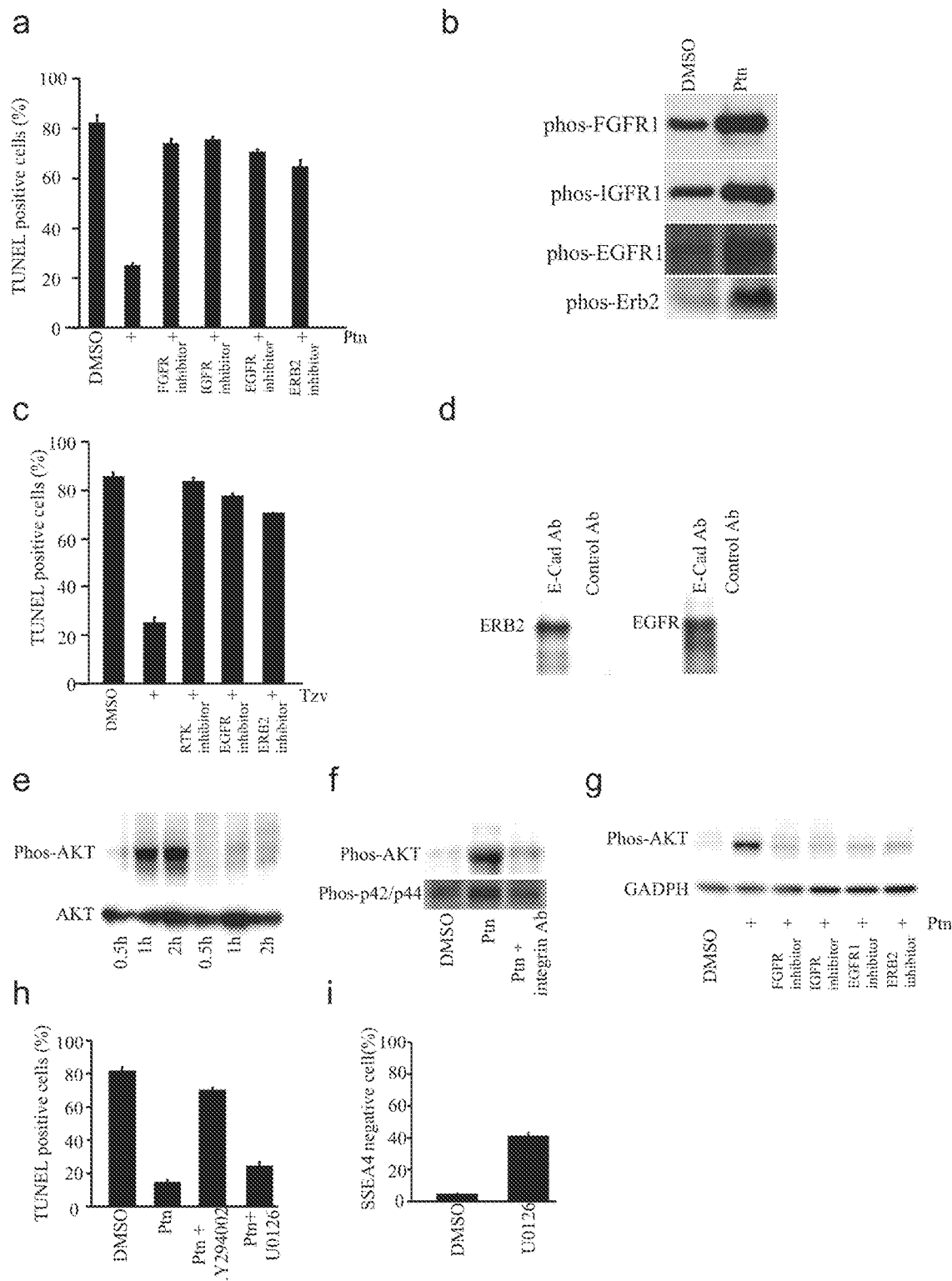
FIG. 4. Growth factors receptors-mediated PI-3 K and ERK are the major surviving and anti-differentiation signaling generated from the hESC niche, respectively. (a) Cell death analysis of dissociated hESCs plated on Matrigel and treated as indicated. (b) Western blot showing the phosphorylation status of different growth factor receptors in hESCs treated with Ptn for 2 h. DMSO was used as a control. (c) Cell death analysis of dissociated hESCs in suspension treated with the indicated conditions. (d) Immunoprecipitation showing the interaction of E-cadherins with EGFR1 and Erb2. (e) Western blot showing AKT phosphorylation status in hESCs treated with Ptn for the indicated time periods. (f) Western blot showing AKT and ERK phosphorylation status in the presence of Ptn or together with integrin β1 blocking antibody. (g) Western blot showing AKT phosphorylation status in hESCs treated with Ptn or together with the indicated receptor inhibitors. (h) Cell death analysis of hESCs treated with Ptn or together with PI-3 K inhibitor, or MEK inhibitor for 24 h. (i) Percentage of SSEA4 negative cells after treatment with MEK inhibitor.
Figure 5A:
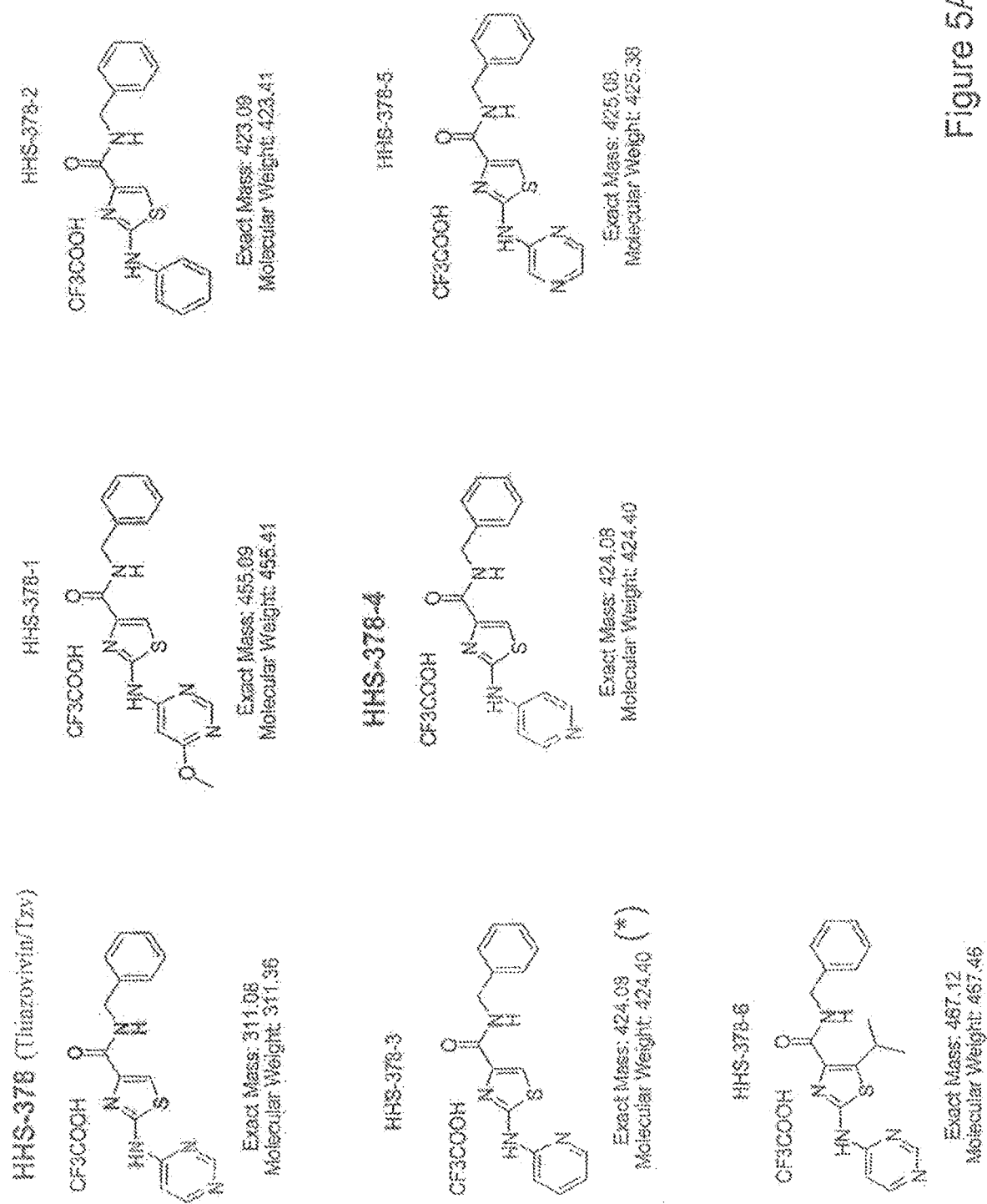
FIGS. 5A and 5B show compounds of the present invention, including thiazovivin and derivatives thereof.
Figure 5B:
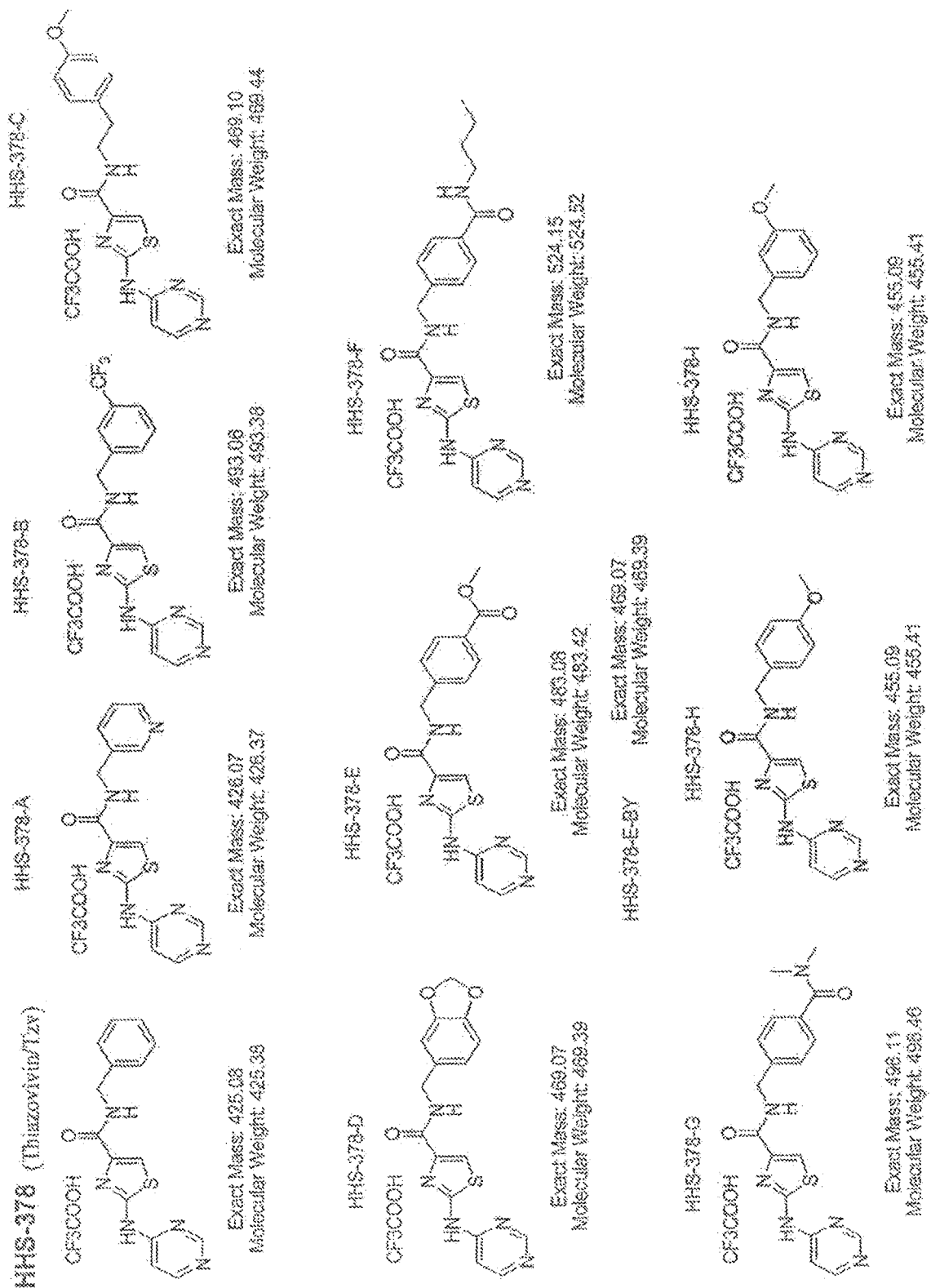
Figure 6A:
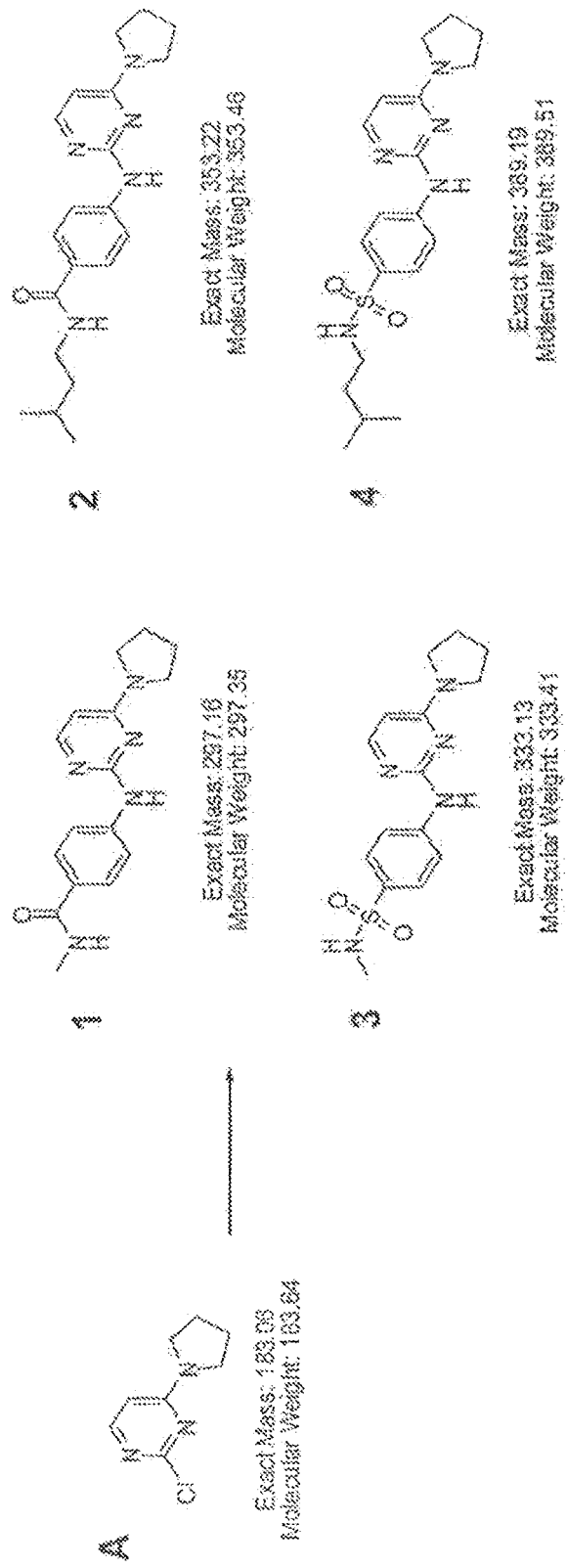
Figure 6B:
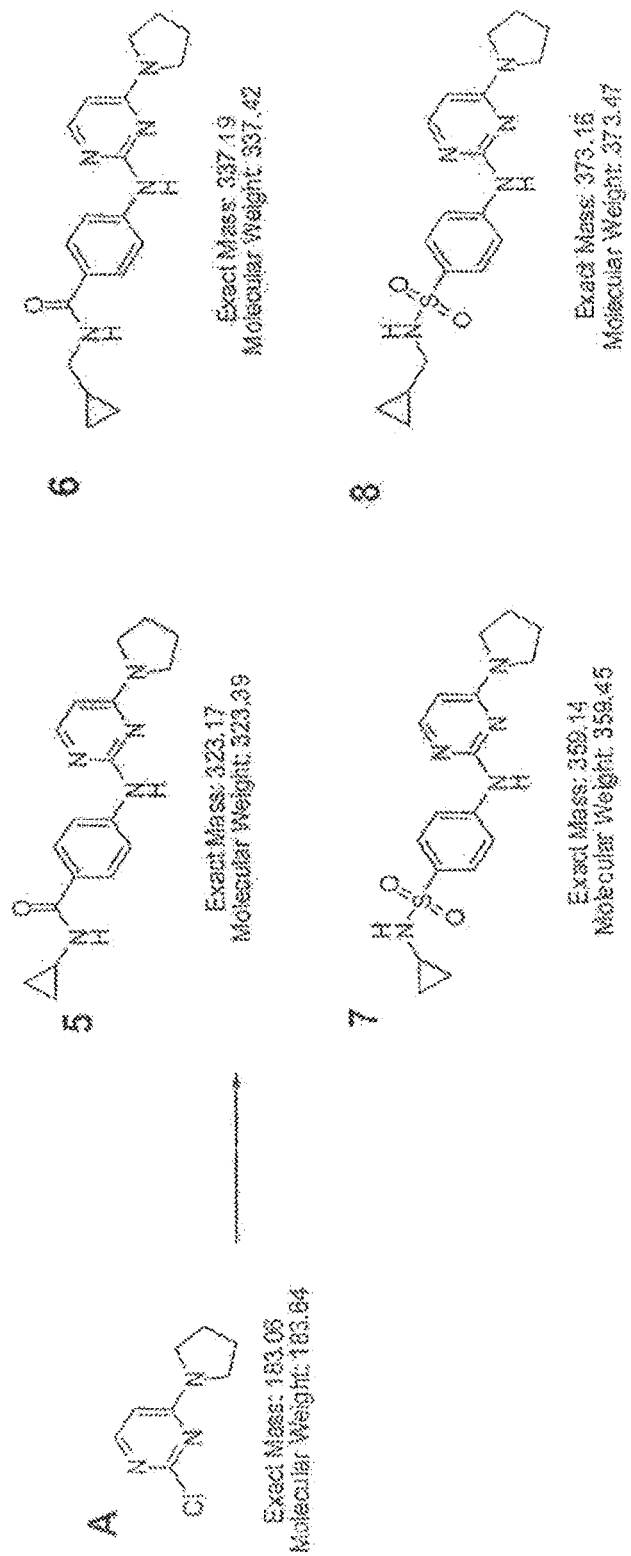
Figure 6C:
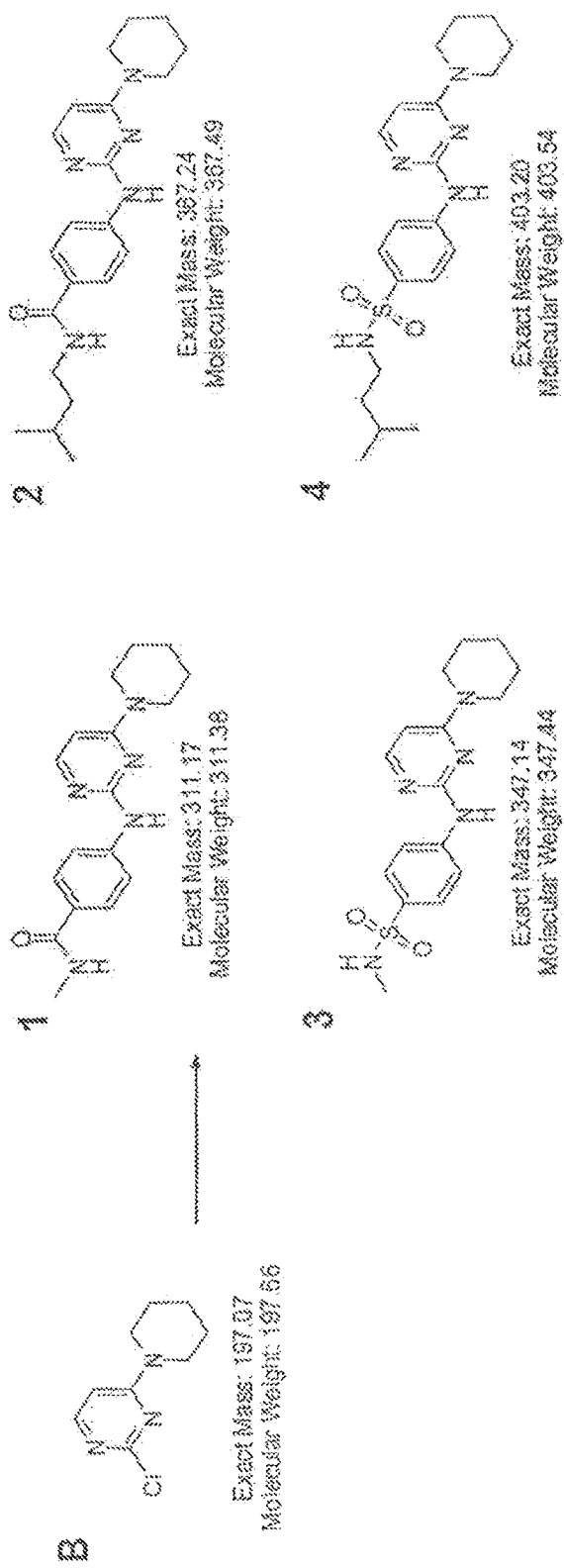
Figure 6D:
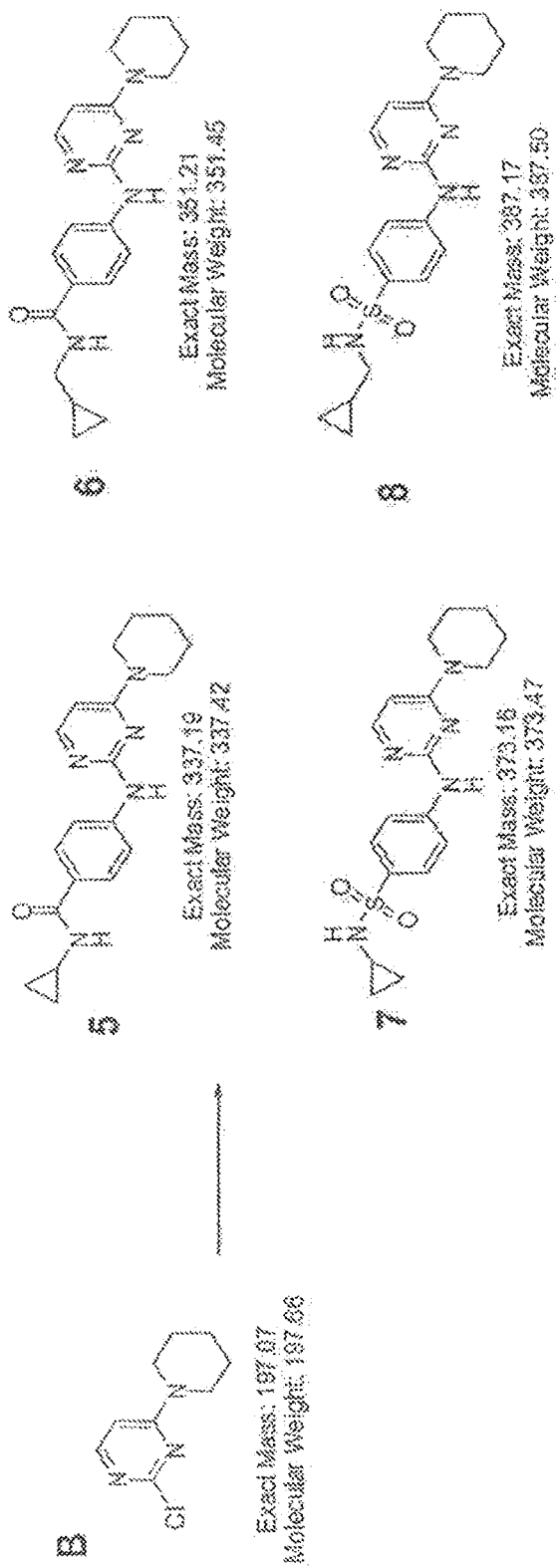
Figure 6E:
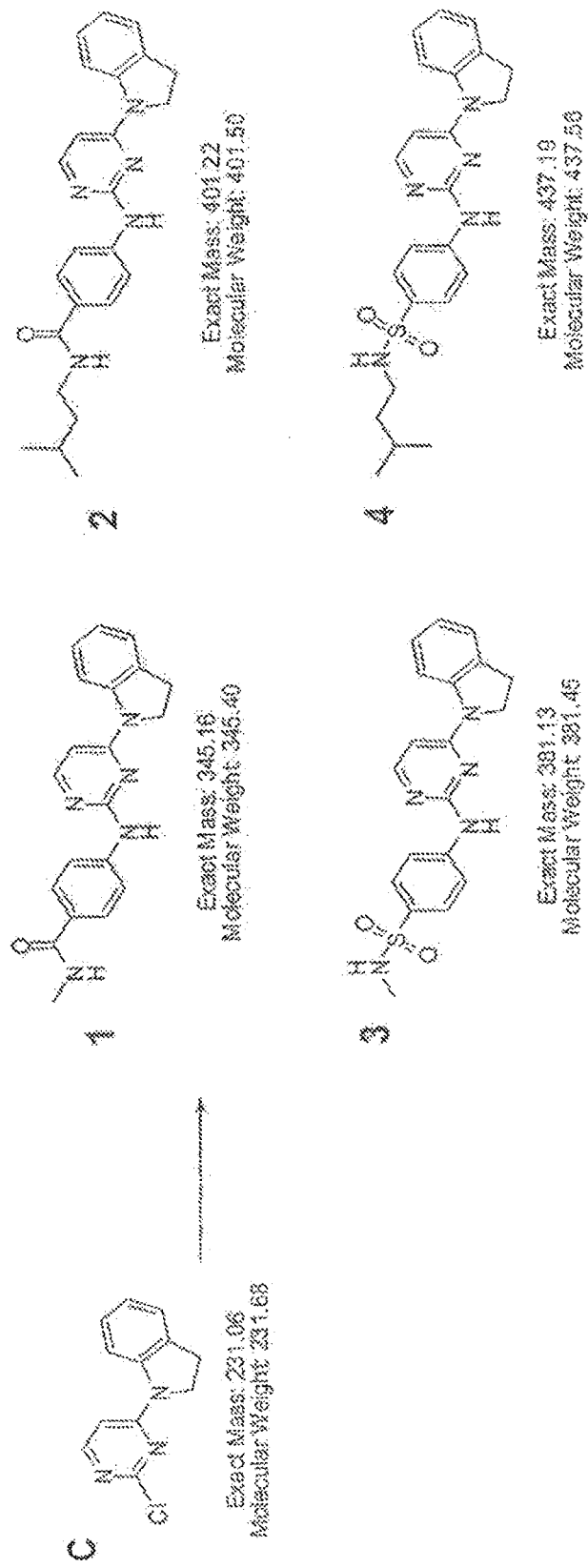
Figure 6F:
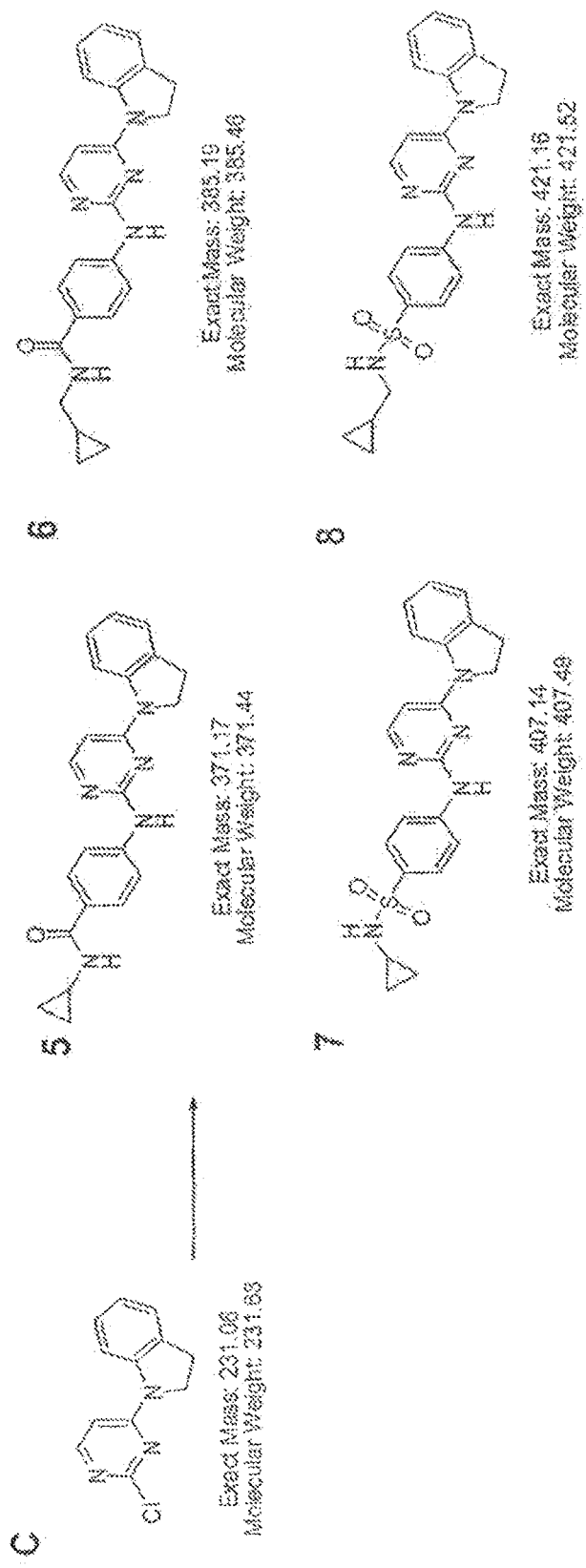
Figure 6C:
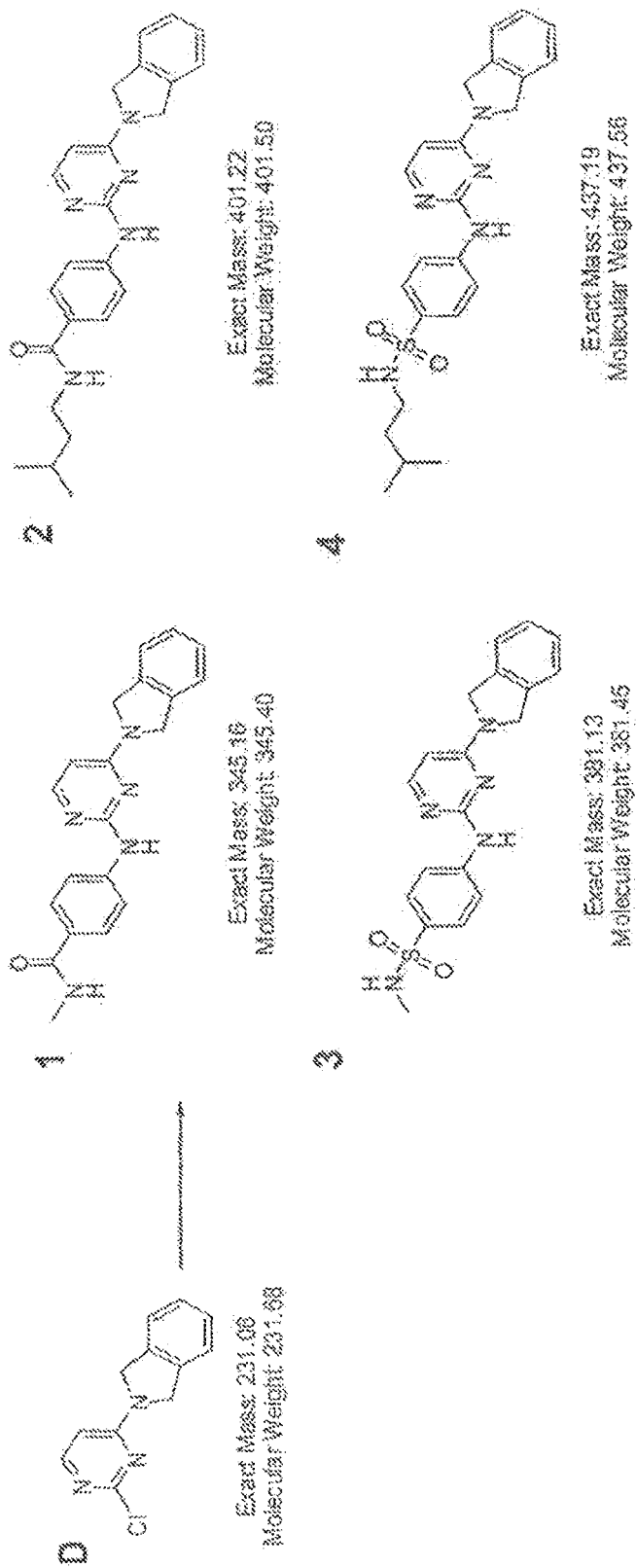
Figure 6H:
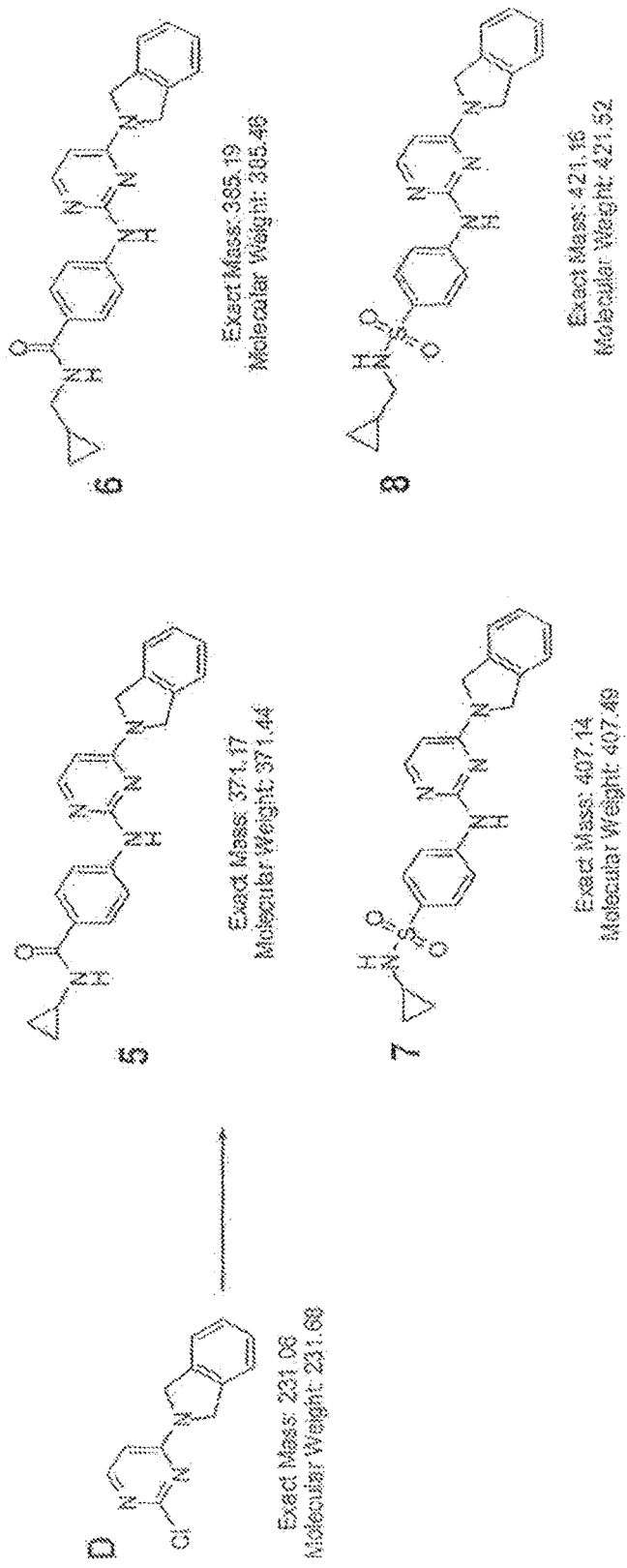
Figure 6I:
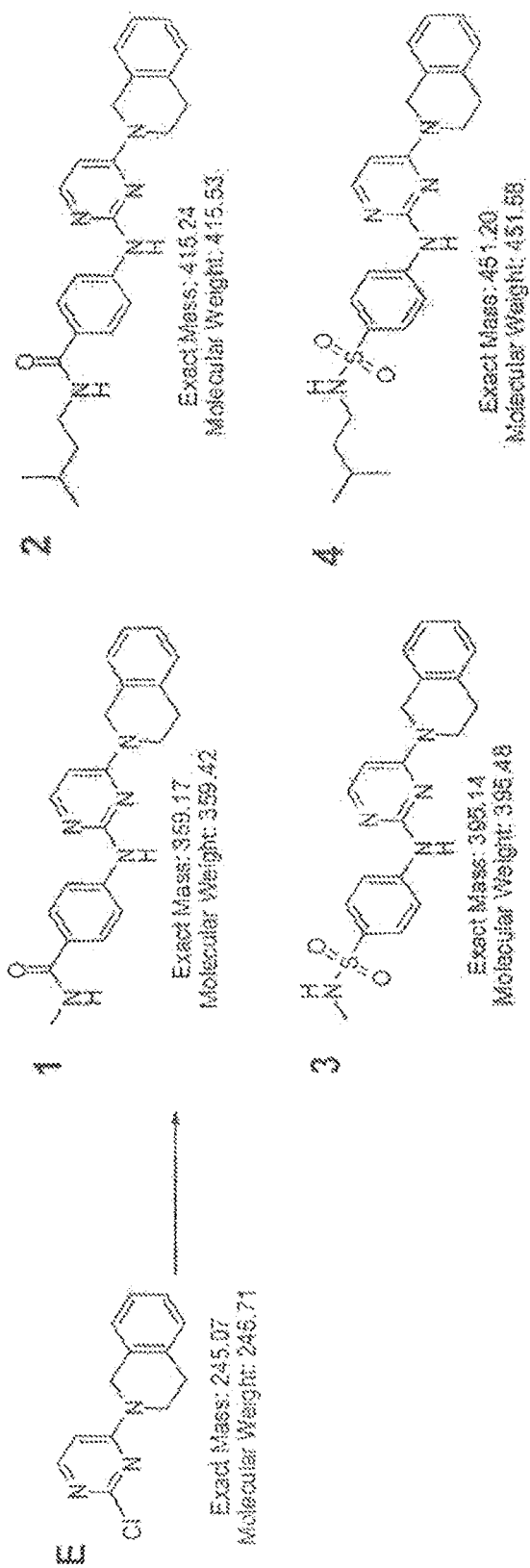
Figure 6J:
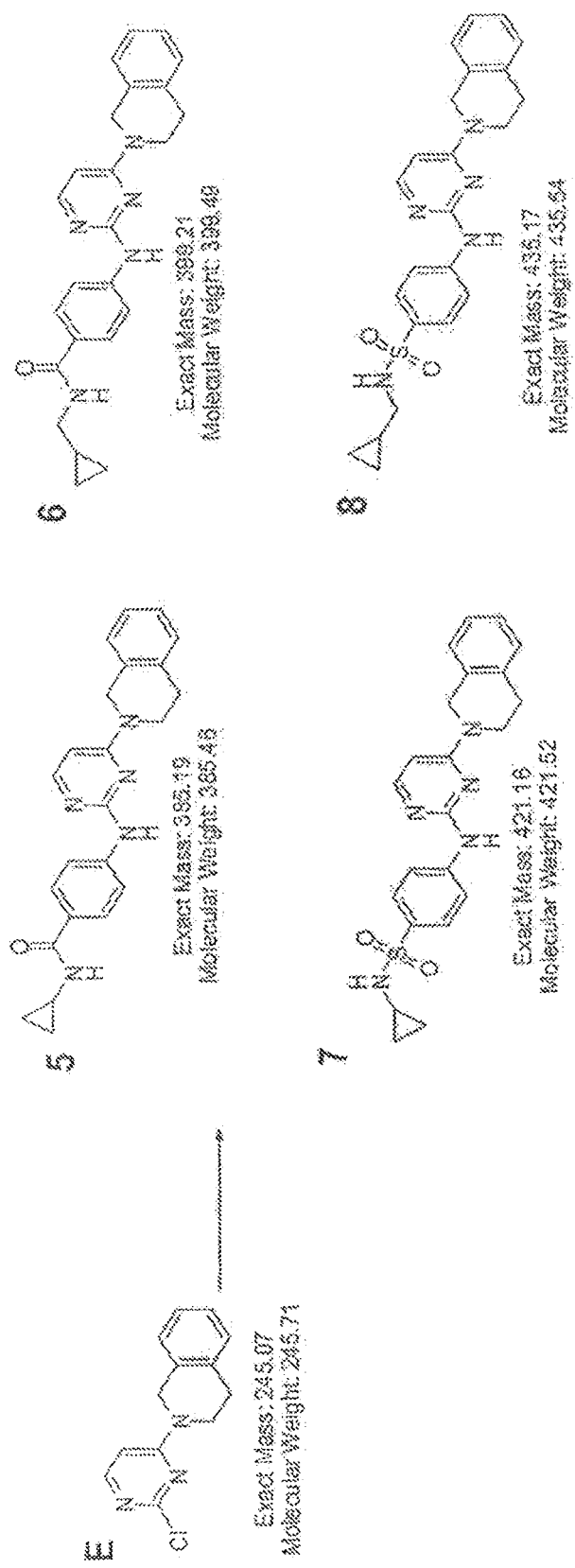
Figure 6K:
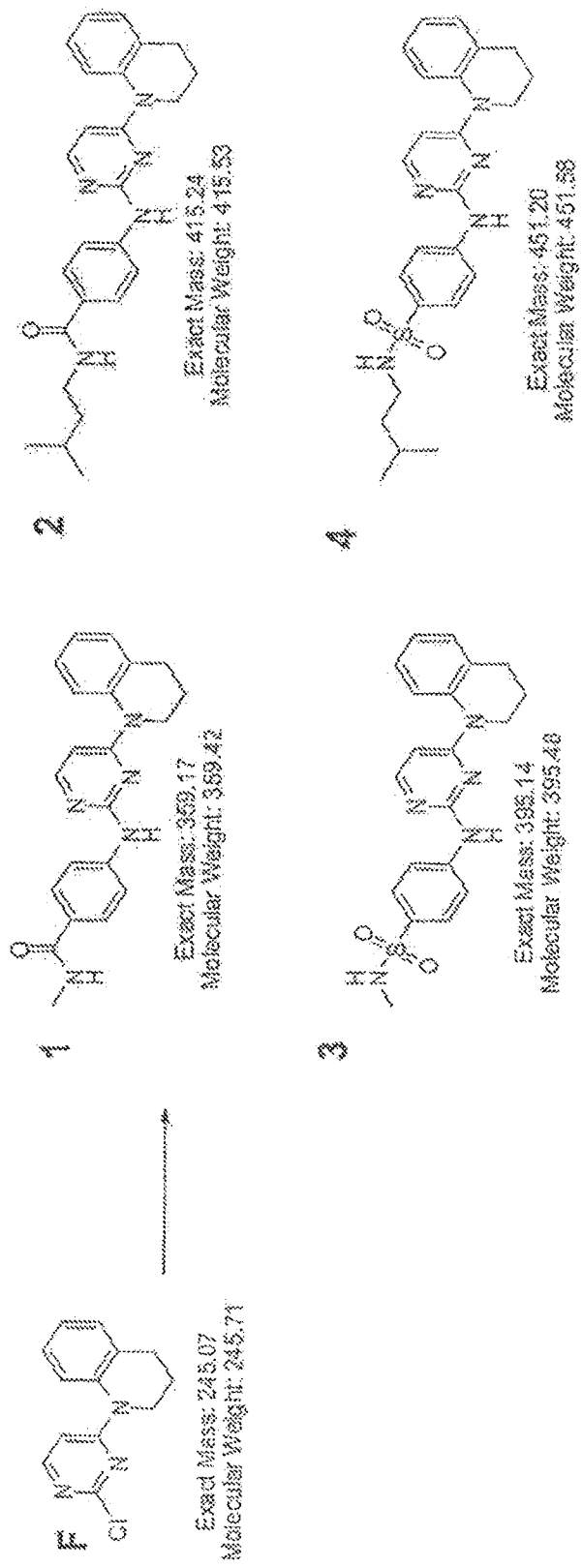
Figure 6L:
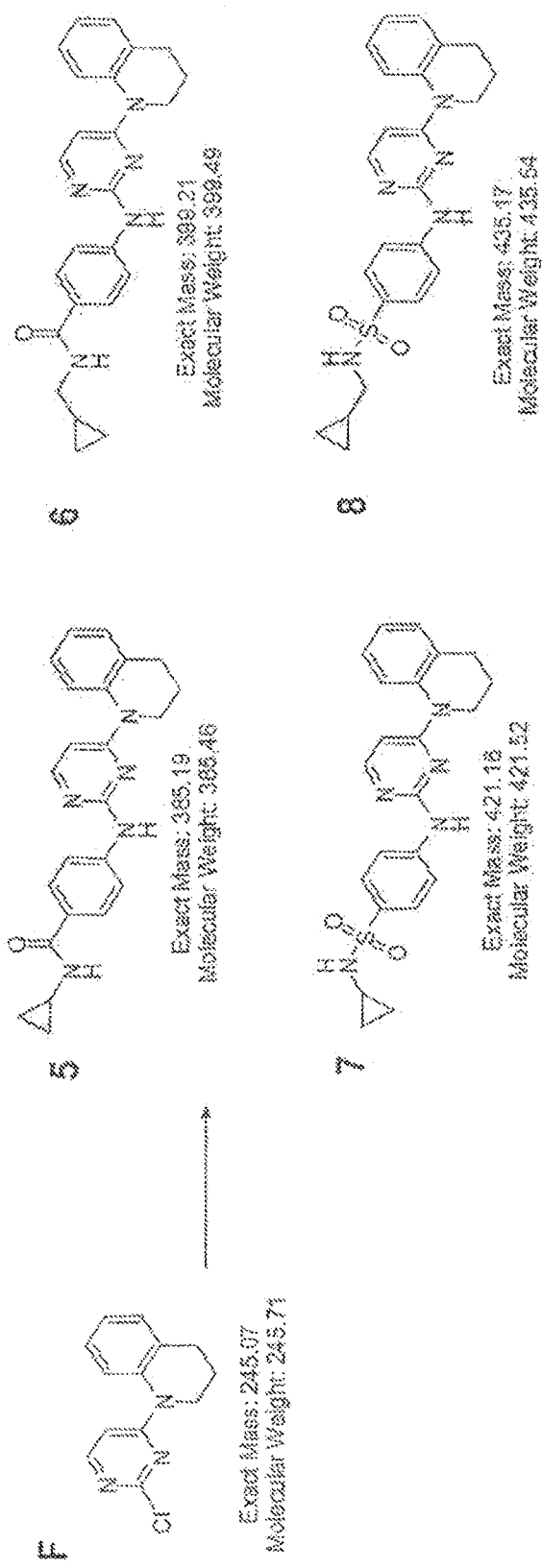
Figure 6M:
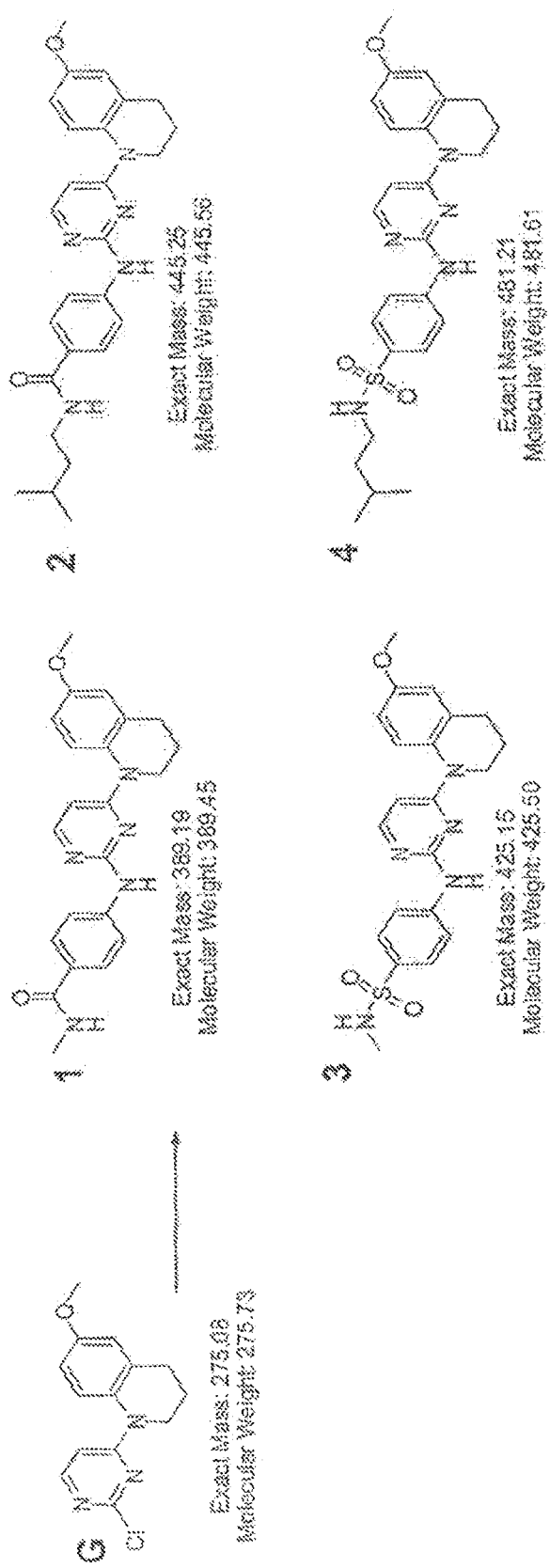
Figure 6N:
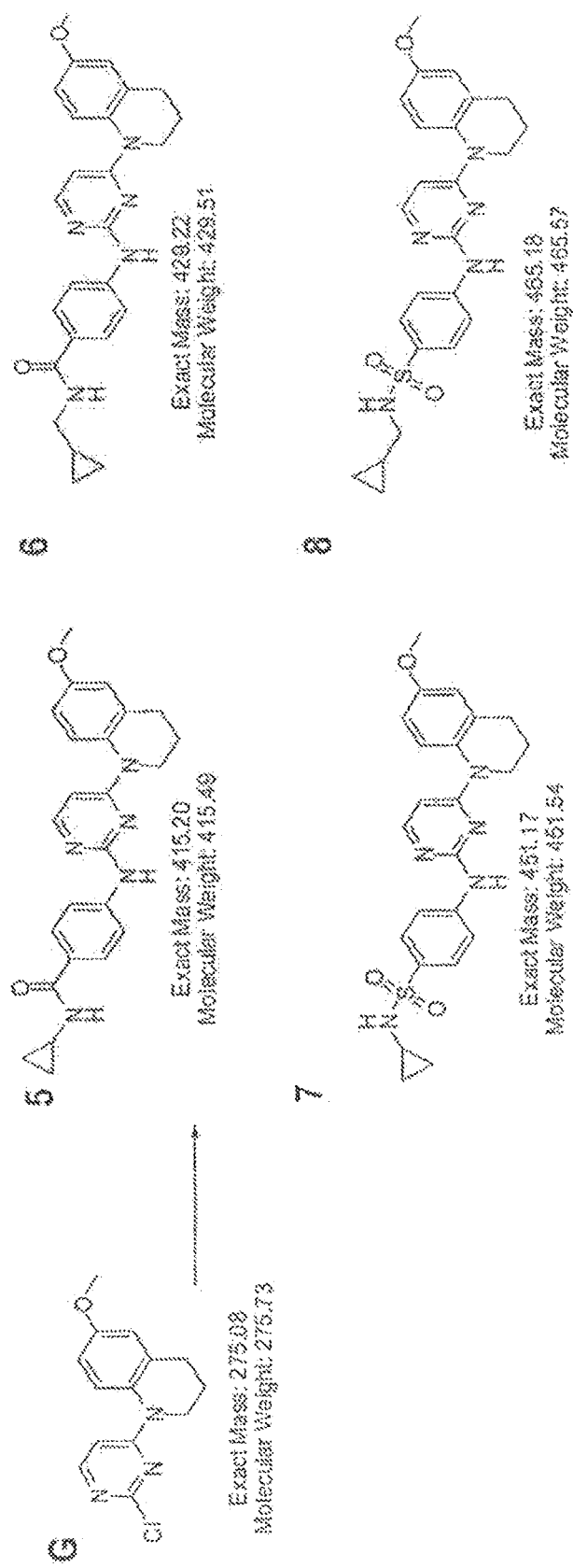
Figure 60:
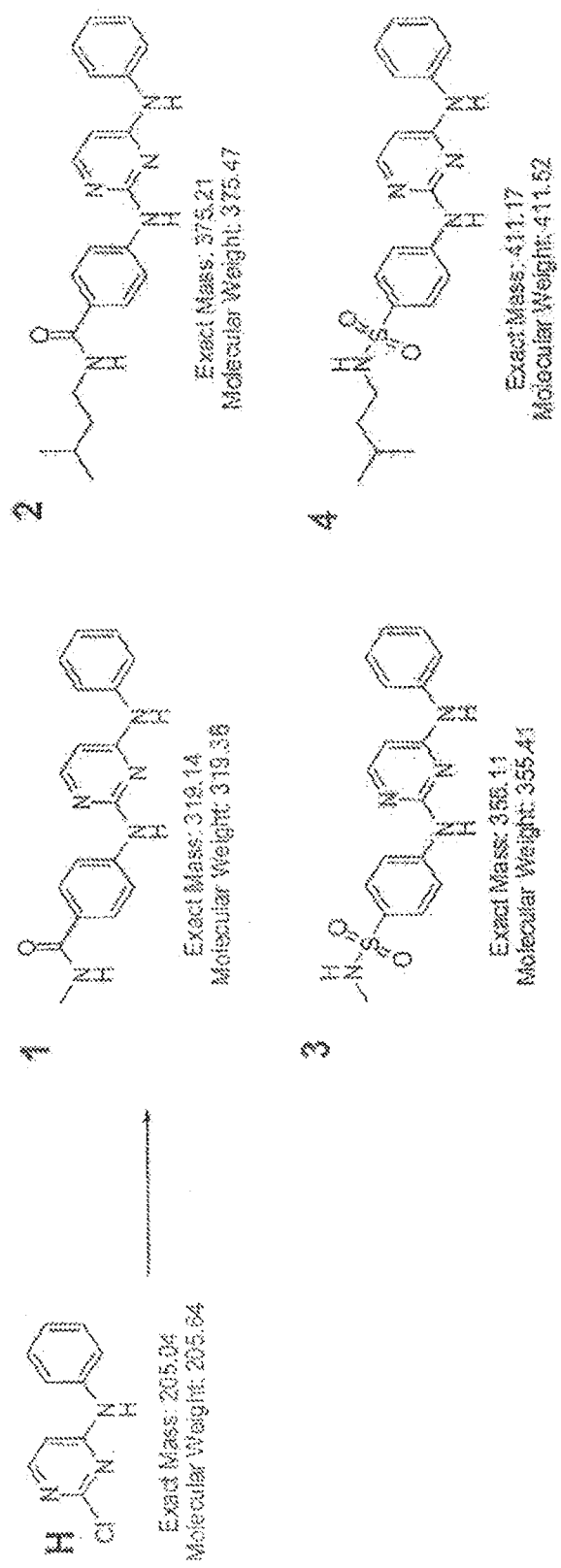
Figure 6P:
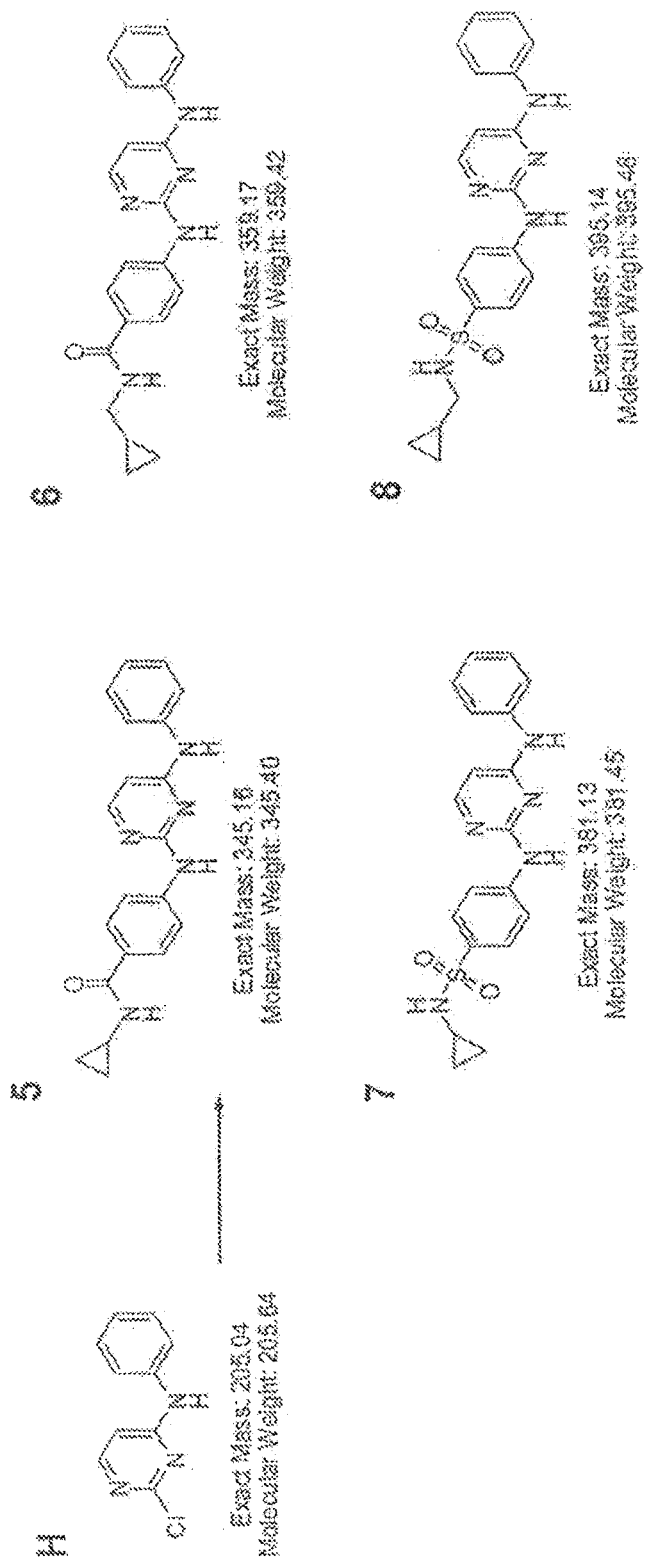
Figure 6Q:
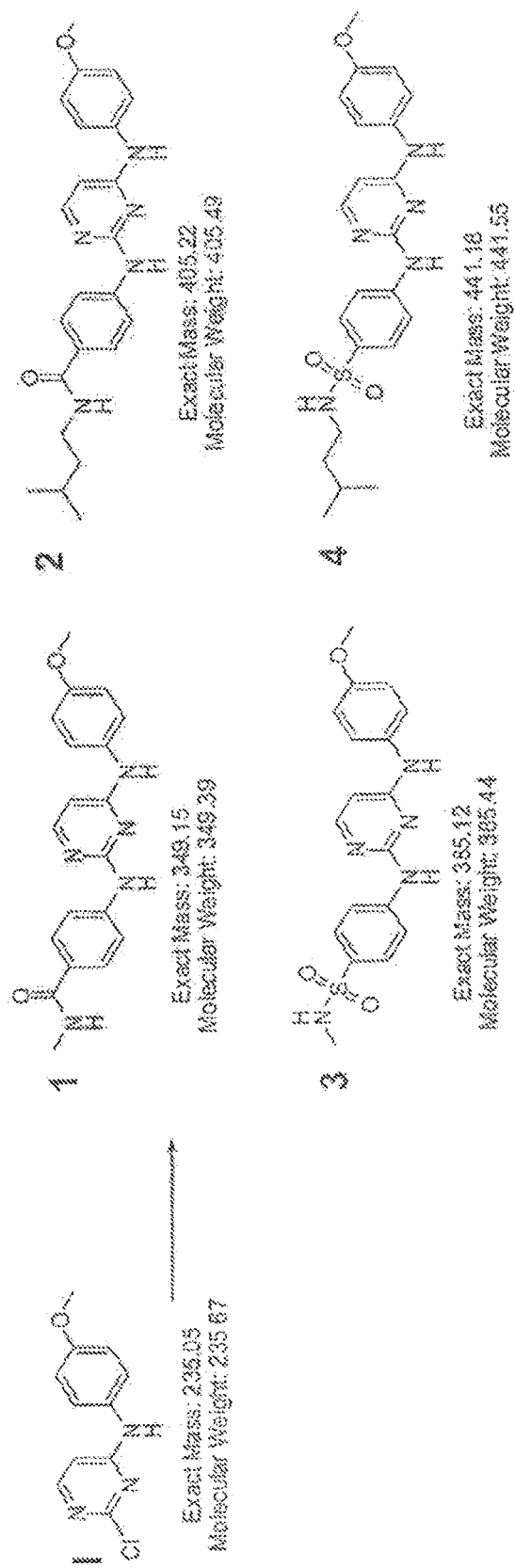
Figure 6R:
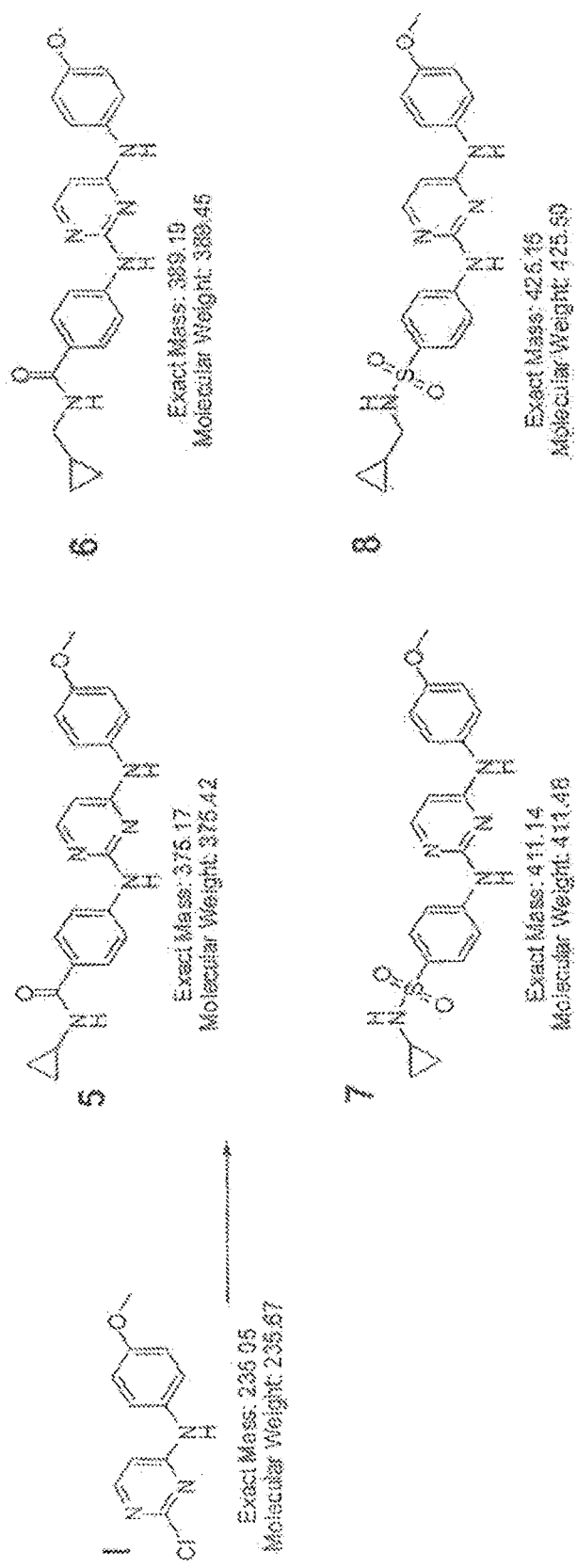
Figure 6S:
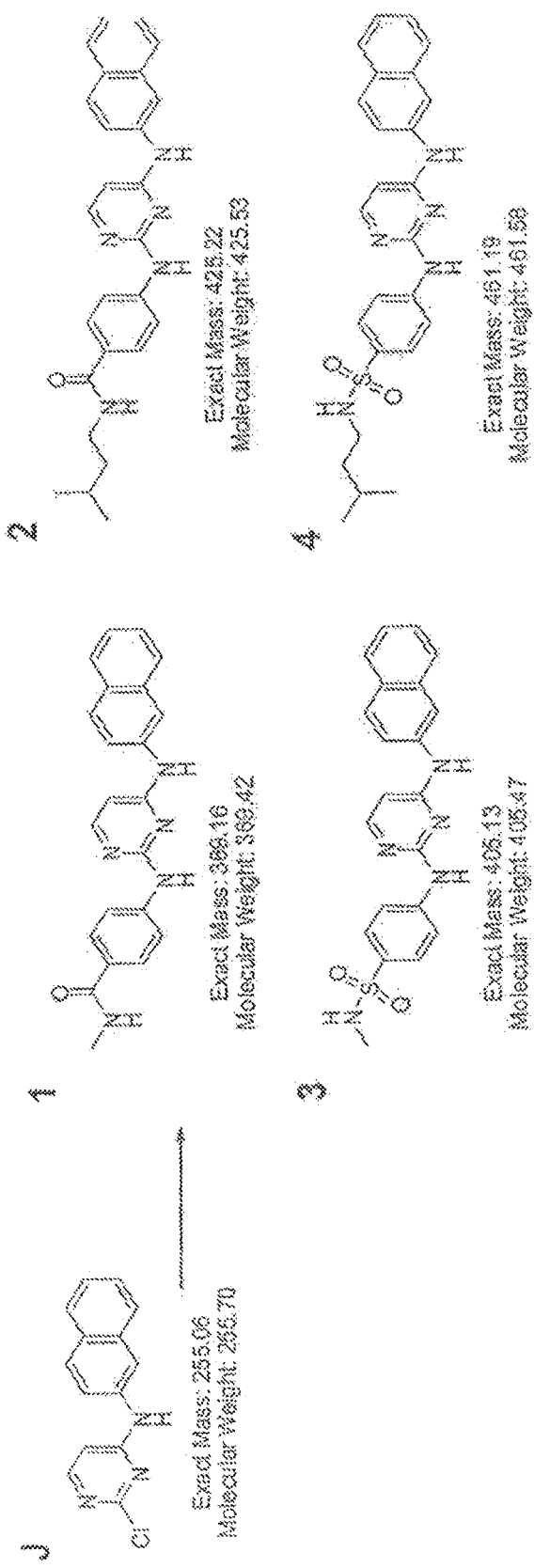
Figure 6T:
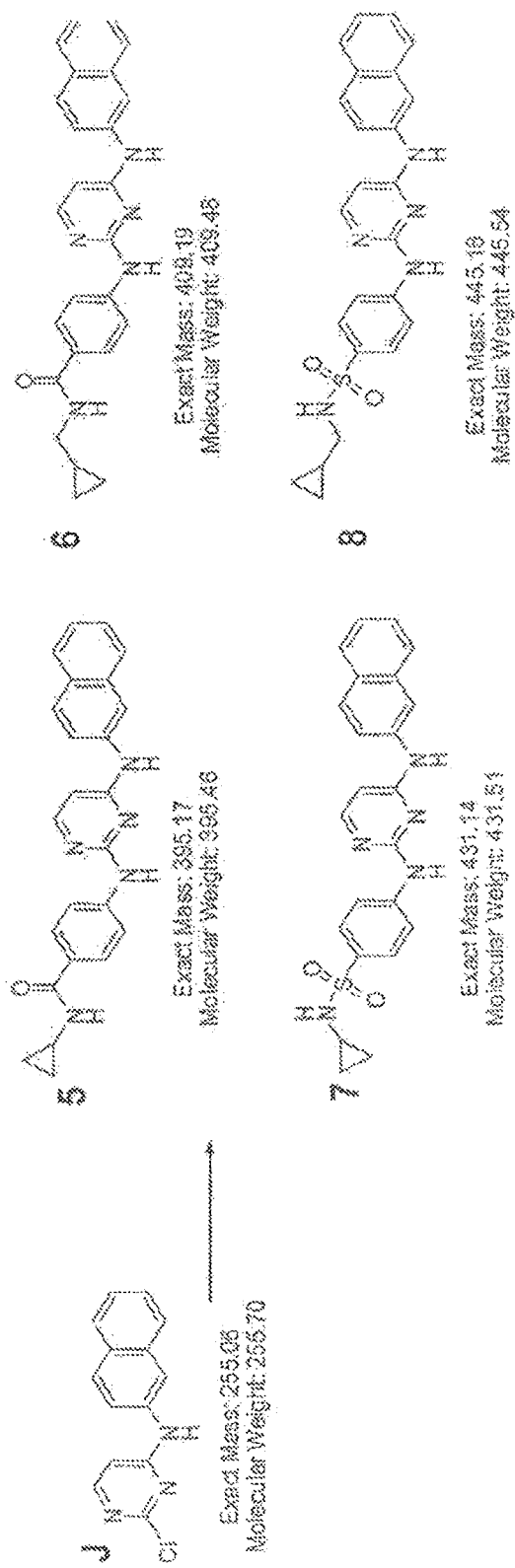
Figure 6U:
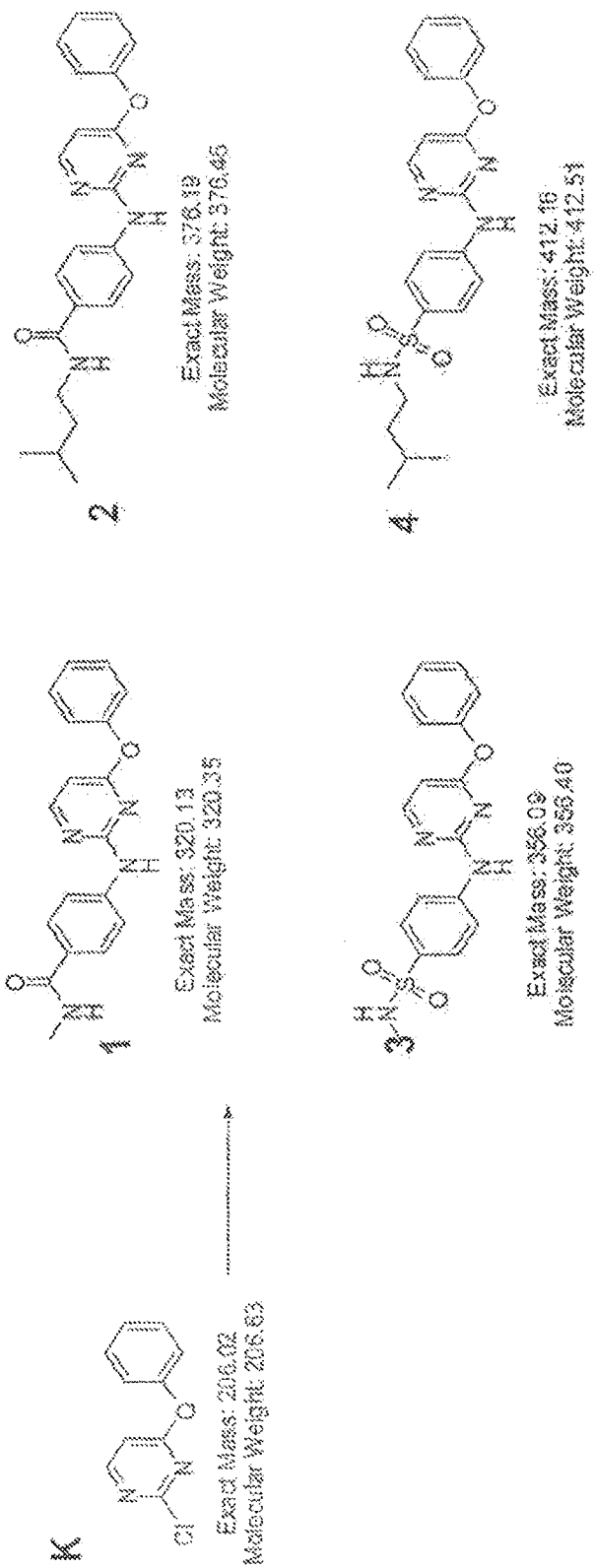
Figure 6V:
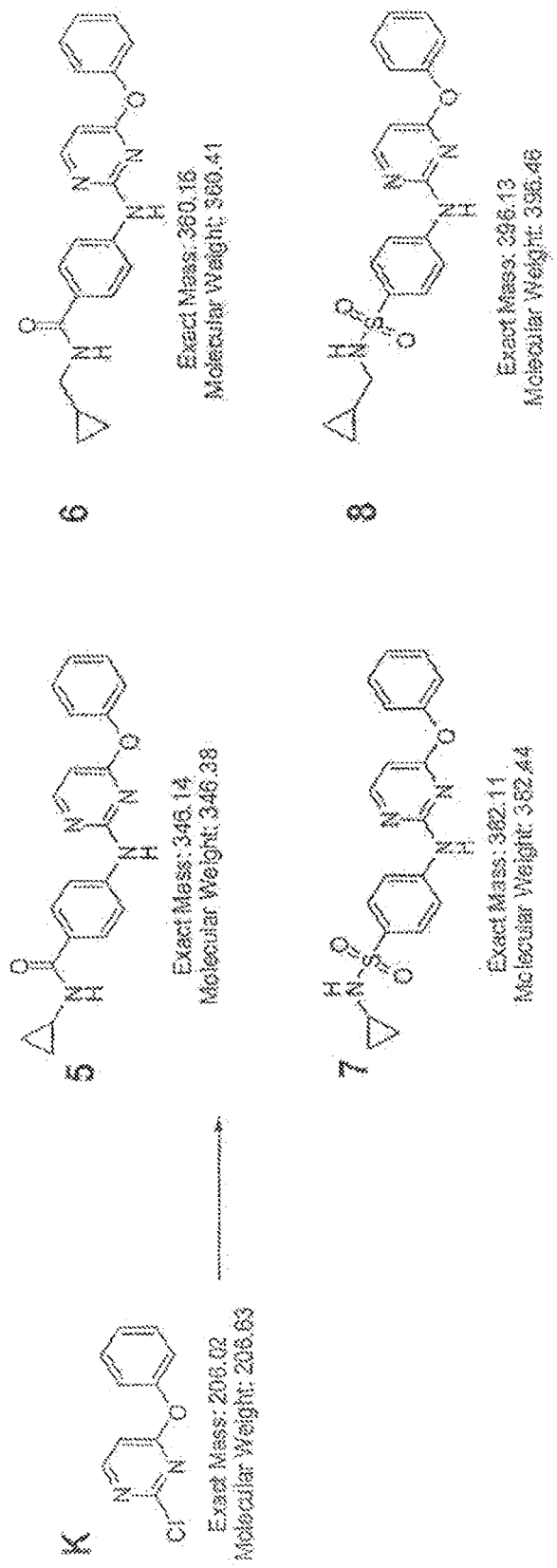
Figure 6W:
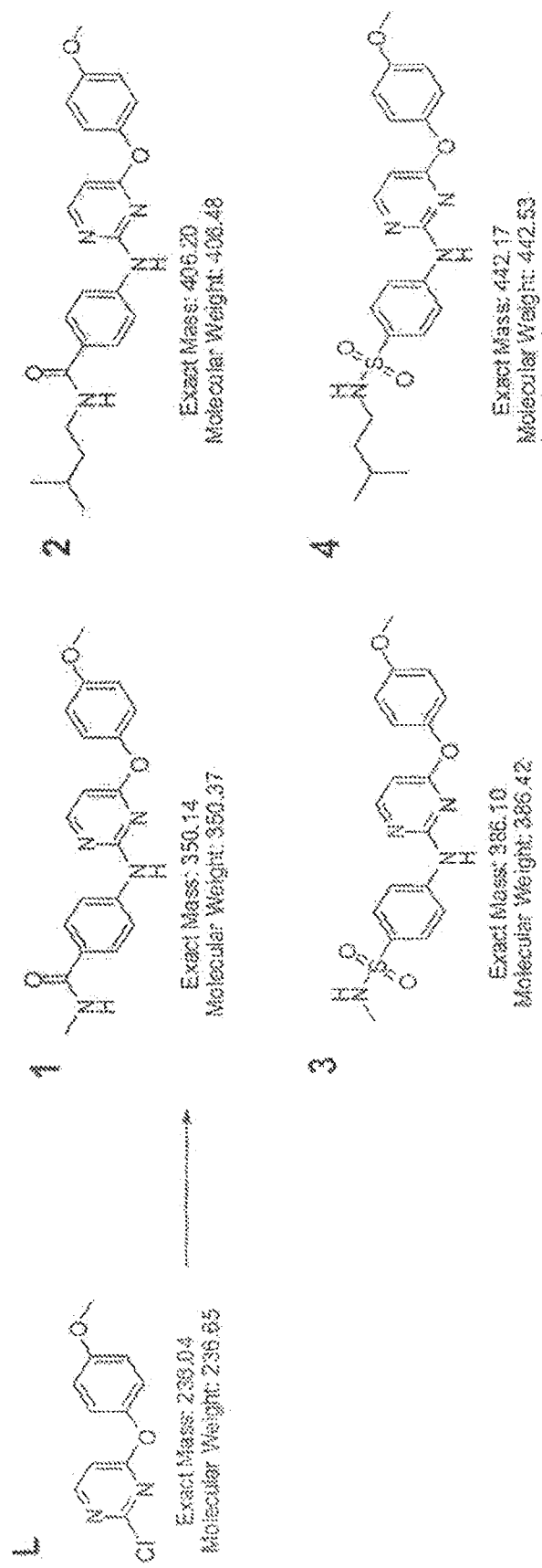
Figure 6X:
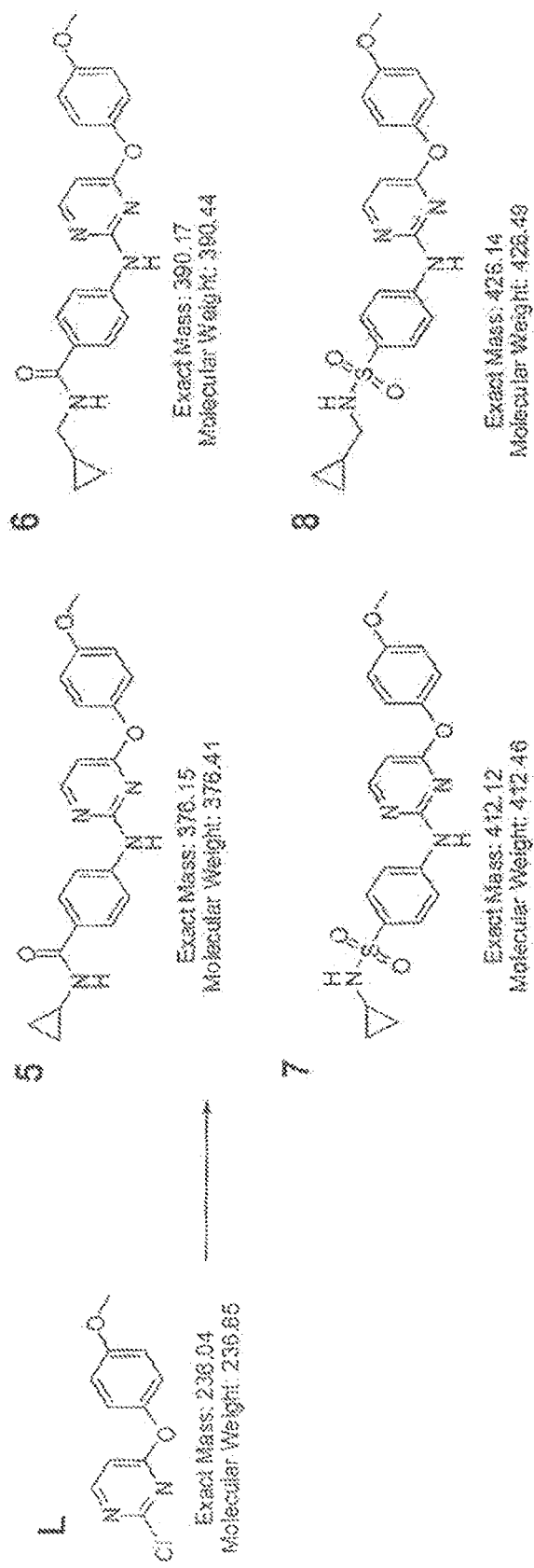
Figure 6Y:
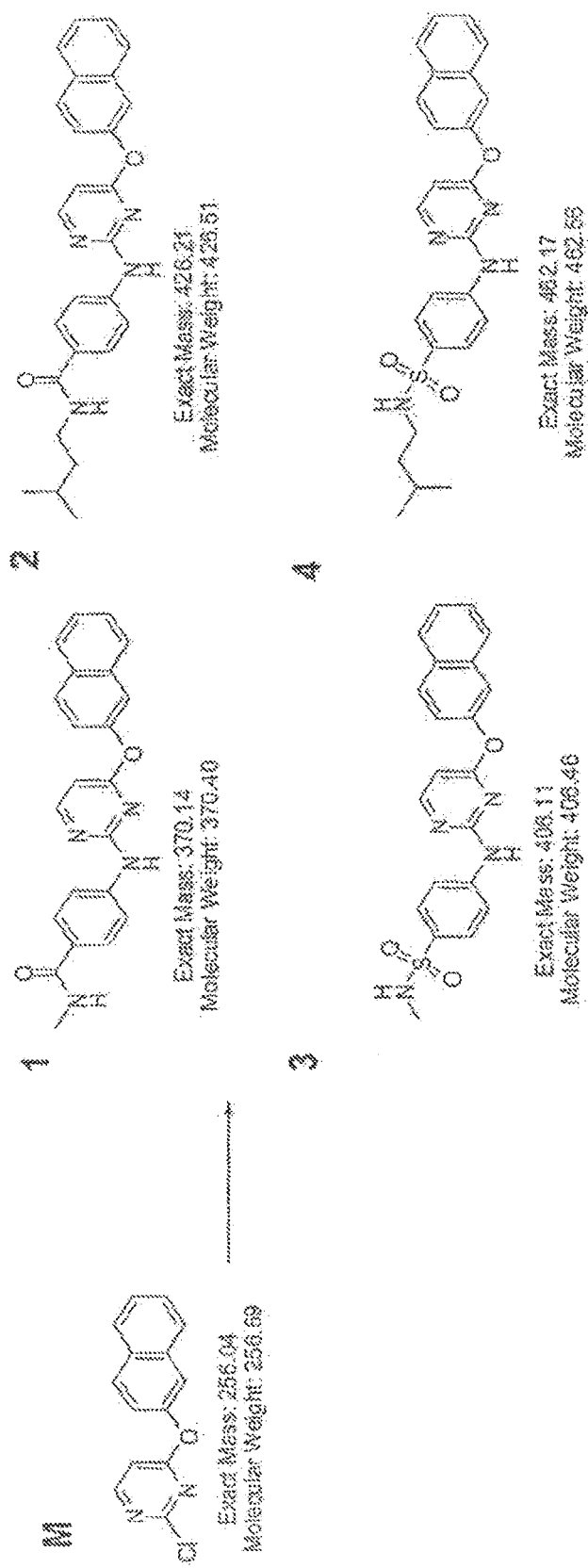
Figure 6Z:
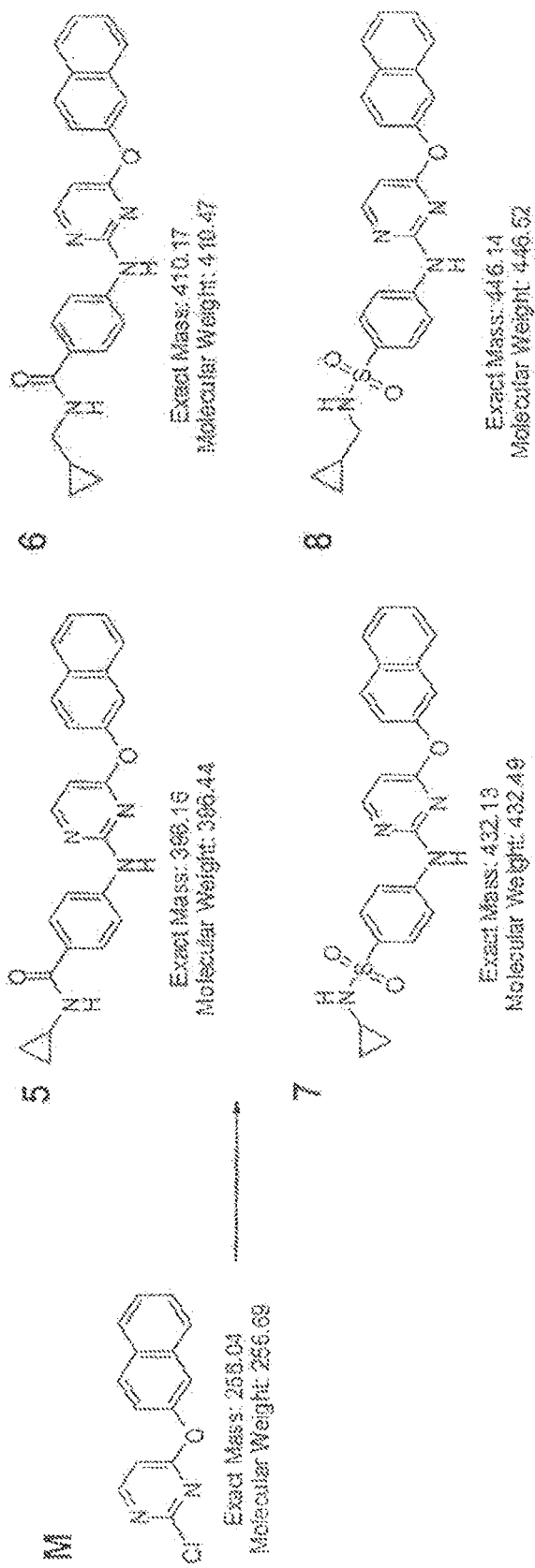
Figure 6A:
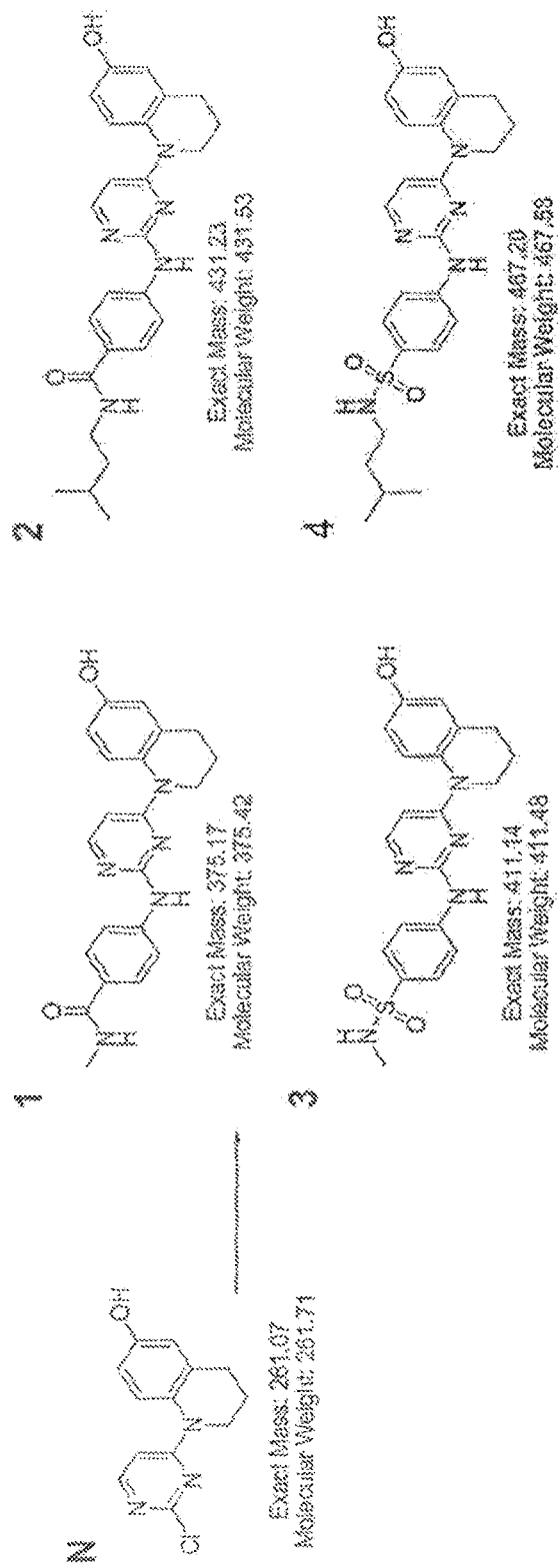
Figure 6A:
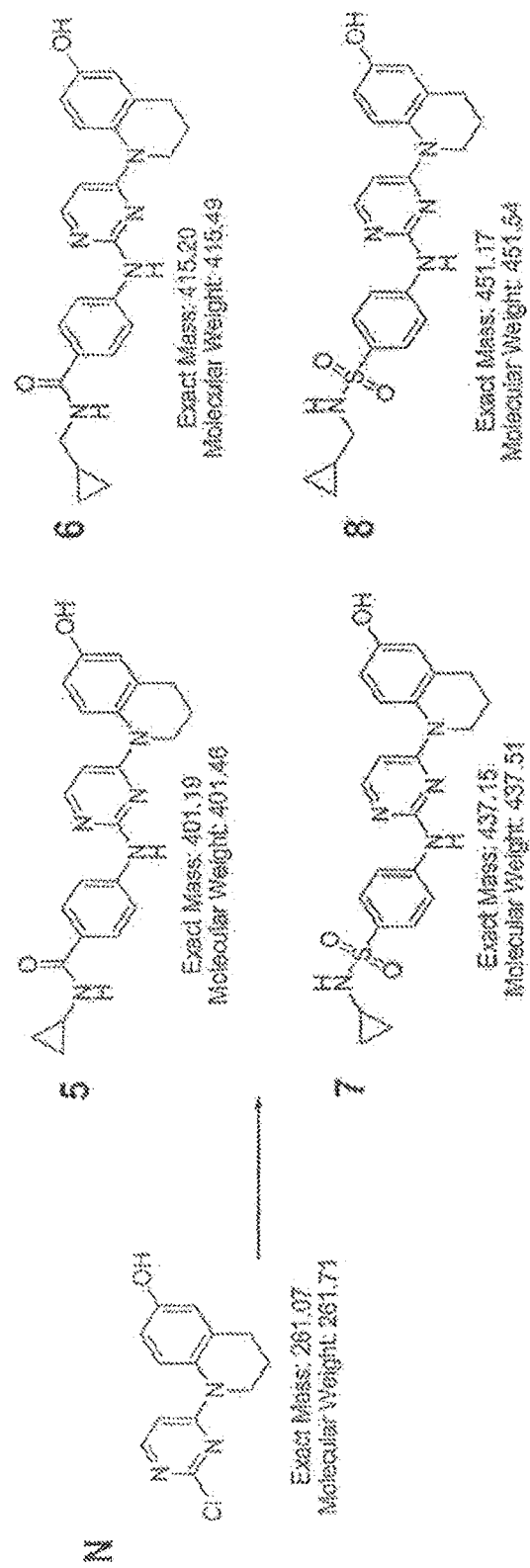
Figure 6A:
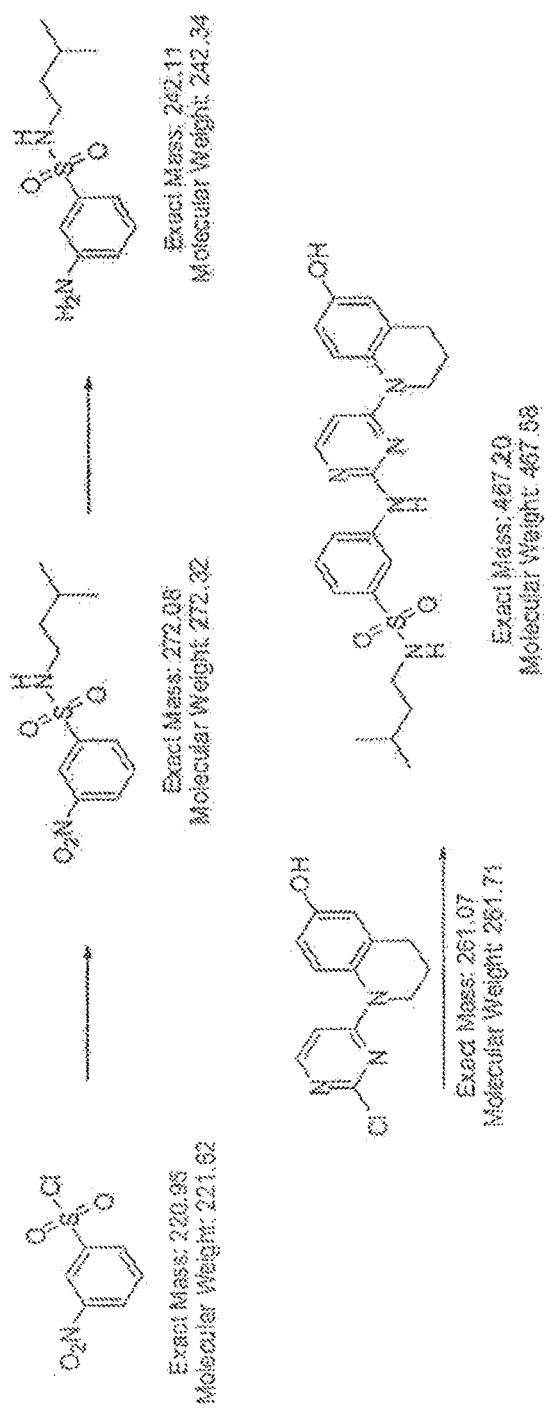

Interplay between physical/structural environment and growth factor plays a very important role in cell fate regulation (Comoglio, P. M., Boccaccio, C., & Trusolino, L., Curr Opin Cell Biol 15 (5):565-571 (2003)). To examine whether growth factors are involved in integrin-mediated hESC survival, we treated dissociated hESCs with Tzv or Ptn together with individual highly specific growth factor receptor inhibitors. We found that chemical inhibition of FGFR, IGFR, EGFR1 or Erb2 greatly diminished survival promoting effect induced by Tzv or Ptn treatment (FIG. 4a). In addition, Ptn significantly increased the phosphorylation of growth factor receptor, suggesting that engagement of growth factor receptors is required for integrin-mediated cell survival (FIG. 4b). Similarly inhibition of FGFR, IGFR, EGFR1 or Erb2 also greatly abolished Tzv-induced hESC survival in suspension culture. Furthermore, Tzv induced binding of E-cadherins to EGFR1 and ERB2, indicating the important role of growth factor receptors in E-cadherin-mediated cell survival (FIG. 4c, d).

Phosphatidylinositol-3-kinase (PI-3K) signaling and MAPK/ERK are major regulators for hESC self-renewal (Armstrong, L. et al., Hum Mol Genet 15 (11): 1894-1913 (2006); Paling, N. R. et al., J Biol Chem 279 (46):48063-48070 (2004); Pyle, A. D., Lock, L. F., & Donovan, P. J., Nat Biotechnol 24 (3):344-350 (2006); Li, J. et al., Differentiation 75 (4):299-307 (2007)). Phosphorylation of ERK and AKT, a downstream effector of PI-3K, were increased upon treatment of dissociated hESCs with Ptn, and this increase was abolished by integrin blocking antibody (FIG. 4e,f). Moreover, activation of AKT and ERK by Ptn was blocked by inhibitors of FGFR, IGFR, EGFR or Erb2 (FIG. 4g and data not shown). Chemical inhibition of PI-3K action significantly antagonized survival effect induced by Ptn (FIG. 4h). Inhibition of ERK did not have a dramatic effect on survival induced by Ptn but induced hESC differentiation (FIG. 4i). These results demonstrated that activation of PI-3K is a major survival signaling and activation of ERK is an anti-differentiation signaling generated by the niche through activation of growth factor receptors.

In summary, we identified two novel synthetic small molecules with distinct mechanisms of action from a high throughput phenotypic screen that greatly enhance hESC survival after single cell dissociation. Such chemical tools and newly identified biological tools through mechanistic characterizations (e.g. defined recombinant Ecad-Fc for hESC attachment in adherent culture; activating antibodies for enhanced cell survival and attachment) would enable more robust hESC culture and significantly facilitate applications of hESCs such as gene targeting or drug discovery. More importantly, in-depth mechanistic characterizations uncovered previously unrecognized niche mechanisms that are required to sustain hESC survival and proliferation. Such niche consists of E-cadherin-mediated interaction between hESC themselves, integrin-mediated cell-ECM interaction, and growth factors. Earlier studies have pointed to an important role of growth factors on hESC self-renewal. However, full activation of growth factor signaling requires not only the presence of the growth factors and receptors but also an interaction with a particular microenvironment. When this physical/structural environment is destroyed, growth factors alone are not sufficient for self-renewal of ESCs.

Recently, it was reported that differentiated fibroblasts generated from hESCs in self-renewal culture created an in vitro niche for hESCs (Bendall, S. C. et al., Nature 448 (7157): 1015-1021 (2007)). Under our and others' chemically defined medium conditions, we very rarely observe such differentiated cells in long-term culture, suggesting that such artificial niche might be created due to the media differences. Nevertheless, our studies reveal unique cell-autonomous (i.e. cell-cell interaction) and non cell-autonomous (i.e. cell-ECM and -growth factor) niche mechanisms for hESC survival and self-renewal, which may likely play important roles in controlling adult stem cell fate in vivo.

Cell-cell dissociation by trypsin led to not only destabilization of E-cadherins but also inactivation of integrins, indicating that signaling which maintains integrin activity is sensitive to enzymatic treatment. Feeder cell-conditioned media (with growth factor-rich serum) didn't provide much protection against cell death after single cell dissociation. In addition, the fact that high density cell seeding also induces an increase in cell adhesion/survival suggests that signaling required to maintain integrin activity may not come from secreted factors but instead from physical cell-cell interactions. Tzv inhibits endocytosis of E-cadherin, and thus protects cells from death in suspension. Similarly, by inhibiting endocytosis, Tzv may maintain integrin activity by stabilizing signaling from the cell surface. On the other hand, Ptn may mimic the downstream signaling from physical cell-cell interaction to activate PKC. Future target identification of Ptn may shed new light on the mechanism by which cell-cell adhesion regulates cell-ECM interaction. Our research also exemplified the feasibility and advance of high throughput chemical screening in stem cell studies. Further development and application of such chemical approach in stem cells will undoubtedly lead to the identification of additional novel small molecules and mechanistic insight for precisely controlling cell fate in vitro and in vivo.

Methods

Cell Culture

Human ESC lines H1, HUES7 and HUES9 were cultured on irradiated MEF feeder cells in DMEM-F12 supplemented with 2 mM L-glutamine, 1x nonessential amino acids, 20% serum replacement (Invitrogen) and 10 ng/ml basic Fibroblast growth factor (Invitrogen). Chemically-defined and feeder-free hESC culture was described previously (Yao, S. et al., Proc Natl Acad Sci USA 103 (18):6907-6912 (2006)). Briefly, hESCs were grown on Matrigel-coated tissue culture plates in N2B27-CDM (DMEM-F12 supplemented with 1×N2 supplements, 1x B27 supplements, 2 mM L-glutamine, 0.11 mM 2-mercaptoethanol, 1x nonessential amino acids, and 0.5 mg/ml BSA (fraction V)) and 20 ng/ml bFGF. Human ESCs were passaged every 5-6 days with 0.05% trypsin.

For clonal survival assays, single hESCs were diluted to clonal density and plated onto 96-well Matrigel-coated plate. For low-density survival assays, 500 cells were plated onto 96-well Matrigel-coated plate. To visualize hESC colonies, cultures were fixed in 4% paraformaldehyde in PBS for 5 min, washed once in PBS, then stained for alkaline phosphatase activity as described in manufacturer's instructions. ALP positive colonies were counted on an inverted microscope.

Reagents

ALP detection kit and integrin antibodies were from Chemicon. AG825 (Erb2 inhibitor), AG1478 (EGFR inhibitor), PPP (IGFR1 inhibitor) were purchased from Calbiochem. Antibodies raised against the intracytoplasmic tail of E-cadherins (Transduction Laboratories, Lexington, Ky.) were used for immunoprecipitation. The antibody TS2/16 was from Pierce. Antibodies to the extracellular domain of E-cadherin molecule were from Zymed (Carlsbad). Antibodies against extracellular signal-regulated kinase/MAPK, EGFR1, ERB2, GADPH and phosphorylated form of AKT were from Cell Signaling. Mouse monoclonal anti-phosphotyrosine (4G-10 clone) was from Upstate Biotechnology. Ptn and Tzv were added to culture medium at 2 μM.

High-Throughput Chemical Screen.

The trypsinable hESC lines HUES7 or HUES9 were used for the screen. hESCs were cultured in chemically-defined media on the Matrigel-coated plate as described above. Then cells were harvested by trypsin. hESCs were plated at 4,000 cells per well onto Matrigel-coated 384-well plates. After 1 h when cells settled down, compounds from a library of 50,000 discrete heterocycles were added to each well (2 μM final concentration). After an additional 6 days of incubation, in which media and compounds were changed at day 3, cells were stained for ALP expression and examined for compact colony morphology. Immunostaining analysis.

Immunostaining was performed as described previously (Yao, S. et al., *Proc Natl Acad Sci USA* 103 (18):6907-6912 (2006)). Briefly, cells were fixed with 4% paraformaldehyde at room temperature (RT) for 15 min. The cells were then incubated at RT in blocking buffer for 1 hour. Primary antibody incubation was carried overnight at 4° C. The following commercially available antibodies were used at a concentration of 1:100 in blocking buffer: anti-SSEA4, anti-Oct4 (Chemicon??) anti-Nanog (Chemicon). The staining was visualized using secondary antibodies conjugated to FITC, cy3 or cy5 (Jackson ImmunoResearch).

Teratoma Formation and Karyotyping.

Teratoma formation experiments were performed by injecting 3-5 million hESCs (maintained in the presence of compounds Tvz or Ptn) under the kidney capsule of nude mice. After 4-5 weeks, all mice developed teratomas, which were removed and then immunohistologically analyzed by The Scripps Research Institute Research Histology Service and Animal Resources. Compounds treated cells were karyotyped by standard G-banding at the Children's Hospital Oakland, Cytogenetics Laboratory. No chromosomal abnormality was found in the 10 randomly picked nuclei.

TUNEL Assay

The hESCs under different treatments were dissociated by trypsin and fixed by 4% paraformaldehyde. And the staining was carried out according to the manufacturer's instructions (MBL Laboratories, Watertown, Mass.). After staining, samples were analysed by flow cytometry using a FACS Calibur flow cytometer (BD).

Flow Cytometry Analysis

To assess the expression of E-cadherin, activated integrin and SSEA4, dissociated cells ($3 \times 10^5$) were washed with PBS and resuspended in PBS containing 2% goat serum. Cells were then incubated with the appropriate antibody for 1 h at 4° C., washed with the blocking solution, and labeled with FITC-conjugated secondary antibody for 30 min at 4° C. Cells were then washed and analyzed on a FACS Calibur flow cytometer.

Cell Adhesion Assay

Cell adhesion assays were performed in 96-well microtiter plates coated with Matrigel. After trypsin, hESCs were resuspended in the chemically-defined media containing the desired compounds. Cells were then added to the microtiter wells and incubated for 3 h at 37° C. Unbound and loosely bound cells were removed by shaking and washing, and the remaining cells were then fixed immediately. The wells were washed 3 times with 200 μl of $H_2O$, and attached cells were stained with Crystal Violet (Sigma). The absorbance of each well at 570 nm was then measured. For experiments with blocking antibodies, cells were pre-incubated with antibodies on ice for 30 min, and adhesion assays were performed in the presence of antibodies. Each sample was assayed independently for three times.

Endocytosis Assay hESCs were incubated with 1.5 mg/ml sulfosuccinimidyl 2-(biotinamido) ethyl-dithioproprionate (sulfo-NHS-SS-biotin) (Pierce Chemical Co.) on ice, followed by washing and quenching. Endocytosis of E-cadherin was initiated by $Ca^{2+}$ depletion and 37° C. incubation. Cells were then incubated in two 20-min washes of glutathione solution (60 mM glutathione, 0.83 M NaCl, with 0.83 M NaOH and 1% BSA added before use) at 0° C. which removed all cell surface biotin groups. Remaining biotinylated proteins were sequestered inside cells by endocytosis and were therefore protected from glutathione stripping. Biotinylated proteins were recovered on streptavidin beads and analyzed by SDS-PAGE. E-Cadherins were detected by immunoblotting. Total level of surface E-cadherin before endocytosis was used as reference.

Example 2: Synthesis of N-benzyl-2-(pyrimidin-4-ylamino)thiazole-4-carboxamide (Thiazovivin)

Chemical Synthesis

Using the chemical synthesis examples presented below and chemical synthesis methods generally known in the art, one of skill is capable of making the compounds disclosed herein (e.g. the compounds of Formulae (I) to (VI)).

All chemicals obtained commercially were used without further purification. NMR spectra were recorded on a Bruker (400 MHz) instrument. Chemical shifts (δ) were measured in ppm and coupling constants (J) are reported in Hz. LCMS was performed by reverse-phase liquid chromatography-mass spectrometer Agilent 1100 LCMS system with API-ES ionization source. High pressure liquid chromatography was performed with C18 column with a linear gradient from 10% solvent A (acetonitrile with 0.035% trifluoroacetic acid) in solvent B (water with 0.05% trifluoroacetic acid) to 90% A in seven and half minutes, followed by two and half minutes elution with 90% A.

Synthesis of N-benzyl-2-(pyrimidin-4-ylamino)thiazole-4-carboxamide (Thiazovivin)

Benzyl amine was loaded to 4-formyl-3,5-dimethoxyphenoxymethyl functionalized polystyrene resin (PAL) via reductive amination to give PAL-benzyl amine resin. See, Ding, S.; Grey, N. S. Wu, X.; Ding, Q.; Schultz, P. G. *J Am. Chem. Soc.* 2002, 124, 1594-1596. A reaction flask containing PAL-benzyl amine resin (200 mg, 0.2 mmol), 2-bromothiazole-4-carboxylic acid (83 mg, 0.4 mmol), bis(2-oxo-3-oxazolidinyl)phosphinic chloride (BOP-Cl) (153 mg, 0.6 mmol) and diisopropylethylamine (0.17 mL, 1 mmol) in DMF (3 mL) was shaken for 24 hr at room temperature. The resin was washed with methanol, dichloromethane and dried in vacuo to give PAL resin-N-benzyl-2-bromothiazole-4-carboxamide, which was then added to a flame-dried reaction vial, followed by 4-aminopyrimidine (95 mg, 1 mmol), $Pd_2(dba)_3$ (46 mg, 0.05 mmol), Xantphos (87 mg, 0.15 mmol) and NaO$^t$Bu (192 mg, 2 mmol). The vial was sure safe capped and degassed, then charged with argon and anhydrous dioxane (1.5 mL). The reaction was shaken for 24 hours at 90° C. The resin was washed with sodium diethyldithiocarbamate solution (0.05 M in DMF), methanol and dichloromethane and dried in vacuo. The resin was subsequently cleaved with cleavage cocktail TFA:CH$_2$Cl$_2$:H$_2$O (45:55:5) (2 mL) for 2 hr. The resin was filtered, the filtrate was collected and evaporated in vacuo to give the crude which was then purified by HPLC to give the title compound (30 mg, 48%).

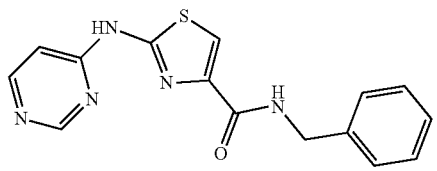 [SMILES: O=C(NCc1ccccc1)c1csc(Nc2ccncn2)n1]

N-Benzyl-2-(pyrimidin-4-ylamino)thiazole-4-carboxamide

Exact mass calculated for C$_{15}$H$_{13}$N$_5$OS: 311.1, found LCMS m/z=334.1 (M+Na$^+$).

$^1$H NMR (400 MHz, d$_6$-DMSO) 4.49 (d, J=6.3 Hz, 2H), 5.76 (s, 1H), 7.21-7.27 (m, 2H), 7.30-7.34 (m, 4H), 7.85 (s, 1H), 8.45 (t, J=6.3 Hz, 1H), 8.51 (d, J=6.1 Hz, 1H), 8.94 (s, 1H).

Example 3: Synthesis of Thiazovivin Derivatives

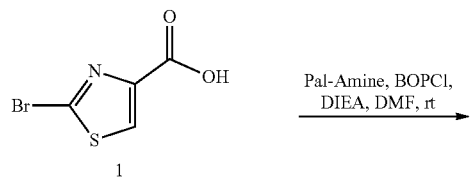

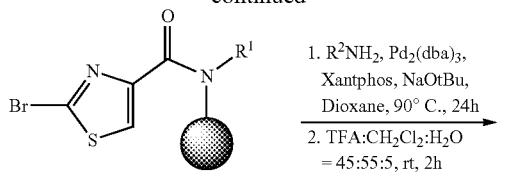

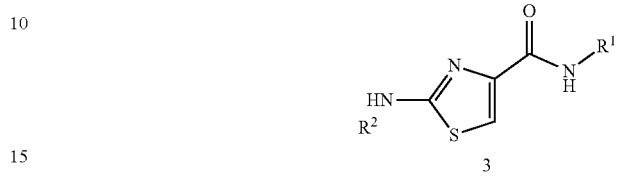

Appropriate amines R$^1$NH$_2$ were pre-loaded to 4-formyl-3,5-dimethoxyphenoxymethyl functionalized polystyrene resin (PAL) via reductive amination to give PAL-benzyl amine resin. A mixture of PAL-benzyl amine resin (200 mg, 0.2 mmol, 1.0 eq.), 2-bromothiazole carboxylic acid 1 (0.4 mmol, 2.0 eq.), bis(2-oxo-3-oxazolidinyl)phosphinic chloride (BOP-Cl) (0.6 mmol, 3.0 eq.) and diisopropylethylamine (1 mmol, 5.0 eq.) in anhydrous DMF (3 mL) was shaken for 24 hr at ambient temperature. The resin was washed with methanol, dichloromethane and dried in vacuo, which was then added to a flame-dried reaction vial, followed by corresponding R$^2$NH$_2$ (1 mmol, 5.0 eq.), Pd$_2$(dba)$_3$ (0.05 mmol), Xantphos (0.15 mmol) and NaO$^t$Bu (2 mmol, 10.0 eq.). The vial was sure safe capped and degassed, then charged with argon and anhydrous dioxane (1.5 mL). The reaction was shaken for 24 hours at 90° C. The resin was washed with sodium diethyldithiocarbamate solution (0.05 M in DMF), methanol and dichloromethane and dried in vacuo. The resin was subsequently cleaved with cleavage cocktail: TFA:CH$_2$Cl$_2$:H$_2$O=45:55:5 (2 mL) for 2 hr. The resin was filtered and the filtrate was collected and evaporated in vacuo to give the crude which was then purified by HPLC to give the desired title compound 3.

| Structure | Name | Data |
|---|---|---|
| 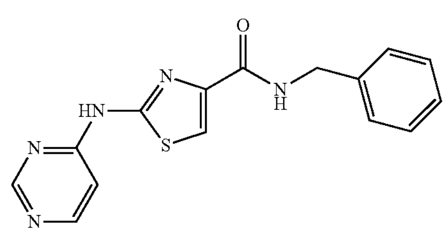 [SMILES: O=C(NCc1ccccc1)c1csc(Nc2ccncn2)n1] | N-benzyl-2-(pyrimidin-4-ylamino)thiazole-4-carboxamide | LC/MS Rt = 1.49 min, [MH$^+$] 312, [MNa$^+$] 334. |
| 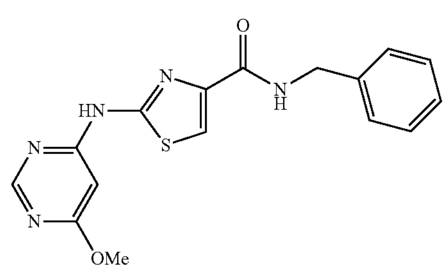 [SMILES: COc1cc(Nc2nc(C(=O)NCc3ccccc3)cs2)ncn1] | N-benzyl-2-(6-methoxypyrimidin-4-ylamino)thiazole-4-carboxamide | LC/MS Rt = 2.12 min, [MH$^+$] 342. |

-continued

| Structure | Name | Data |
|---|---|---|
| 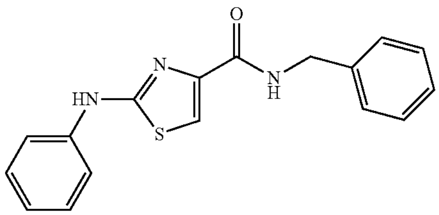 [SMILES: O=C(NCc1ccccc1)c1csc(Nc2ccccn2)n1] | N-benzyl-2-(phenylamino)thiazole-4-carboxamide | LC/MS Rt = 2.45 min, [MH$^+$] 310. |
| | N-benzyl-2-(pyridin-2-ylamino)thiazole-4-carboxamide | LC/MS Rt = 1.69 min, [MH$^+$] 311. |
| | N-benzyl-2-(pyridin-2-ylamino)thiazole-4-carboxamide | LC/MS Rt = 1.57 min, [MH$^+$] 311. |
| | N-benzyl-2-(pyridin-2-ylamino)thiazole-4-carboxamide | LC/MS Rt = 2.02 min, [MH$^+$] 312. |
| 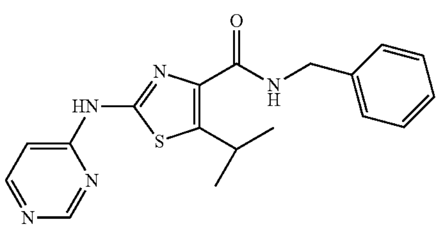 [SMILES: CC(C)c1sc(Nc2ccncn2)nc1C(=O)NCc1ccccc1] | N-benzyl-5-isopropyl-2-(pyrimidin-4-ylamino)thiazole-4-carboxamide | LC/MS Rt = 1.90 min, [MH$^+$] 354. |
| 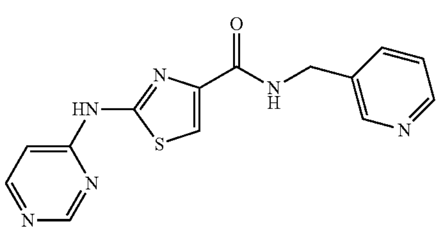 [SMILES: O=C(NCc1cccnc1)c1csc(Nc2ccncn2)n1] | N-(pyridin-3-ylmethyl)-2-(pyrimidin-4-ylamino)thiazole-4-carboxamide | LC/MS [MH$^+$] 312. |
| 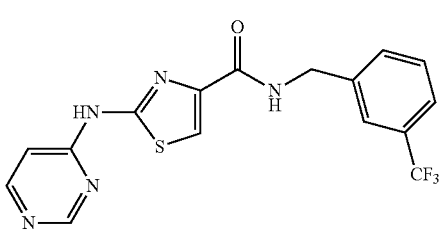 [SMILES: O=C(NCc1cccc(C(F)(F)F)c1)c1csc(Nc2ccncn2)n1] | 2-(pyrimidin-4-ylamino)-N-(3-(trifluoromethyl)benzyl)thiazole-4-carboxamide | LC/MS [M$^+$] 379. |

-continued

| Structure | Name | Data |
|---|---|---|
| 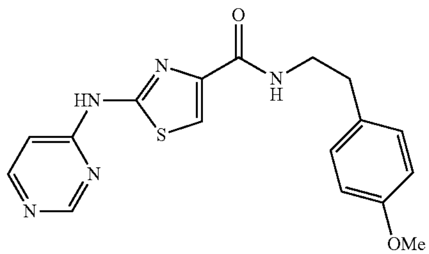 [SMILES: COc1ccc(CCNC(=O)c2csc(Nc3ccncn3)n2)cc1] | N-(4-methoxyphenethyl)-2-(pyrimidin-4-ylamino)thiazole-4-carboxamide | LC/MS [M+] 355. |
| 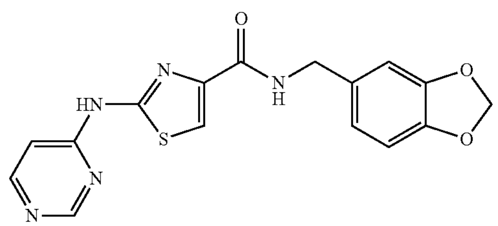 [SMILES: O=C(NCc1ccc2c(c1)OCO2)c1csc(Nc2ccncn2)n1] | N-(benzo[d][1,3]dioxol-5-ylmethyl)-2-(pyrimidin-4-ylamino)thiazole-4-carboxamide | LC/MS [MH+] 356. |
| 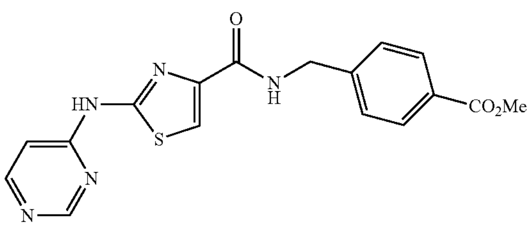 [SMILES: COC(=O)c1ccc(CNC(=O)c2csc(Nc3ccncn3)n2)cc1] | methyl 4-((2-(pyrimidin-4-ylamino)thiazole-4-carboxamido)methyl)benzoate | LC/MS [MH+] 370. |
| 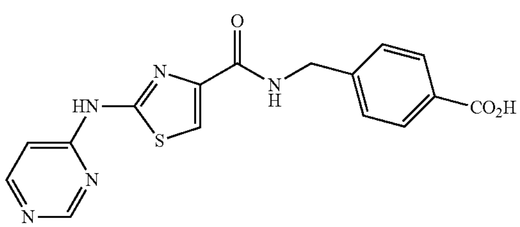 [SMILES: O=C(O)c1ccc(CNC(=O)c2csc(Nc3ccncn3)n2)cc1] | 4-((2-(pyrimidin-4-ylamino)thiazole-4-carboxamido)methyl)benzoic acid | LC/MS [MH+] 356. |
| 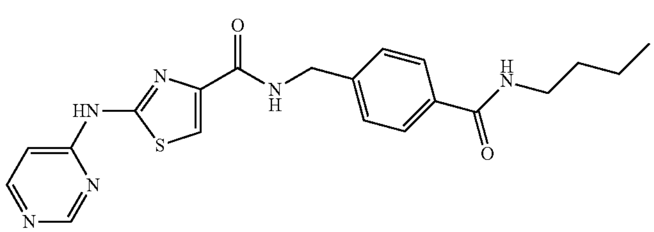 [SMILES: CCCCNC(=O)c1ccc(CNC(=O)c2csc(Nc3ccncn3)n2)cc1] | N-(4-(butylcarbamoyl)benzyl)-2-(pyrimidin-4-ylamino)thiazole-4-carboxamide | LC/MS [MH+] 411. |
| 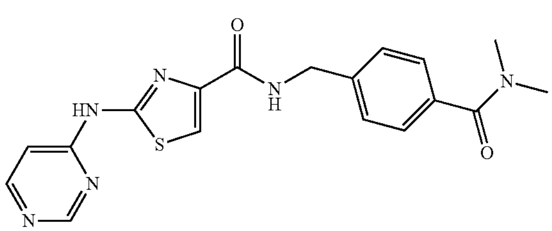 [SMILES: CN(C)C(=O)c1ccc(CNC(=O)c2csc(Nc3ccncn3)n2)cc1] | N-(4-(dimethylcarbamoyl)benzyl)-2-(pyrimidin-4-ylamino)thiazole-4-carboxamide | LC/MS [MH+] 383. |

| Structure | Name | Data |
|---|---|---|
| 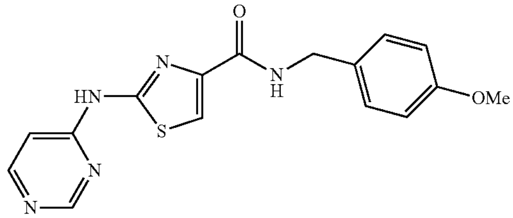 [SMILES: COc1ccc(CNC(=O)c2csc(Nc3ccncn3)n2)cc1] | N-(4-methoxybenzyl)-2-(pyrimidin-4-ylamino)thiazole-4-carboxamide | LC/MS [MH+] 342. |
| 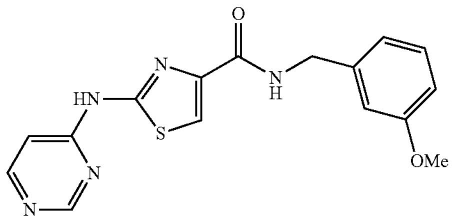 [SMILES: COc1cccc(CNC(=O)c2csc(Nc3ccncn3)n2)c1] | N-(3-methoxybenzyl)-2-(pyrimidin-4-ylamino)thiazole-4-carboxamide | LC/MS [MH+] 342. |
| 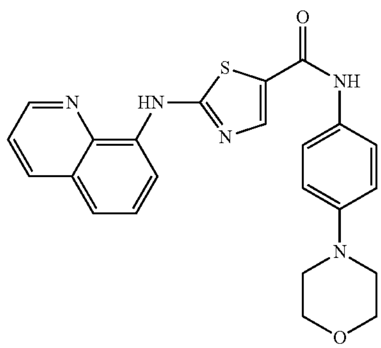 [SMILES: O=C(Nc1ccc(N2CCOCC2)cc1)c1cnc(Nc2cccc3cccnc23)s1] | N-(4-morpholinophenyl)-2-(quinolin-8-ylamino)thiazole-5-carboxamide | LC/MS [MH+] 432. |

Example 4: Synthesis of N-(cyclopropylmethyl)-4-(4-(6-hydroxy-3,4-dihydroquinolin-1(2H)-yl)pyrimidin-2-ylamino)benzenesulfonamide (Pyrintegrin)

The reaction flask containing 2,4-dichloropyrimidine (372 mg, 2.5 mmol), 6-methoxy-1,2,3,4-tetrahydroquinoline (489 mg, 3 mmol) and diisopropylethylamine (0.52 mL, 3 mmol) in n-butanol (10 mL) was heated at 40° C. overnight. The solvent was evaporated, and the residue was purified by flash column chromatography to give 2-Chloro-4-(6-methoxy-3,4-dihydroquinolin-1(2H)-yl)pyrimidine (551 mg, 80%). This intermediate (250 mg, 0.91 mmol) was then dissolved in dichloromethane and treated with BBr$_3$ (1 M in dichloromethane) (1 mL, 1 mmol) at −78° C. The reaction mixture was slowly warmed up to room temperature and stirred for 1 hr, poured into water, extracted with dichloromethane. The combined organics were dried over anhydrous Na$_2$SO$_4$ and concentrated. The residue was purified by flash column chromatography to give 2-Chloro-4-(6-hydroxy-3,4-dihydroquinolin-1(2H)-yl)pyrimidine (154 mg, 65%). To a stirred solution of 2-chloro-4-(6-hydroxy-3,4-dihydroquinolin-1 (2H)-yl)pyrimidine (29 mg, 0.11 mmol) and 4-amino-N-(cyclopropylmethyl)benzenesulfonamide (27 mg, 0.12 mmol) in DMF (0.5 mL) was added p-toluenesulfonic acid (2 M in dioxane) (55 µL, 0.11 mmol). The reaction mixture was stirred at 90° C. overnight, then purified by HPLC to give the title compound (27 mg, 56%).

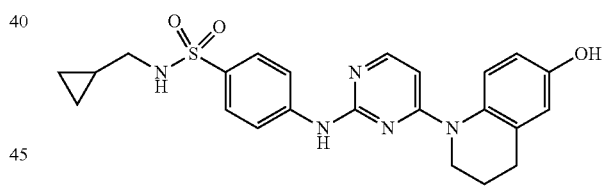

N-(Cyclopropylmethyl)-4-(4-(6-hydroxy-3,4-dihydroquinolin-1(2H)-yl)pyrimidin-2-ylamino)benzenesulfonamide Exact mass calculated for $C_{23}H_{25}N_5O_3S$: 451.2, found LCMS m/z=452.3 (M+H+).

$^1$H NMR (400 MHz, d$_6$-DMSO) 0.05-0.09 (m, 2H), 0.32-0.36 (m, 2H), 0.75-0.81 (m, 1H), 1.90-1.95 (m, 2H), 2.64 (t, J=6.4 Hz, 4H), 3.93 (t, J=6.5 Hz, 2H), 6.59 (d, J=7.1 Hz, 1H), 6.66-6.70 (m, 2H), 7.25-7.28 (m, 1H), 7.64 (t, J=5.9 Hz, 1H), 7.74 (d, J=8.8 Hz, 2H), 7.82 (d, J=8.8 Hz, 2H), 8.01 (d, J=7.1 Hz, 1H), 10.79 (s, 1H).

Example 5: Synthesis of Pyrintegrin Derivatives

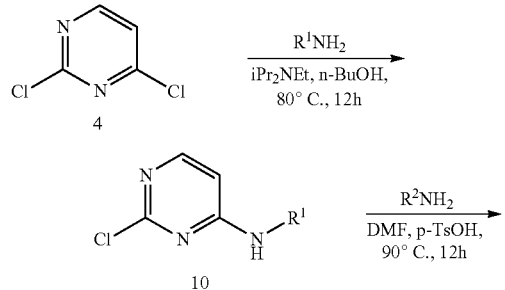

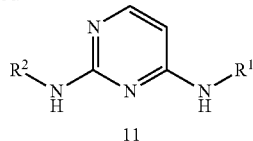

To a mixture of 2,4-dichloropyrimidine 4 (1.0 eq.), $R^1NH_2$ (1.2 eq.) and diisopropylethylamine (1.2 eq.) in n-butanol was heated at 80° C. overnight. The solvent was evaporated, and the residue was purified by flash column chromatography to intermediate 10 in excellent yield (>80%), which was then treated with $R^2NH_2$ (1.2 eq.) in DMF was added p-toluenesulfonic acid (2 M in dioxane) (1.2 eq.). The reaction mixture was stirred at 90° C. overnight, and then purified directly by preparative HPLC to give Pyrintegrin derivatives 11 in excellent yields.

| Structure | Name | Data |
|---|---|---|
| 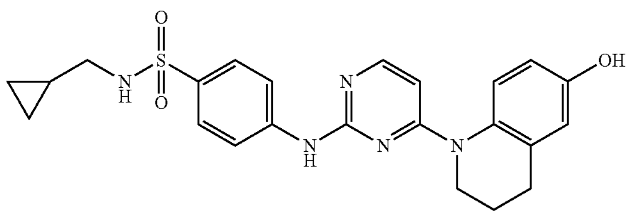 [SMILES: O=S(=O)(NCC1CC1)c1ccc(Nc2nccc(N3CCCc4cc(O)ccc43)n2)cc1] | N-(cyclopropylmethyl)-4-(4-(6-hydroxy-3,4-dihydroquinolin-1(2H)-yl)pyrimidin-2-ylamino)benzenesulfonamide | LC/MS [MH⁺] 452. |
| 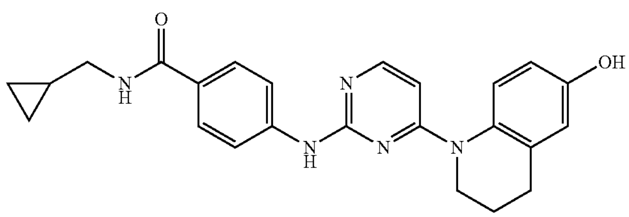 [SMILES: O=C(NCC1CC1)c1ccc(Nc2nccc(N3CCCc4cc(O)ccc43)n2)cc1] | N-(cyclopropylmethyl)-4-(4-(6-hydroxy-3,4-dihydroquinolin-1(2H)-yl)pyrimidin-2-ylamino)benzamide | LC/MS [MH⁺] 416. |
| 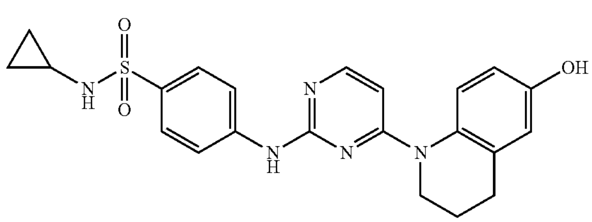 [SMILES: O=S(=O)(NC1CC1)c1ccc(Nc2nccc(N3CCCc4cc(O)ccc43)n2)cc1] | N-cyclopropyl-4-(4-(6-hydroxy-3,4-dihydroquinolin-1(2H)-yl)pyrimidin-2-ylamino)benzenesulfonamide | LC/MS [MH⁺] 438. |
| 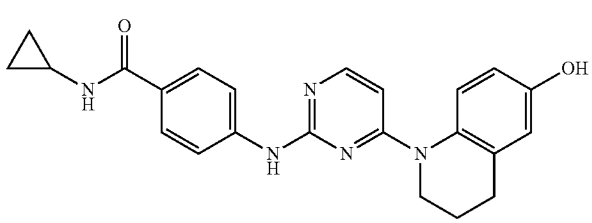 [SMILES: O=C(NC1CC1)c1ccc(Nc2nccc(N3CCCc4cc(O)ccc43)n2)cc1] | N-cyclopropyl-4-(4-(6-hydroxy-3,4-dihydroquinolin-1(2H)-yl)pyrimidin-2-ylamino)benzamide | LC/MS [MH⁺] 402. |
| 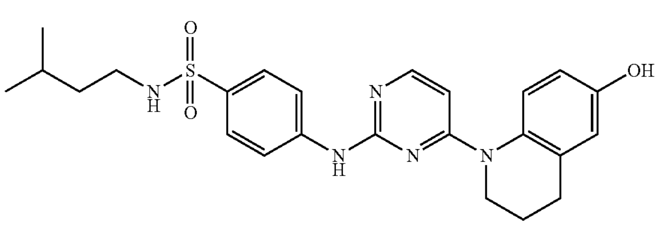 [SMILES: CC(C)CCNS(=O)(=O)c1ccc(Nc2nccc(N3CCCc4cc(O)ccc43)n2)cc1] | 4-(4-(6-hydroxy-3,4-dihydroquinolin-1(2H)-yl)pyrimidin-2-ylamino)-N-isobutylbenzenesulfonamide | LC/MS [MH⁺] 468. |

-continued

| Structure | Name | Data |
|---|---|---|
| 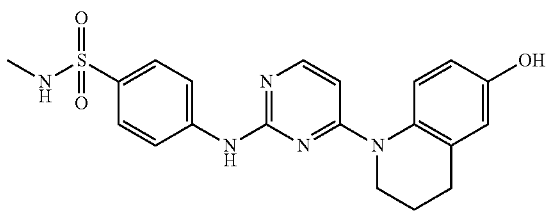 [SMILES: CNS(=O)(=O)c1ccc(Nc2nccc(N3CCCc4cc(O)ccc43)n2)cc1] | 4-(4-(6-hydroxy-3,4-dihydroquinolin-1(2H)-yl)pyrimidin-2-ylamino)-N-methylbenzenesulfonamide | LC/MS [MH+] 412. |
| 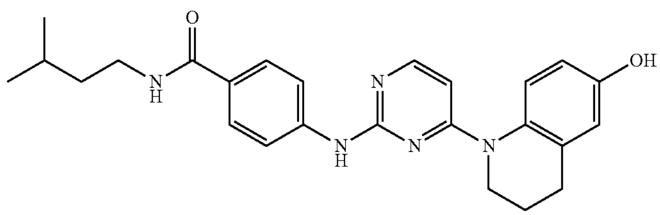 [SMILES: CC(C)CCNC(=O)c1ccc(Nc2nccc(N3CCCc4cc(O)ccc43)n2)cc1] | 4-(4-(6-hydroxy-3,4-dihydroquinolin-1(2H)-yl)pyrimidin-2-ylamino)-N-isopentylbenzamide | LC/MS [MH+] 432. |
| 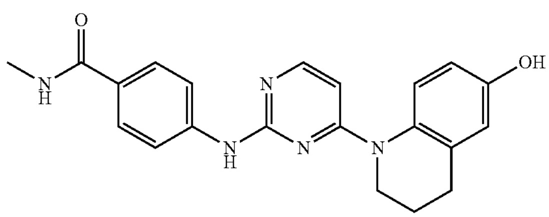 [SMILES: CNC(=O)c1ccc(Nc2nccc(N3CCCc4cc(O)ccc43)n2)cc1] | 4-(4-(6-hydroxy-3,4-dihydroquinolin-1(2H)-yl)pyrimidin-2-ylamino)-N-methylbenzamide | LC/MS [MH+] 376. |
| 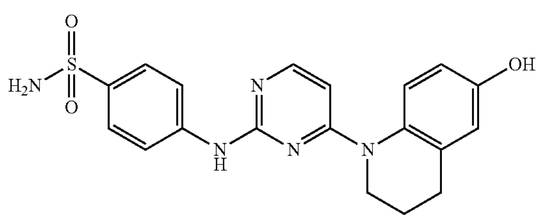 [SMILES: NS(=O)(=O)c1ccc(Nc2nccc(N3CCCc4cc(O)ccc43)n2)cc1] | 4-(4-(6-hydroxy-3,4-dihydroquinolin-1(2H)-yl)pyrimidin-2-ylamino)benzenesulfonamide | LC/MS [MH+] 398. |
| 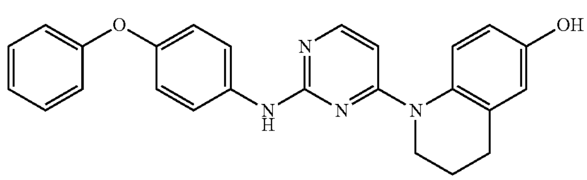 [SMILES: Oc1ccc2c(c1)CCCN2c1ccnc(Nc2ccc(Oc3ccccc3)cc2)n1] | 1-(2-(4-phenoxyphenylamino)pyrimidin-4-yl)-1,2,3,4-tetrahydroquinolin-6-ol | LC/MS [MH+] 411. |
| 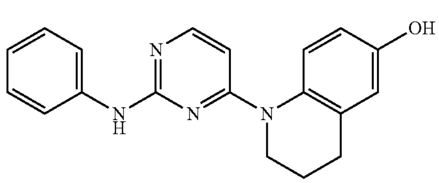 [SMILES: Oc1ccc2c(c1)CCCN2c1ccnc(Nc2ccccc2)n1] | 1-(2-(phenylamino)pyrimidin-4-yl)-1,2,3,4-tetrahydroquinolin-6-ol | LC/MS [MH+] 319. |
| 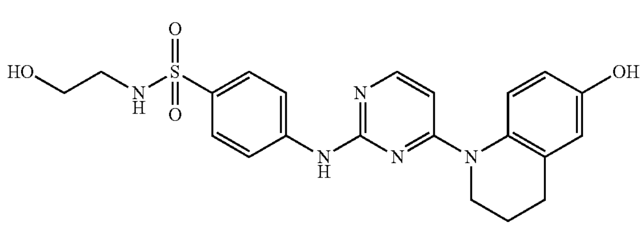 [SMILES: O=S(=O)(NCCO)c1ccc(Nc2nccc(N3CCCc4cc(O)ccc43)n2)cc1] | 4-(4-(6-hydroxy-3,4-dihydroquinolin-1(2H)-yl)pyrimidin-2-ylamino)-N-(2-hydroxyethyl)benzenesulfonamide | LC/MS [MH+] 442. |

-continued

| Structure | Name | Data |
|---|---|---|
| 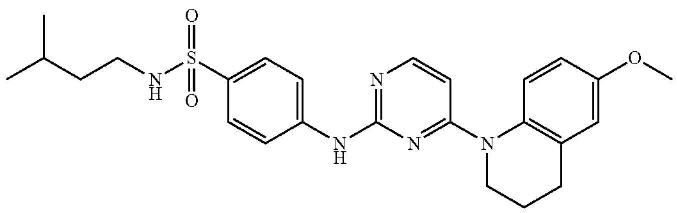 [SMILES: COc1ccc2c(c1)CCCN2c1ccnc(Nc2ccc(S(=O)(=O)NCCC(C)C)cc2)n1] | N-isopentyl-4-(4-(6-methoxy-3,4-dihydroquinolin-1(2H)-yl)pyrimidin-2-ylamino)benzenesulfonamide | LC/MS [MH+] 482. |
| 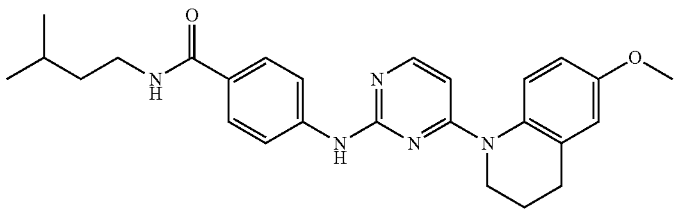 [SMILES: COc1ccc2c(c1)CCCN2c1ccnc(Nc2ccc(C(=O)NCCC(C)C)cc2)n1] | N-isopentyl-4-(4-(6-methoxy-3,4-dihydroquinolin-1(2H)-yl)pyrimidin-2-ylamino)benzamide | LC/MS [MH+] 446. |
| 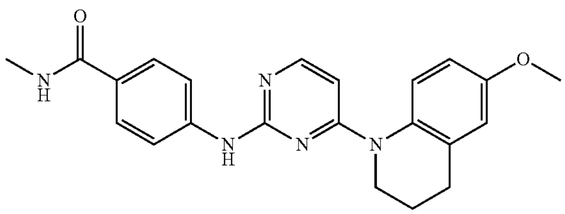 | 4-(4-(6-methoxy-3,4-dihydroquinolin-1(2H)-yl)pyrimidin-2-ylamino)-N-methylbenzamide | LC/MS [MH+] 390. |
| | 4-(4-(6-methoxy-3,4-dihydroquinolin-1(2H)-yl)pyrimidin-2-ylamino)-N-methylbenzenesulfonamide | LC/MS [MH+] 423. |
| 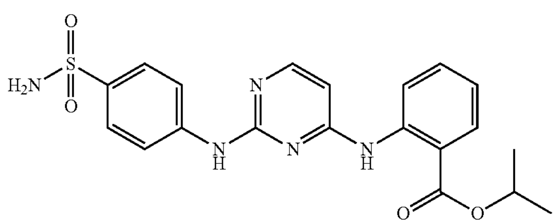 [SMILES: CC(C)OC(=O)c1ccccc1Nc1ccnc(Nc2ccc(S(N)(=O)=O)cc2)n1] | isopropyl 2-(2-(4-sulfamoylphenylamino)pyrimidin-4-ylamino)benzoate | LC/MS [MH+] 428. |
| 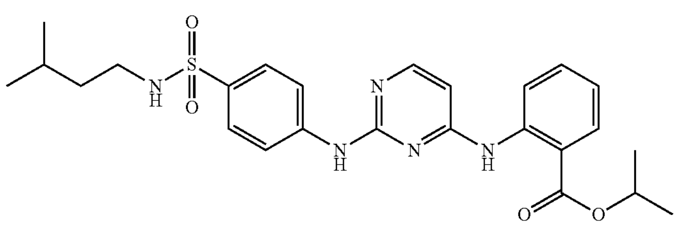 [SMILES: CC(C)CCNS(=O)(=O)c1ccc(Nc2nccc(Nc3ccccc3C(=O)OC(C)C)n2)cc1] | isopropyl 2-(2-(4-(N-isopentylsulfamoyl)phenylamino)pyrimidin-4-ylamino)benzoate | LC/MS [MH+] 498. |
| 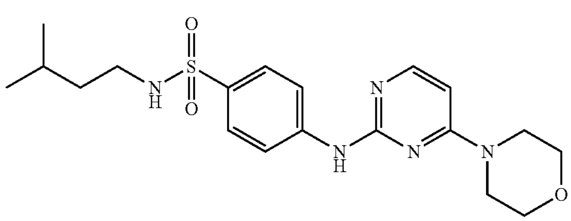 [SMILES: CC(C)CCNS(=O)(=O)c1ccc(Nc2nccc(N3CCOCC3)n2)cc1] | N-isopentyl-4-(4-morpholinopyrimidin-2-ylamino)benzenesulfonamide | LC/MS [MH+] 406. |

-continued

| Structure | Name | Data |
|---|---|---|
| 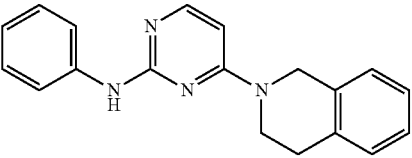 [SMILES: c1ccc(Nc2nccc(N3CCc4ccccc4C3)n2)cc1] | 4-(3,4-dihydroisoquinolin-2(1H)-yl)-N-phenylpyrimidin-2-amine | LC/MS Rt = 2.03 min, [MH+] 303. |
| 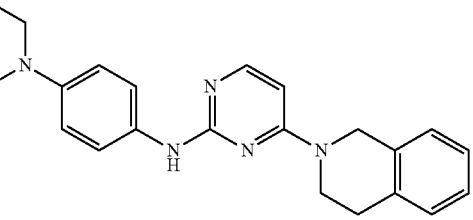 | 4-(3,4-dihydroisoquinolin-2(1H)-yl)-N-(4-morpholinophenyl)pyrimidin-2-amine | LC/MS Rt = 1.84 min, [MH+] 388. |
| 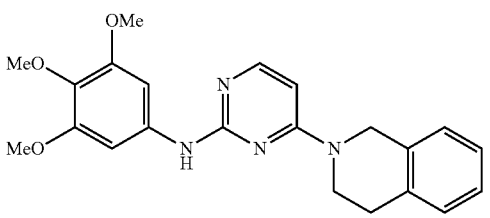 [SMILES: COc1cc(Nc2nccc(N3CCc4ccccc4C3)n2)cc(OC)c1OC] | 4-(3,4-dihydroisoquinolin-2(1H)-yl)-N-(3,4,5-trimethoxyphenyl)pyrimidin-2-amine | LC/MS Rt = 1.95 min, [MH+] 393. |
| 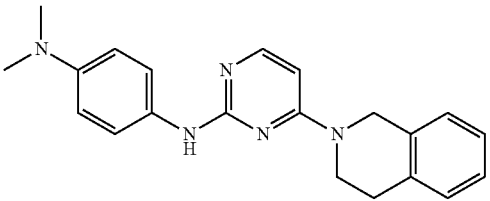 [SMILES: CN(C)c1ccc(Nc2nccc(N3CCc4ccccc4C3)n2)cc1] | N1-(4-(3,4-dihydroisoquinolin-2(1H)-yl)pyrimidin-2-yl)-N4,N4-dimethylbenzene-1,4-diamine | LC/MS Rt = 1.49 min, [MH+] 346. |
| 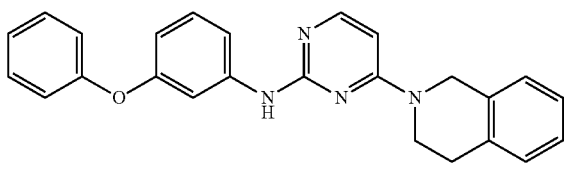 [SMILES: c1ccc(Oc2cccc(Nc3nccc(N4CCc5ccccc5C4)n3)c2)cc1] | 4-(3,4-dihydroisoquinolin-2(1H)-yl)-N-(3-phenoxyphenyl)pyrimidin-2-amine | LC/MS Rt = 2.36 min, [MH+] 395. |
| 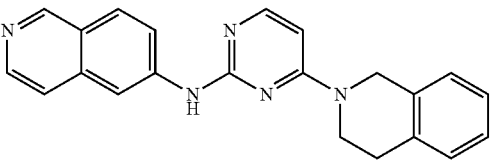 [SMILES: c1ccc2c(c1)CCN(c1ccnc(Nc3ccc4cnccc4c3)n1)C2] | N-(4-(3,4-dihydroisoquinolin-2(1H)-yl)pyrimidin-2-yl)isoquinolin-6-amine | LC/MS Rt = 1.51 min, [MH+] 354. |
| 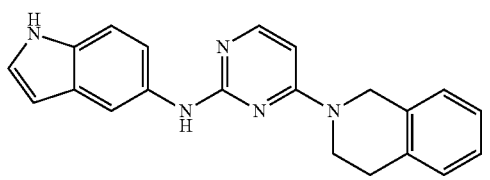 [SMILES: c1ccc2c(c1)CCN(c1ccnc(Nc3ccc4[nH]ccc4c3)n1)C2] | N-(4-(3,4-dihydroisoquinolin-2(1H)-yl)pyrimidin-2-yl)-1H-indol-5-amine | LC/MS Rt = 1.96 min, [MH+] 342. |
| 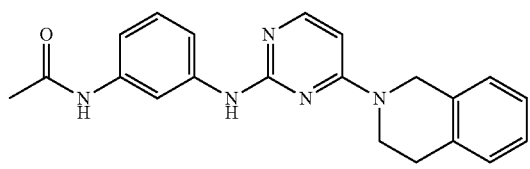 [SMILES: CC(=O)Nc1cccc(Nc2nccc(N3CCc4ccccc4C3)n2)c1] | N-(3-(4-(3,4-dihydroisoquinolin-2(1H)-yl)pyrimidin-2-ylamino)phenyl)acetamide | LC/MS Rt = 1.80 min, [MH+] 360. |

-continued

| Structure | Name | Data |
|---|---|---|
| 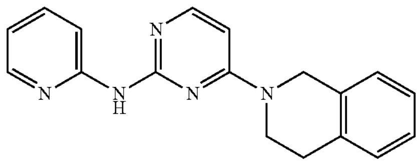 [SMILES: c1ccc(Nc2nccc(N3CCc4ccccc4C3)n2)nc1] | 4-(3,4-dihydroisoquinolin-2(1H)-yl)-N-(pyridin-2-yl)pyrimidin-2-amine | LC/MS Rt = 1.95 min, [MH+] 304. |
| 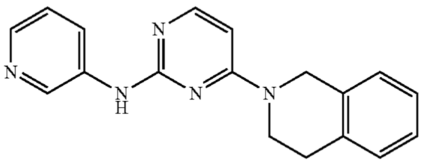 [SMILES: c1cncc(Nc2nccc(N3CCc4ccccc4C3)n2)c1] | 4-(3,4-dihydroisoquinolin-2(1H)-yl)-N-(pyridin-3-yl)pyrimidin-2-amine | LC/MS Rt = 1.42 min, [MH+] 304. |
| 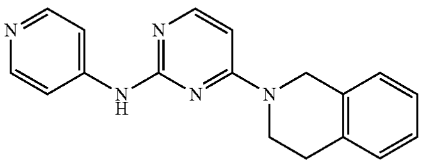 [SMILES: c1ccc2c(c1)CCN(c1ccnc(Nc3ccncc3)n1)C2] | 4-(3,4-dihydroisoquinolin-2(1H)-yl)-N-(pyridin-4-yl)pyrimidin-2-amine | LC/MS Rt = 1.40 min, [MH+] 304. |
| 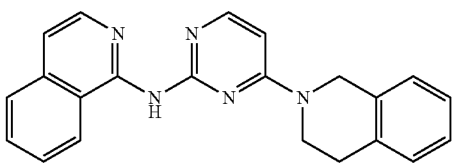 [SMILES: c1ccc2c(c1)CCN(c1ccnc(Nc3nccc4ccccc34)n1)C2] | N-(4-(3,4-dihydroisoquinolin-2(1H)-yl)pyrimidin-2-yl)isoquinolin-1-amine | LC/MS Rt = 2.20 min, [MH+] 354. |
| 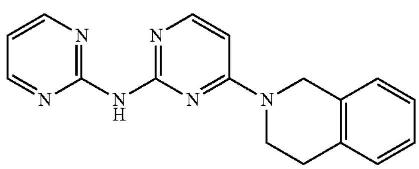 [SMILES: c1cnc(Nc2nccc(N3CCc4ccccc4C3)n2)nc1] | 4-(3,4-dihydroisoquinolin-2(1H)-yl)-N-(pyrimidin-2-yl)pyrimidin-2-amine | LC/MS Rt = 1.70 min, [MH+] 305. |
| 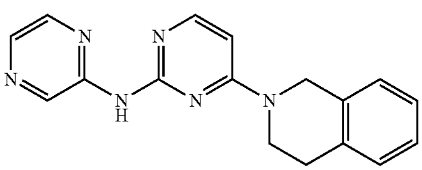 [SMILES: c1ccc2c(c1)CCN(c1ccnc(Nc3cnccn3)n1)C2] | 4-(3,4-dihydroisoquinolin-2(1H)-yl)-N-(pyrazin-2-yl)pyrimidin-2-amine | LC/MS Rt = 1.56 min, [MH+] 305. |
| 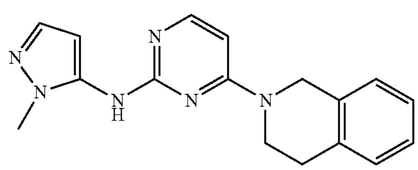 [SMILES: Cn1nccc1Nc1nccc(N2CCc3ccccc3C2)n1] | 4-(3,4-dihydroisoquinolin-2(1H)-yl)-N-(1-methyl-1H-pyrazol-5-yl)pyrimidin-2-amine | LC/MS Rt = 1.64 min, [MH+] 307. |
| 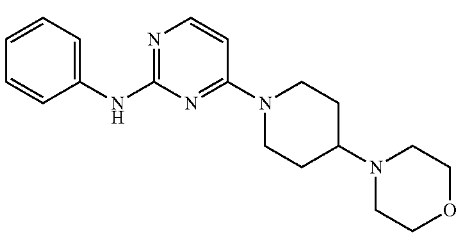 [SMILES: c1ccc(Nc2nccc(N3CCC(N4CCOCC4)CC3)n2)cc1] | 4-(4-morpholinopiperidin-1-yl)-N-phenylpyrimidin-2-amine | LC/MS Rt = 0.97 min, [MH+] 340. |

-continued

| Structure | Name | Data |
|---|---|---|
| 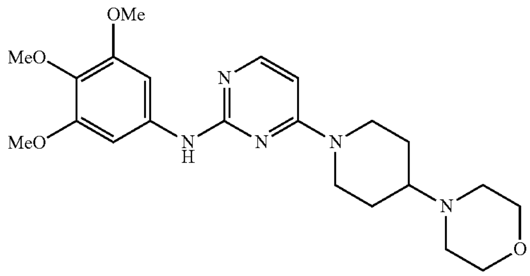 [SMILES: COc1cc(Nc2nccc(N3CCC(N4CCOCC4)CC3)n2)cc(OC)c1OC] | 4-(4-morpholinopiperidin-1-yl)-N-(3,4,5-trimethoxyphenyl)pyrimidin-2-amine | LC/MS Rt = 1.11 min, [MH⁺] 430. |
| 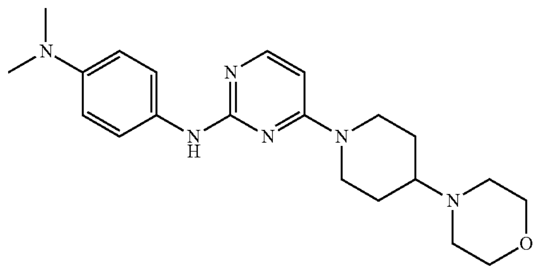 [SMILES: CN(C)c1ccc(Nc2nccc(N3CCC(N4CCOCC4)CC3)n2)cc1] | N1,N1-dimethyl-N4-(4-(4-morpholinopiperidin-1-yl)pyrimidin-2-yl)benzene-1,4-diamine | LC/MS [MH⁺] 383 |
| 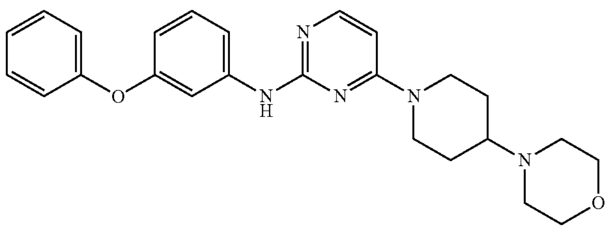 [SMILES: c1ccc(Oc2cccc(Nc3nccc(N4CCC(N5CCOCC5)CC4)n3)c2)cc1] | 4-(4-morpholinopiperidin-1-yl)-N-(3-phenoxyphenyl)pyrimidin-2-amine | LC/MS [MH⁺] 379 |
| 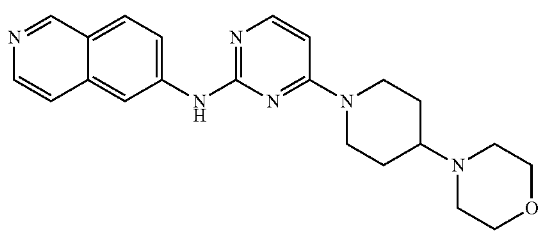 [SMILES: c1cc2cc(Nc3nccc(N4CCC(N5CCOCC5)CC4)n3)ccc2cn1] | N-(4-(4-morpholinopiperidin-1-yl)pyrimidin-2-yl)isoquinolin-6-amine | LC/MS [MH⁺] 391 |
| | N-(4-(4-morpholinopiperidin-1-yl)pyrimidin-2-yl)-1H-indol-5-amine | LC/MS [MH⁺] 379 |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method for preparing a cell having reduced differentiation in vitro, the method comprising:
   (a) obtaining cells comprising stem cells or progenitor cells; and
   (b) contacting the cells with an amount of a compound having formula (I) sufficient to prevent or reduce the cells from differentiation as compared to cells in the absence of the compound, wherein the compound of formula (I) is as follows:

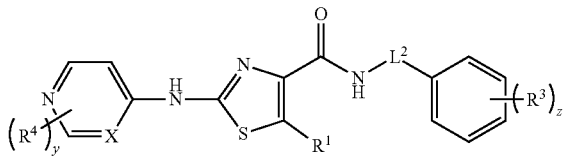

(I)

wherein,
   $L^2$ is substituted or unsubstituted $C_1$-$C_{10}$ alkylene; and
   y is an integer from 0 to 3;
   z is an integer from 0 to 5;
   X is —N═, —CH═ or —CR$^5$═;
   $R^1$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
   $R^3$, $R^4$ and $R^5$ are independently —CN, —S(O)$_n$R$^6$, —NR$^7$R$^8$, —C(O)R$^9$, —C(O)R$^{11}$, —NR$^{12}$—C(O)—OR$^{13}$, —C(O)NR$^{14}$R$^{15}$, —NR$^{16}$S(O)$_2$R$^{17}$, —OR$^{18}$, —S(O)$_2$N(R$^{19}$)$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein n is an integer from 0 to 2, wherein if z is greater than 1, two $R^3$ moieties are optionally joined together to form a substituted or unsubstituted cycloalkyl, substituted or unsubstituted heterocycloalkyl, substituted or unsubstituted aryl, or substituted or unsubstituted heteroaryl; and
   $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$ and $R^{19}$ are independently hydrogen, substituted or unsubstituted alkyl, substituted or unsubstituted heteroalkyl, unsubstituted cycloalkyl, substituted or unsubstituted heterocycloalkyl, substituted or unsubstituted aryl, or substituted or unsubstituted heteroaryl;
   or a racemate, diastereomer, tautomer, or a geometric isomer thereof, or a pharmaceutically acceptable salt thereof.

2. The method of claim 1, wherein the cells are:
   (a) in adherent cultures;
   (b) in suspension cultures;
   (c) single dissociated cells; or
   (d) aggregated cells.

3. The method of claim 1, wherein the contacting step further comprises:
   passaging the cells in cultures comprising the compound having formula (I) for at least 5, 10, 15, or 20, or more generations.

4. The method of claim 3, wherein the cells:
   (a) are homogenous;
   (b) are induced pluripotent stem cells;
   (c) have morphology of hESCs;
   (d) express pluripotency markers;
   (e) maintain normal karyotype;
   (f) are capable of self-renewal;
   (g) are protected from cell death;
   (h) are capable of forming teratomas;
   (i) are capable of differentiating into three primary germ layers;
   (j) are capable of lineage-specific differentiation;
   (k) are capable of forming embryoid bodies after single cell dissociation;
   (l) maintain their current state of differentiation; and/or
   (m) have increased cell adhesion ability after single cell dissociation.

5. The method of claim 1, wherein the contacting step further comprises:
   (a) modulating cell surface level of E-cadherins comprising (i) stabilizing E-cadherin on cell surface; and/or (ii) inhibiting endocytosis of E-cadherins; or
   (b) modulating integrin activity comprising (i) increasing integrin expression; and/or (ii) converting integrin into an active conformation.

6. The method of claim 3, wherein the cells in cultures comprising the compound having formula (I) are passaged for at least 20 generations or more generations.

7. The method of claim 3, wherein the cultures are:
   (a) chemically-defined;
   (b) feeder-free or non-feeder cell conditioned; and/or
   (c) animal product-free.

8. A population of isolated cells prepared according to the method of claim 1, wherein the isolated cells have reduced differentiation.

9. A composition comprising the population of isolated cells of claim 8.

10. The composition of claim 9, further comprising a compound of formula (I):

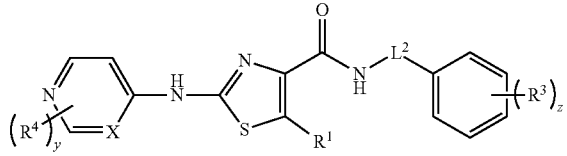

(I)

wherein,
   $L^2$ is substituted or unsubstituted $C_1$-$C_{10}$ alkylene; and
   y is an integer from 0 to 3;
   z is an integer from 0 to 5;
   X is —N═, —CH═ or —CR$^5$═;
   $R^1$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
   $R^3$, $R^4$ and $R^5$ are independently —CN, —S(O)$_n$R$^6$, —NR$^7$R$^8$, —C(O)R$^9$, —NR$^{10}$—C(O)R$^{11}$, —NR$^{12}$—C (O)—OR$^{13}$, —C(O)NR$^{14}$R$^{15}$, —NR$^{16}$S(O)$_2$R$^{17}$, —S(O)$_2$N(R$^{19}$)$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein n is an integer from 0 to 2, wherein if z is greater than 1, two R$^3$ moieties are optionally joined together to form a substituted or unsubstituted cycloalkyl, substituted or unsubstituted heterocycloalkyl, substituted or unsubstituted aryl, or substituted or unsubstituted heteroaryl; and R$^6$, R$^7$, R$^8$, R$^9$, R$^{10}$, R$^{11}$, R$^{12}$, R$^{13}$, R$^{14}$, R$^{15}$, R$^{16}$, R$^{17}$, R$^{18}$ and R$^{19}$ are independently hydrogen, substituted or unsubstituted alkyl, substituted or unsubstituted heteroalkyl, unsubstituted cycloalkyl, substituted or unsubstituted heterocycloalkyl, substituted or unsubstituted aryl, or substituted or unsubstituted heteroaryl;

or a racemate, diastereomer, tautomer, or a geometric isomer thereof, or a pharmaceutically acceptable salt thereof.

11. A method for treating an individual by administering the composition of claim 9 to an individual in need of treatment.

12. The method of claim 11, wherein the composition further comprises a compound of formula (I):

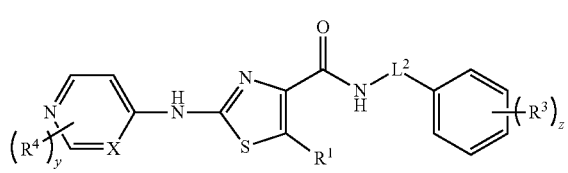

(I)

wherein,
L$^2$ is substituted or unsubstituted C$_1$-C$_{10}$ alkylene; and
y is an integer from 0 to 3;
z is an integer from 0 to 5;
X is —N═, —CH═ or —CR$^5$═;
R$^1$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
R$^3$, R$^4$ and R$^5$ are independently —CN, —S(O)$_n$R$^6$, —NR$^7$R$^8$, —C(O)R$^9$, —NR$^{10}$—C(O)R$^{11}$, —NR$^{12}$—C(O)—OR$^{13}$, —C(O)NR$^{14}$R$^{15}$, —NR$^{16}$S(O)$_2$R$^{17}$, —S(O)$_2$N(R$^{19}$)$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein n is an integer from 0 to 2, wherein if z is greater than 1, two R$^3$ moieties are optionally joined together to form a substituted or unsubstituted cycloalkyl, substituted or unsubstituted heterocycloalkyl, substituted or unsubstituted aryl, or substituted or unsubstituted heteroaryl; and R$^6$, R$^7$, R$^8$, R$^9$, R$^{10}$, R$^{11}$, R$^{12}$, R$^{13}$, R$^{14}$, R$^{15}$, R$^{16}$, R$^{17}$, R$^{18}$ and R$^{19}$ are independently hydrogen, substituted or unsubstituted alkyl, substituted or unsubstituted heteroalkyl, unsubstituted cycloalkyl, substituted or unsubstituted heterocycloalkyl, substituted or unsubstituted aryl, or substituted or unsubstituted heteroaryl;

or a racemate, diastereomer, tautomer, or a geometric isomer thereof, or a pharmaceutically acceptable salt thereof.

13. The method of claim 11, wherein the individual has a central nervous system injury; and wherein the composition is administered in an amount sufficient to promote axonal regeneration and/or functional recovery in the injured central nervous system.

14. The method of claim 11, wherein the individual is in need of an organ, cell, or tissue transplantation; and wherein the composition is administered during and/or after transplantation in an amount sufficient to improve organ, cell, or tissue transplantation.

15. A method for treating an individual by administering a composition comprising a compound of formula (I) to an individual in need of treatment, wherein the compound of formula (I) is as follows:

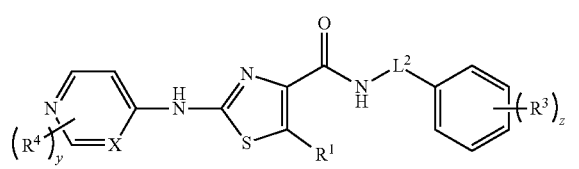

(I)

wherein,
L$^2$ is substituted or unsubstituted C$_1$-C$_{10}$ alkylene; and
y is an integer from 0 to 3;
z is an integer from 0 to 5;
X is —N═, —CH═ or —CR$^5$═;
R$^1$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
R$^3$, R$^4$ and R$^5$ are independently —CN, —S(O)$_n$R$^6$, —NR$^7$R$^8$, —C(O)R$^9$, —C(O)R$^{11}$, —NR$^{12}$—C(O)—OR$^{13}$, —C(O)NR$^{14}$R$^{15}$, —NR$^{16}$S(O)$_2$R$^{17}$, —OR$^{18}$, —S(O)$_2$N(R$^{19}$)$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein n is an integer from 0 to 2, wherein if z is greater than 1, two R$^3$ moieties are optionally joined together to form a substituted or unsubstituted cycloalkyl, substituted or unsubstituted heterocycloalkyl, substituted or unsubstituted aryl, or substituted or unsubstituted heteroaryl; and R$^6$, R$^7$, R$^8$, R$^9$, R$^{10}$, R$^{11}$, R$^{12}$, R$^{13}$, R$^{14}$, R$^{15}$, R$^{16}$, R$^{17}$, R$^{18}$ and R$^{19}$ are independently hydrogen, substituted or unsubstituted alkyl, substituted or unsubstituted heteroalkyl, unsubstituted cycloalkyl, substituted or unsubstituted heterocycloalkyl, substituted or unsubstituted aryl, or substituted or unsubstituted heteroaryl;

or a racemate, diastereomer, tautomer, or a geometric isomer thereof, or a pharmaceutically acceptable salt thereof.

16. The method of claim 15, wherein the individual has a central nervous system injury; and wherein the composition is administered in an amount sufficient to promote axonal regeneration and/or functional recovery in the injured central nervous system.

17. The method of claim 15, wherein the individual is in need of an organ, cell, or tissue transplantation; and wherein the composition is administered during and/or after transplantation in an amount sufficient to improve organ, cell, or tissue transplantation.

18. A method for preparing a cell having enhanced survival and/or proliferation in vitro, the method comprising:
(a) obtaining cells comprising stem cells or progenitor cells; and
(b) contacting the cells with an amount of a compound having formula (I) sufficient to improve survival of the cells by at least 2-fold as compared to cells in the absence of the compound, wherein the compound of formula (I) is as follows:

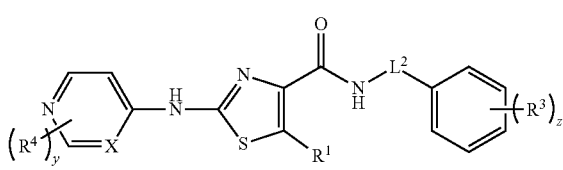

(I)

wherein,
$L^2$ is substituted or unsubstituted $C_1$-$C_{10}$ alkylene; and
y is an integer from 0 to 3;
z is an integer from 0 to 5;
X is —N═, —CH═ or —CR$^5$═;
$R^1$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^3$, $R^4$ and $R^5$ are independently —CN, —S(O)$_n$R$^6$, —NR$^7$R$^8$, —C(O)R$^9$, —NR$^{10}$—C(O)R$^{11}$, —NR$^{12}$—C(O)—OR$^{13}$, —C(O)NR$^{14}$R$^{15}$, —NR$^{16}$S(O)$_2$R$^{17}$, —OR$^{18}$, —S(O)$_2$N(R$^{19}$)$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein n is an integer from 0 to 2, wherein if z is greater than 1, two $R^3$ moieties are optionally joined together to form a substituted or unsubstituted cycloalkyl, substituted or unsubstituted heterocycloalkyl, substituted or unsubstituted aryl, or substituted or unsubstituted heteroaryl; and
$R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$ and $R^{19}$ are independently hydrogen, substituted or unsubstituted alkyl, substituted or unsubstituted heteroalkyl, unsubstituted cycloalkyl, substituted or unsubstituted heterocycloalkyl, substituted or unsubstituted aryl, or substituted or unsubstituted heteroaryl;
or a racemate, diastereomer, tautomer, or a geometric isomer thereof, or a pharmaceutically acceptable salt thereof.

19. The method of claim 18, wherein the cells are:
(a) in adherent cultures;
(b) in suspension cultures;
(c) single dissociated cells; or
(d) aggregated cells.

20. The method of claim 18, wherein the contacting step further comprises:
passaging the cells in cultures comprising the compound having formula (I) for at least 5, 10, 15, or 20, or more generations.

21. The method of claim 20, wherein the cells:
(a) are homogenous;
(b) are induced pluripotent stem cells;
(c) have morphology of hESCs;
(d) express pluripotency markers;
(e) maintain normal karyotype;
(f) are capable of self-renewal;
(g) are protected from cell death;
(h) are capable of forming teratomas;
(i) are capable of differentiating into three primary germ layers;
(l) are capable of lineage-specific differentiation;
(k) are capable of forming embryoid bodies after single cell dissociation;
(l) maintain their current state of differentiation; and/or
(m) have increased cell adhesion ability after single cell dissociation.

22. The method of claim 18, wherein the contacting step further comprises:
(a) modulating cell surface level of E-cadherins comprising (i) stabilizing E-cadherin on cell surface; and/or (ii) inhibiting endocytosis of E-cadherins; or
(b) modulating integrin activity comprising (i) increasing integrin expression; and/or (ii) converting integrin into an active conformation.

23. The method of claim 20, wherein the cells in cultures comprising the compound having formula (I) are passaged for at least 20 generations or more generations.

24. The method of claim 20, wherein the cultures are:
(a) chemically-defined;
(b) feeder-free or non-feeder cell conditioned; and/or
(c) animal product-free.

25. A population of isolated cells prepared according to the method of claim 18, wherein the isolated cells have enhanced survival and/or proliferation.

26. A composition comprising the population of isolated cells of claim 25.

27. The composition of claim 26, further comprising a compound of formula (I):

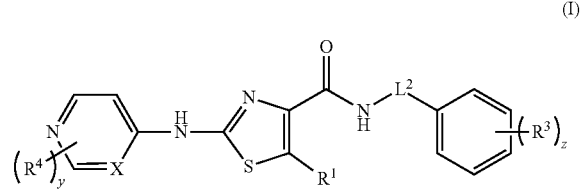

(I)

wherein,
$L^2$ is substituted or unsubstituted $C_1$-$C_{10}$ alkylene; and
y is an integer from 0 to 3;
z is an integer from 0 to 5;
X is —N═, —CH═ or —CR$^5$═;
$R^1$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^3$, $R^4$ and $R^5$ are independently —CN, —S(O)$_n$R$^6$, —NR$^7$R$^8$, —C(O)R$^9$, —NR$^{10}$—C(O)R$^{11}$, —NR$^{12}$—C(O)—OR$^{13}$, —C(O)NR$^{14}$R$^{15}$, —NR$^{16}$S(O)$_2$R$^{17}$, —S(O)$_2$N(R$^{19}$)$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein n is an integer from 0 to 2, wherein if z is greater than 1, two $R^3$ moieties are optionally joined together to form a substituted or unsubstituted cycloalkyl, substituted or unsubstituted heterocycloalkyl, substituted or unsubstituted aryl, or substituted or unsubstituted heteroaryl; and $R^6, R^7, R^8, R^9, R^{10}, R^{11}, R^{12}, R^{13}, R^{14}, R^{15}, R^{16}, R^{17}, R^{18}$ and $R^{19}$ are independently hydrogen, substituted or unsubstituted alkyl, substituted or unsubstituted heteroalkyl, unsubstituted cycloalkyl, substituted or unsubstituted heterocycloalkyl, substituted or unsubstituted aryl, or substituted or unsubstituted heteroaryl;

or a racemate, diastereomer, tautomer, or a geometric isomer thereof, or a pharmaceutically acceptable salt thereof.

28. The method of claim 1, wherein the compound of formula (I) is selected from the group consisting of:

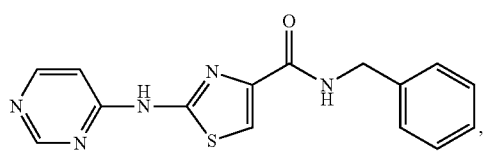

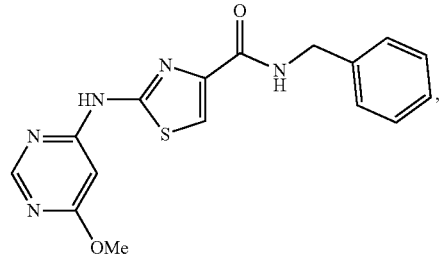

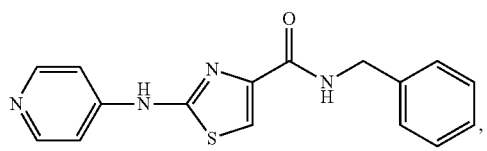

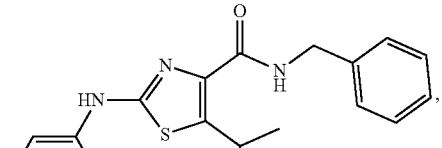

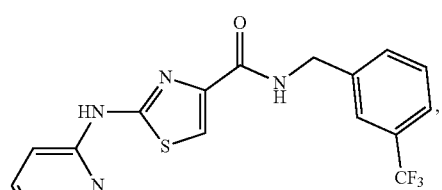

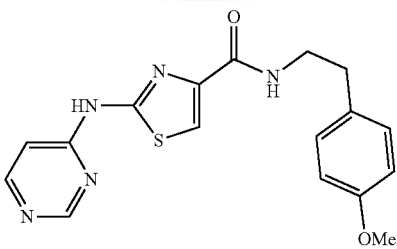

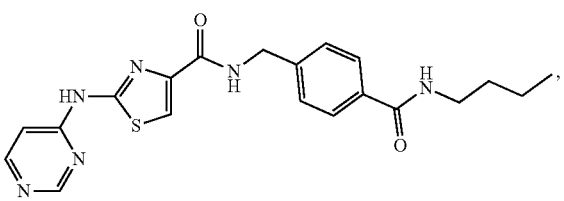

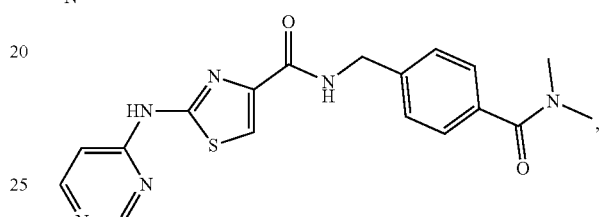

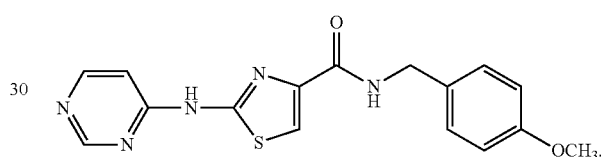

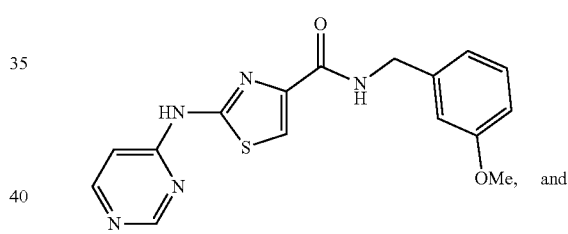

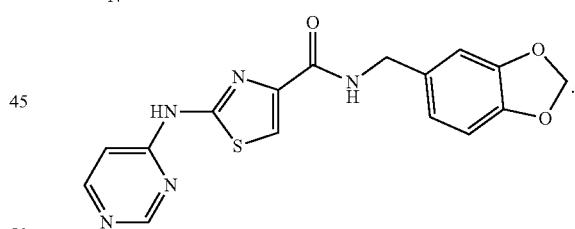

29. The method of claim 1, wherein the compound of formula (I) is selected from the group consisting of:

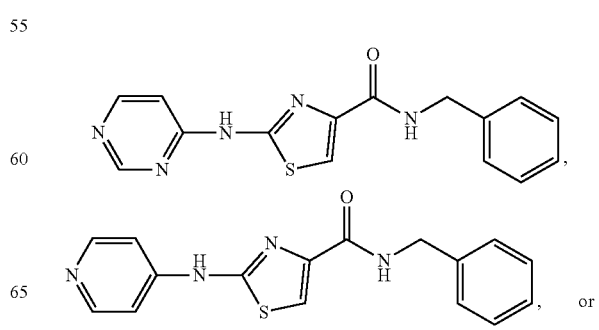

-continued
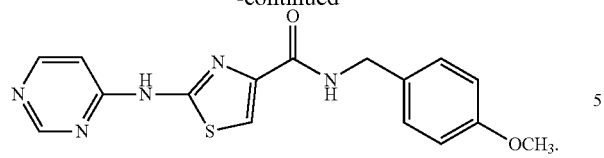
* * * * *

UNITED STATES PATENT AND TRADEMARK OFFICE
CERTIFICATE OF CORRECTION

PATENT NO. : 10,975,352 B2
APPLICATION NO. : 16/431643
DATED : April 13, 2021
INVENTOR(S) : Yue Xu and Sheng Ding It is certified that error appears in the above-identified patent and that said Letters Patent is hereby corrected as shown below:

On the Title Page

In Column 2, item (56), under the "OTHER PUBLICATIONS" in Line 10, please delete "piperazinyhphenyl]amino" and insert -- piperazinyl)phenyl]amino --, therefor.

In the Claims

In Column 65, Claim 1, Line 41, delete "—C(O)$R^{11}$," and insert -- —$NR^{10}$—C(O)$R^{11}$, --, therefor.

In Column 67, Claim 10, Line 2, before "—S(O)$_2$N($R^{19}$)$_2$," insert -- —$OR^{18}$, --.

In Column 67, Claim 12, Line 51, before "—S(O)$_2$N($R^{19}$)$_2$," insert -- —$OR^{18}$, --.

In Column 68, Claim 15, Line 41, delete "—C(O)$R^{11}$," and insert -- —$NR^{10}$—C(O)$R^{11}$, --, therefor.

In Column 70, Claim 21, Line 15, delete "(l)" and insert -- (j) --, therefor.

In Column 70, Claim 27, Line 67, before "—S(O)$_2$N($R^{19}$)$_2$," insert -- —$OR^{18}$, --.

Signed and Sealed this
Nineteenth Day of April, 2022

Katherine Kelly Vidal
*Director of the United States Patent and Trademark Office*